(12) United States Patent
Mower et al.

(10) Patent No.: US 10,799,617 B2
(45) Date of Patent: Oct. 13, 2020

(54) SERIALLY DEPOSITED FIBER MATERIALS AND ASSOCIATED DEVICES AND METHODS

(71) Applicant: Merit Medical Systems, Inc., South Jordan, UT (US)

(72) Inventors: Wayne L. Mower, Bountiful, UT (US); John William Hall, North Salt Lake, UT (US); Rachel L. Simmons, Bountiful, UT (US); Bart Dolmatch, Saratoga, CA (US); F. Mark Ferguson, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 422 days.

(21) Appl. No.: 14/207,344

(22) Filed: Mar. 12, 2014

(65) Prior Publication Data
US 2014/0273703 A1 Sep. 18, 2014

Related U.S. Application Data

(60) Provisional application No. 61/780,646, filed on Mar. 13, 2013, provisional application No. 61/847,875, filed on Jul. 18, 2013.

(51) Int. Cl.
*A61L 27/50* (2006.01)
*F16L 11/115* (2006.01)
(Continued)

(52) U.S. Cl.
CPC .............. *A61L 27/50* (2013.01); *A61L 27/16* (2013.01); *A61L 29/041* (2013.01);
(Continued)

(58) Field of Classification Search
CPC ......... D01D 5/0007; D01D 5/18; D04H 1/728
See application file for complete search history.

(56) References Cited

U.S. PATENT DOCUMENTS 2,772,444 A * 12/1956 Burrows ................... D01F 6/12
264/127
3,047,444 A * 7/1962 Harwood ................. D04H 1/66
156/291
(Continued)

FOREIGN PATENT DOCUMENTS

CN 101584612 11/2009
EP 0457456 11/1991
(Continued)

OTHER PUBLICATIONS

European Search Report dated Aug. 19, 2014 for EP12755426.9.
(Continued)

*Primary Examiner* — Galen H Hauth
(74) *Attorney, Agent, or Firm* — Stoel Rives LLP

(57) ABSTRACT

Fibrous materials and methods of manufacturing fibrous materials are disclosed. In particular, this application discloses methods of making and processing serially deposited fibrous structures, such as serially deposited fibrous mats. Serially deposited fibrous mats may be used in implantable medical devices with various characteristics and features. Serially deposited fibrous mats of various mat thickness, fiber size, porosity, pore size, and fiber density are disclosed. Additionally, serially deposited fibrous mats having various amounts of fiber structures (such as intersections, branches, and bundles) per unit area are also disclosed.

21 Claims, 23 Drawing Sheets

(51) Int. Cl.
  *F16L 11/11*   (2006.01)
  *A61L 31/14*   (2006.01)
  *A61L 27/16*   (2006.01)
  *A61L 31/04*   (2006.01)
  *A61L 29/04*   (2006.01)
  *A61L 29/14*   (2006.01)
  *B29K 27/18*   (2006.01)
  *B29C 55/04*   (2006.01)
  *D01D 5/00*    (2006.01)
  *D01D 5/18*    (2006.01)
  *D01F 6/12*    (2006.01)

(52) U.S. Cl.
  CPC ........... *A61L 29/146* (2013.01); *A61L 31/048* (2013.01); *A61L 31/14* (2013.01); *F16L 11/11* (2013.01); *F16L 11/115* (2013.01); *B29C 55/04* (2013.01); *B29K 2027/18* (2013.01); *D01D 5/0007* (2013.01); *D01D 5/0076* (2013.01); *D01D 5/18* (2013.01); *D01F 6/12* (2013.01); *Y10T 442/60* (2015.04); *Y10T 442/626* (2015.04); *Y10T 442/643* (2015.04)

(56) References Cited

U.S. PATENT DOCUMENTS

| | | | |
|---|---|---|---|
| 3,203,365 A | | 8/1965 | Bowe et al. |
| 4,043,331 A | | 8/1977 | Martin et al. |
| 4,044,404 A | | 8/1977 | Martin et al. |
| 4,096,227 A | | 6/1978 | Gore |
| 4,127,706 A | * | 11/1978 | Martin ................. D01D 5/0038 264/10 |
| 4,223,101 A | | 9/1980 | Fine et al. |
| 4,323,525 A | | 4/1982 | Bornat |
| 4,345,414 A | * | 8/1982 | Bornat .................... D04H 1/56 206/363 |
| 4,552,707 A | | 11/1985 | How |
| 4,689,186 A | | 8/1987 | Bornat |
| 5,167,890 A | * | 12/1992 | Sasshofer ............... B29C 55/06 264/127 |
| 5,236,447 A | | 8/1993 | Kubo |
| 5,328,946 A | | 7/1994 | Tuminello et al. |
| 5,344,297 A | | 9/1994 | Hills |
| 5,509,902 A | | 4/1996 | Raulerson |
| 5,512,051 A | | 4/1996 | Wang et al. |
| 5,552,100 A | | 9/1996 | Shannon et al. |
| 5,562,986 A | | 10/1996 | Yamamoto et al. |
| 5,665,428 A | | 9/1997 | Cha et al. |
| 5,700,572 A | | 12/1997 | Klatt et al. |
| 5,702,658 A | | 12/1997 | Pellegrin et al. |
| 5,741,333 A | | 4/1998 | Frid |
| 5,810,870 A | | 9/1998 | Myers et al. |
| 5,941,910 A | | 8/1999 | Schindler et al. |
| 6,010,529 A | | 1/2000 | Herweck et al. |
| 6,075,180 A | | 6/2000 | Sharber et al. |
| 6,106,913 A | | 8/2000 | Scardino |
| 6,165,212 A | | 12/2000 | Dereume et al. |
| 6,238,430 B1 | | 5/2001 | Klumb |
| 6,306,424 B1 | | 10/2001 | Vyakarnam |
| 6,383,214 B1 | | 5/2002 | Banas et al. |
| 6,436,135 B1 | | 8/2002 | Goldfarb |
| 6,498,207 B1 | | 12/2002 | Hoshikawa et al. |
| 6,517,571 B1 | | 2/2003 | Brauker et al. |
| 6,679,913 B2 | | 1/2004 | Homsy |
| 6,719,783 B2 | | 4/2004 | Lentz et al. |
| 7,115,220 B2 | | 10/2006 | Dubson et al. |
| 7,118,698 B2 | | 10/2006 | Armantrout et al. |
| 7,244,272 B2 | | 7/2007 | Dubson et al. |
| 7,316,754 B2 | | 1/2008 | Ide et al. |
| 7,413,575 B2 | | 8/2008 | Phaneuf et al. |
| 7,416,559 B2 | | 8/2008 | Shalaby |
| 7,485,141 B2 | | 2/2009 | Majercak et al. |
| 7,498,079 B1 | * | 3/2009 | Donckers ................. D01F 6/12 426/394 |
| 7,524,527 B2 | | 4/2009 | Stenzel |
| 7,556,634 B2 | | 7/2009 | Lee et al. |
| 7,582,240 B2 | | 9/2009 | Marin et al. |
| 7,655,175 B2 | | 2/2010 | Michael et al. |
| 7,799,261 B2 | | 9/2010 | Orr et al. |
| 7,857,608 B2 | | 12/2010 | Fabbricante et al. |
| 7,947,069 B2 | | 5/2011 | Sanders |
| 7,981,353 B2 | | 7/2011 | Mitchell et al. |
| 8,052,744 B2 | | 11/2011 | Girton |
| 8,178,030 B2 | | 5/2012 | Anneaux et al. |
| 8,257,640 B2 | | 9/2012 | Anneaux et al. |
| 8,262,979 B2 | | 9/2012 | Anneaux et al. |
| 8,637,109 B2 | | 1/2014 | Grewe et al. |
| 8,691,543 B2 | | 4/2014 | Gaudette et al. |
| 8,771,582 B2 | | 7/2014 | Phaneuf et al. |
| 9,034,031 B2 | | 5/2015 | Anneaux |
| 9,198,999 B2 | | 12/2015 | Hall |
| 9,655,710 B2 | | 5/2017 | Eller |
| 9,775,933 B2 | | 10/2017 | Knisley et al. |
| 9,856,588 B2 | | 1/2018 | Anneaux |
| 10,010,395 B2 | | 7/2018 | Puckett |
| 10,028,852 B2 | | 7/2018 | Hall |
| 10,154,918 B2 | | 12/2018 | Haselby et al. |
| 10,405,963 B2 | | 9/2019 | McAlpine |
| 10,675,850 B2 | | 6/2020 | Hall et al. |
| 2001/0034549 A1 | | 10/2001 | Bartholf et al. |
| 2001/0039446 A1 | | 11/2001 | Edwin et al. |
| 2001/0049551 A1 | | 12/2001 | Tseng et al. |
| 2001/0053929 A1 | | 12/2001 | Vonesh et al. |
| 2002/0077693 A1 | | 6/2002 | Barclay |
| 2002/0082675 A1 | | 6/2002 | Myers |
| 2002/0084178 A1 | | 7/2002 | Dubson |
| 2002/0090725 A1 | | 7/2002 | Simpson et al. |
| 2002/0198588 A1 | | 12/2002 | Armstrong |
| 2003/0040772 A1 | | 2/2003 | Hyodoh et al. |
| 2003/0050711 A1 | | 3/2003 | Laurencin |
| 2003/0074049 A1 | | 4/2003 | Hoganson |
| 2003/0100944 A1 | | 5/2003 | Laksin et al. |
| 2003/0114917 A1 | | 6/2003 | Holloway et al. |
| 2003/0139797 A1 | | 7/2003 | Johnson |
| 2003/0195611 A1 | | 10/2003 | Greenhalgh et al. |
| 2003/0211135 A1 | | 11/2003 | Greenhalgh et al. |
| 2004/0016260 A1 | | 1/2004 | Kobayashi et al. |
| 2004/0030377 A1 | | 2/2004 | Dubson et al. |
| 2004/0033364 A1 | | 2/2004 | Spiridigliozzi et al. |
| 2004/0038038 A1 | | 2/2004 | Yeung |
| 2004/0051201 A1 | | 3/2004 | Greenhalgh et al. |
| 2004/0054397 A1 | | 3/2004 | Smith et al. |
| 2004/0107004 A1 | | 6/2004 | Levine et al. |
| 2004/0167606 A1 | | 8/2004 | Chouinard |
| 2004/0219345 A1 | | 11/2004 | Armantrout et al. |
| 2005/0137675 A1 | | 6/2005 | Dubson et al. |
| 2005/0187605 A1 | | 8/2005 | Greenhalgh et al. |
| 2005/0244453 A1 | | 11/2005 | Stucke et al. |
| 2005/0244639 A1 | | 11/2005 | Marin et al. |
| 2005/0278018 A1 | | 12/2005 | Jensen |
| 2006/0142852 A1 | | 6/2006 | Sowinski et al. |
| 2006/0200232 A1 | | 9/2006 | Phaneuf et al. |
| 2006/0228435 A1 | | 10/2006 | Andrady et al. |
| 2006/0233990 A1 | | 10/2006 | Humphrey et al. |
| 2007/0023131 A1 | * | 2/2007 | Farnsworth ............. A61L 27/52 156/167 |
| 2007/0026036 A1 | | 2/2007 | Falotico et al. |
| 2007/0031607 A1 | | 2/2007 | Dubson et al. |
| 2007/0043428 A1 | | 2/2007 | Jennings et al. |
| 2007/0087027 A1 | | 4/2007 | Greenhalgh et al. |
| 2007/0123973 A1 | | 5/2007 | Roth |
| 2007/0142771 A1 | | 6/2007 | Durcan |
| 2007/0207179 A1 | | 9/2007 | Andersen et al. |
| 2007/0207186 A1 | | 9/2007 | Scanlon et al. |
| 2007/0244569 A1 | | 10/2007 | Weber et al. |
| 2007/0269481 A1 | | 11/2007 | Li et al. |
| 2007/0276477 A1 | | 11/2007 | Lee et al. |
| 2008/0021545 A1 | | 1/2008 | Reneker et al. |
| 2008/0029617 A1 | | 2/2008 | Marshall et al. |
| 2008/0118541 A1 | | 5/2008 | Pacetti |
| 2008/0119943 A1 | | 5/2008 | Armstrong et al. |
| 2008/0199506 A1 | | 8/2008 | Horres et al. |
| 2008/0208323 A1 | | 8/2008 | El-Kurdi et al. |

(56) References Cited

U.S. PATENT DOCUMENTS

| | | |
|---|---|---|
| 2008/0208325 A1 | 8/2008 | Helmus et al. |
| 2008/0234812 A1 | 9/2008 | Pacetti |
| 2008/0242171 A1 | 10/2008 | Huang et al. |
| 2008/0281406 A1 | 11/2008 | Addonizio et al. |
| 2008/0286321 A1 | 11/2008 | Reneker et al. |
| 2008/0288044 A1 | 11/2008 | Osborne |
| 2008/0305143 A1 | 12/2008 | Chen et al. |
| 2008/0319535 A1 | 12/2008 | Craven et al. |
| 2009/0012607 A1 | 1/2009 | Kim et al. |
| 2009/0018643 A1 | 1/2009 | Hashi et al. |
| 2009/0030499 A1 | 1/2009 | Bebb et al. |
| 2009/0082846 A1 | 3/2009 | Chobotov |
| 2009/0088828 A1 | 4/2009 | Shalev et al. |
| 2009/0127748 A1 | 5/2009 | Takahashi |
| 2009/0136651 A1 | 5/2009 | Larsen et al. |
| 2009/0160099 A1 | 6/2009 | Huang |
| 2009/0163994 A1 | 6/2009 | Quigley et al. |
| 2009/0227944 A1 | 9/2009 | Weber |
| 2009/0232920 A1 | 9/2009 | Lozano et al. |
| 2009/0248131 A1 | 10/2009 | Greenan |
| 2009/0248144 A1 | 10/2009 | Bahler et al. |
| 2009/0269429 A1 | 10/2009 | Lozano et al. |
| 2009/0280325 A1 | 11/2009 | Lozano et al. |
| 2010/0013126 A1 | 1/2010 | Ishaque et al. |
| 2010/0042198 A1 | 2/2010 | Burton |
| 2010/0042199 A1 | 2/2010 | Burton |
| 2010/0063574 A1 | 3/2010 | Bogert |
| 2010/0076401 A1 | 3/2010 | Von Oepen et al. |
| 2010/0076543 A1 | 3/2010 | Melsheimer et al. |
| 2010/0093093 A1 | 4/2010 | Leong et al. |
| 2010/0129628 A1 | 5/2010 | Young |
| 2010/0190254 A1 | 7/2010 | Chian et al. |
| 2010/0193999 A1* | 8/2010 | Anneaux .............. D01D 5/0038 264/438 |
| 2010/0233115 A1 | 9/2010 | Patel et al. |
| 2010/0280590 A1 | 11/2010 | Sun et al. |
| 2010/0304205 A1 | 12/2010 | Jo et al. |
| 2010/0323052 A1 | 12/2010 | Orr et al. |
| 2010/0331965 A1 | 12/2010 | Dugas et al. |
| 2011/0030885 A1 | 2/2011 | Anneaux et al. |
| 2011/0031656 A1 | 2/2011 | Anneaux et al. |
| 2011/0060276 A1 | 3/2011 | Schaeffer et al. |
| 2011/0087318 A1 | 4/2011 | Daugherty et al. |
| 2011/0089603 A1 | 4/2011 | Fabbricane et al. |
| 2011/0135806 A1 | 6/2011 | Grewe et al. |
| 2011/0142804 A1 | 6/2011 | Gaudette et al. |
| 2011/0156319 A1 | 6/2011 | Kurokawa et al. |
| 2011/0263456 A1 | 10/2011 | Hartig |
| 2011/0295200 A1 | 12/2011 | Speck et al. |
| 2011/0301696 A1 | 12/2011 | Mangiardi |
| 2012/0114722 A1 | 5/2012 | Ballard et al. |
| 2012/0201988 A1* | 8/2012 | Hansen ................ B01D 53/228 428/36.91 |
| 2012/0271396 A1 | 10/2012 | Zheng |
| 2012/0292810 A1 | 11/2012 | Peno et al. |
| 2012/0316633 A1 | 12/2012 | Flanagan et al. |
| 2013/0018220 A1 | 1/2013 | Vad |
| 2013/0023175 A1 | 1/2013 | Anneaux et al. |
| 2013/0053948 A1 | 2/2013 | Anneaux et al. |
| 2013/0059497 A1 | 3/2013 | Anneaux et al. |
| 2013/0079700 A1 | 3/2013 | Ballard et al. |
| 2013/0085565 A1 | 4/2013 | Eller et al. |
| 2013/0184808 A1 | 7/2013 | Hall et al. |
| 2013/0184810 A1 | 7/2013 | Hall et al. |
| 2013/0231733 A1 | 9/2013 | Knisley et al. |
| 2013/0238086 A1 | 9/2013 | Ballard et al. |
| 2013/0268062 A1 | 10/2013 | Puckett et al. |
| 2013/0316103 A1 | 11/2013 | Anneaux et al. |
| 2014/0012304 A1 | 1/2014 | Lampropoulos et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0273703 A1 | 9/2014 | Mower et al. |
| 2015/0081000 A1 | 3/2015 | Hossainy |
| 2015/0134051 A1 | 5/2015 | Donadio et al. |
| 2015/0320542 A1 | 11/2015 | Gabriele et al. |
| 2016/0250048 A1 | 9/2016 | Hall et al. |
| 2016/0331528 A1 | 11/2016 | Parker |
| 2017/0360993 A1 | 10/2017 | Argentine et al. |
| 2018/0064565 A1 | 3/2018 | Mactaggart |
| 2019/0008665 A1 | 1/2019 | Hall et al. |
| 2019/0060528 A1 | 2/2019 | Skender et al. |
| 2019/0076276 A1 | 3/2019 | Longo |
| 2019/0110911 A1 | 4/2019 | Nae |
| 2020/0015987 A1 | 1/2020 | Einav |

FOREIGN PATENT DOCUMENTS

| | | |
|---|---|---|
| EP | 1605014 | 12/2005 |
| EP | 2363516 | 9/2011 |
| JP | 5140476 | 5/1975 |
| JP | 2007519491 | 7/2007 |
| JP | 2007531833 | 11/2007 |
| JP | 2009232882 | 10/2009 |
| JP | 2010517625 | 5/2010 |
| JP | 2010540190 | 12/2010 |
| KR | 20100074913 | 7/2010 |
| KR | 20100108382 | 10/2010 |
| KR | 1020100108382 | 10/2010 |
| WO | 199800090 | 1/1998 |
| WO | 2003051233 | 6/2003 |
| WO | 2004090206 | 10/2004 |
| WO | WO2005/018600 | 3/2005 |
| WO | 2005074547 | 8/2005 |
| WO | 2005098100 | 10/2005 |
| WO | 2006123340 | 11/2006 |
| WO | WO2007075256 | 7/2007 |
| WO | 2008097592 | 8/2008 |
| WO | 2009046372 | 4/2009 |
| WO | 2009127710 | 10/2009 |
| WO | WO2009/127170 | 10/2009 |
| WO | WO2009146280 | 12/2009 |
| WO | 2010083530 | 7/2010 |
| WO | WO2010132636 | 11/2010 |
| WO | 2012103501 | 8/2012 |
| WO | WO2012103501 | 8/2012 |
| WO | 2012122485 A3 | 3/2013 |
| WO | 2013109528 | 7/2013 |
| WO | 2014007979 | 1/2014 |

OTHER PUBLICATIONS

Office Action dated Jan. 13, 2015 for U.S. Appl. No. 13/827,790.
Office Action dated Feb. 4, 2015 for U.S. Appl. No. 13/360,444.
Office Action dated Feb. 20, 2015 for U.S. Appl. No. 14/044,050.
Office Action dated Feb. 26, 2015 for U.S. Appl. No. 14/152,590.
Extended European Search Report dated Jun. 25, 2015 for EP12739348. 6.
International Preliminary Report dated Apr. 2, 2015 for PCT/US2013/060812.
International Preliminary Report dated Jul. 30, 2013 for PCT/US2012/023006.
Office Action dated Jul. 29, 2015 for U.S. Appl. No. 14/152,626.
Office Action dated Aug. 10, 2015 for U.S. Appl. No. 14/044,050.
Office Action dated Oct. 15, 2015 for U.S. Appl. No. 13/827,790.
Office Action dated Nov. 2, 2015 for U.S. Appl. No. 13/742,077.
Office Action dated Aug. 29, 2014 for U.S. Appl. No. 14/152,590.
Office Action dated Oct. 10, 2014 for U.S. Appl. No. 13/742,025.
Notice of Allowance dated Jul. 11, 2016 for U.S. Appl. No. 13/826,618.
Office Action dated Jun. 8, 2016 for U.S. Appl. No. 14/044,050.
Office Action dated Jun. 9, 2016 for U.S. Appl. No. 14/152,626.
Office Action dated Jun. 30, 2016 for U.S. Appl. No. 14/081,715.
U.S. Appl. No. 14/204,466, filed Mar. 11, 2014, Hall et al.
Office Action dated Jul. 2, 2014 for U.S. Appl. No. 14/044,050.
International Search Report and Written Opinion dated Jun. 26, 2014 for PCT/US2014/024868.
International Search Report and Written Opinion dated Jul. 1, 2014 for PCT/US2014/023416.
International Report on Patentability dated Jul. 22, 2014 for PCT/US2013/021554.

(56) References Cited

OTHER PUBLICATIONS

U.S. Appl. No. 13/829,452, filed Mar. 14, 2013, Hall et al.
International Search Report and Written Opinion dated May 23, 2012 for PCT/US2012/023006.
International Search Report and Written Opinion dated Apr. 26, 2013 for PCT/US2013/021554.
Restriction Requirement dated Jun. 21, 2013 for U.S. Appl. No. 13/360,444.
Restriction Requirement dated Sep. 26, 2013 for U.S. Appl. No. 13/742,025.
International Search Report and Written Opinion dated Sep. 6, 2013 for PCT/US2013/046245.
International Search Report and Written Opinion dated Sep. 17, 2013 for PCT/US2013/060172.
International Search Report and Written Opinion dated Dec. 5, 2013 for PCT/US2013/060812.
Office Action dated Mar. 3, 2014 for U.S. Appl. No. 13/742,025.
Office Action dated May 9, 2014 for U.S. Appl. No. 13/360,444.
European Search Report dated Feb. 12, 2016 for EP13813055.4.
Office Action dated Jan. 12, 2016 for U.S. Appl. No. 14/152,590.
Office Action dated Jan. 22, 2016 for U.S. Appl. No. 14/152,626.
Office Action dated Feb. 22, 2016 for U.S. Appl. No. 13/742,077.
Office Action dated Mar. 28, 2016 for U.S. Appl. No. 13/827,790.
Office Action dated Nov. 20, 2015 for U.S. Appl. No. 13/826,618.
Office Action dated Dec. 18, 2015 for U.S. Appl. No. 14/081,504.
European Search Report dated Sep. 6, 2016 for EP14774594.7.
Office Action dated Sep. 9, 2016 for U.S. Appl. No. 14/081,504.
Office Action dated Sep. 23, 2016 for U.S. Appl. No. 14/152,590.
Office Action dated Sep. 27, 2016 for U.S. Appl. No. 13/827,790.
Office Action dated Oct. 6, 2016 for U.S. Appl. No. 13/360,444.
Office Action dated Oct. 6, 2016 for U.S. Appl. No. 13/742,025.
Office Action dated Oct. 26, 2016 for U.S. Appl. No. 13/742,077.
Office Action dated Nov. 17, 2016 for U.S. Appl. No. 13/829,493.
Office Action dated Nov. 18, 2016 for U.S. Appl. No. 13/826,618.
Notice of Allowance dated Jan. 25, 2017 for U.S. Appl. No. 14/152,626.
Office Action dated Jan. 23, 2017 for U.S. Appl. No. 14/081,715.
Office Action dated Feb. 7, 2017 for U.S. Appl. No. 13/827,790.
Office Action dated Mar. 31, 2017 for U.S. Appl. No. 14/204,466.
Office Action dated Apr. 7, 2017 for U.S. Appl. No. 13/826,618.
Office Action dated Apr. 27, 2017 for U.S. Appl. No. 13/742,077.
Office Action dated May 19, 2017 for U.S. Appl. No. 13/742,025.
Office Action dated Jun. 19, 2017 for U.S. Appl. No. 14/081,504.
Office Action dated Jun. 29, 2017 for U.S. Appl. No. 14/081,715.
Office Action dated Jun. 23, 2017 for U.S. Appl. No. 13/829,493.
Office Action dated Jul. 26, 2017 for U.S. Appl. No. 13/827,790.
Office Action dated Sep. 11, 2017 for U.S. Appl. No. 14/832,422.
Notice of Allowance dated Apr. 3, 2018 for U.S. Appl. No. 14/081,504.
Office Action dated Feb. 16, 2018 for U.S. Appl. No. 13/742,077.
Notice of Allowance dated Oct. 4, 2017 for U.S. Appl. No. 14/204,466.
Office Action dated Oct. 20, 2017 for U.S. Appl. No. 13/826,618.
European Search Report dated Mar. 30, 2016 for EP13838784.0.
Extended European Search Report dated Mar. 30, 2016 for EP13838578.6.
International Search Report and Written Opinion dated Jun. 8, 2016 for PCT/US2016/019487.
Office Action dated Jan. 16, 2018 for U.S. Appl. No. 14/081,715.
Office Action dated Jul. 12, 2017 for U.S. Appl. No. 15/053,232.
Office Action dated Nov. 17, 2017 for U.S. Appl. No. 13/360,444.
Office Action dated Nov. 21, 2017 for U.S. Appl. No. 14/152,590.
Office Action dated Dec. 28, 2017 for U.S. Appl. No. 13/827,790.
Office Action dated Dec. 29, 2017 for U.S. Appl. No. 14/081,504.
Office Action dated May 11, 2018 for U.S. Appl. No. 13/826,618.
Office Action dated May 11, 2018 for U.S. Appl. No. 14/832,422.
Office Action dated Jun. 28, 2018 for U.S. Appl. No. 14/081,715.
Office Action dated Jul. 13, 2018 for U.S. Appl. No. 13/827,790.
Office Action dated Jul. 26, 2018 for U.S. Appl. No. 14/152,590.
Office Action dated Aug. 6, 2018 for U.S. Appl. No. 13/360,444.
Board Decision on Appeal dated Nov. 23, 2018 for U.S. Appl. No. 14/044,050.
European Search Report dated Dec. 6, 2018 for EP13813055.4.
Office Action dated Jan. 2, 2009 for U.S. Appl. No. 13/360,444.
Office Action dated Jan. 2, 2019 for U.S. Appl. No. 14/152,590.
Office Action dated Jan. 10, 2019 for U.S. Appl. No. 13/826,618.
Office Action dated Jan. 14, 2019 for U.S. Appl. No. 13/827,790.
Office Action dated Jan. 17, 2019 for U.S. Appl. No. 14/832,422.
Office Action dated Feb. 8, 2019 for U.S. Appl. No. 14/081,715.
EP Examination Report dated May 28, 2019 for EP12755426.9.
European Search Report dated Aug. 20, 2019 for EP14774594.7.
Notice of Allowance dated Oct. 9, 2019 for U.S. Appl. No. 13/826,618.
Office Action dated Oct. 7, 2019 for U.S. Appl. No. 13/360,444.
Office Action dated Oct. 7, 2019 for U.S. Appl. No. 14/152,590.
Notice of Allowance dated May 9, 2018 for U.S. Appl. No. 15/053,232.
Notice of Allowance dated Mar. 13, 2020 for U.S. Appl. No. 14/832,422.
Office Action dated Feb. 20, 2020 for U.S. Appl. No. 15/806,020.
Office Action dated Mar. 25, 2020 for U.S. Appl. No. 14/081,715.
Office Action dated Apr. 6, 2020 for U.S. Appl. No. 13/827,790.
Office Action dated Jul. 11, 2019 for U.S. Appl. No. 14/081,715.
Office Action dated Aug. 7, 2019 for U.S. Appl. No. 15/806,020.
Notice of Allowance dated Jan. 30, 2020 for U.S. Appl. No. 14/152,590.
Notice of Allowance dated Feb. 6, 2020 for U.S. Appl. No. 13/360,444.
Office Action dated Jul. 30, 2020 for U.S. Appl. No. 15/806,020.

* cited by examiner

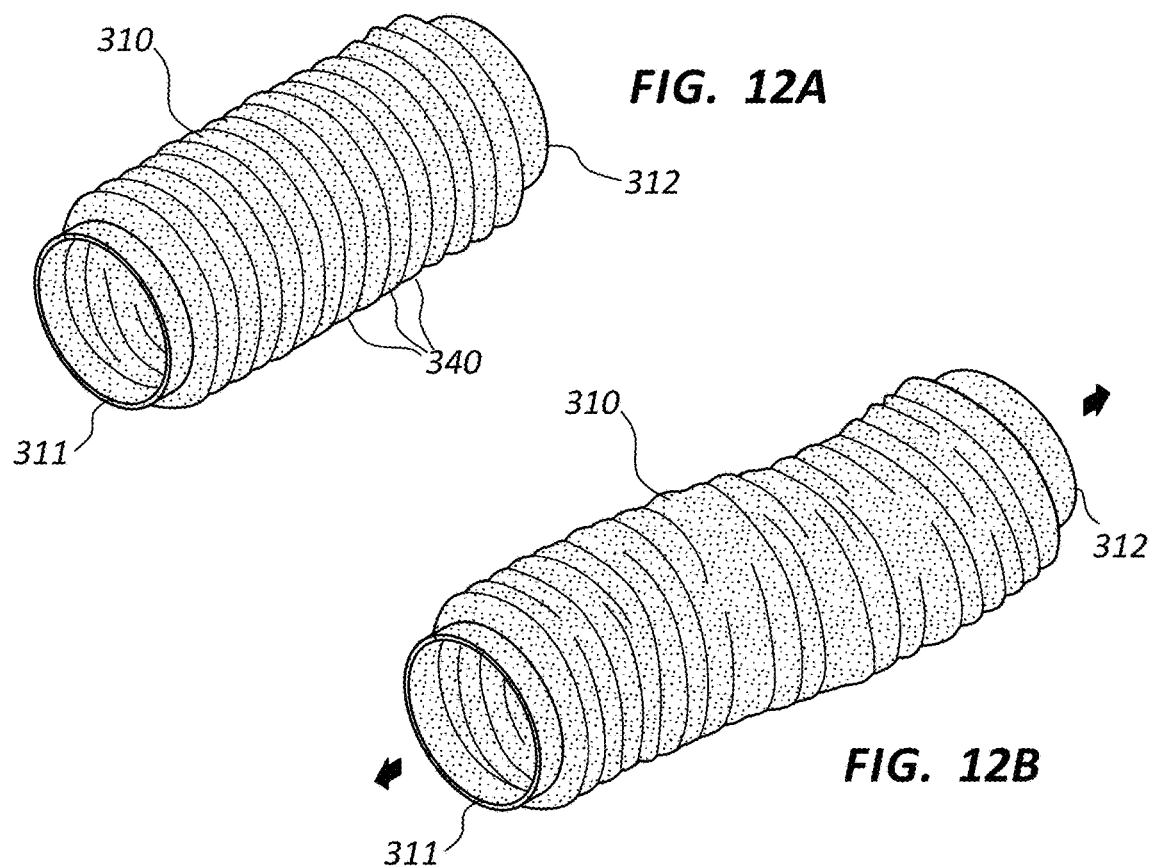
FIG. 12A
FIG. 12B
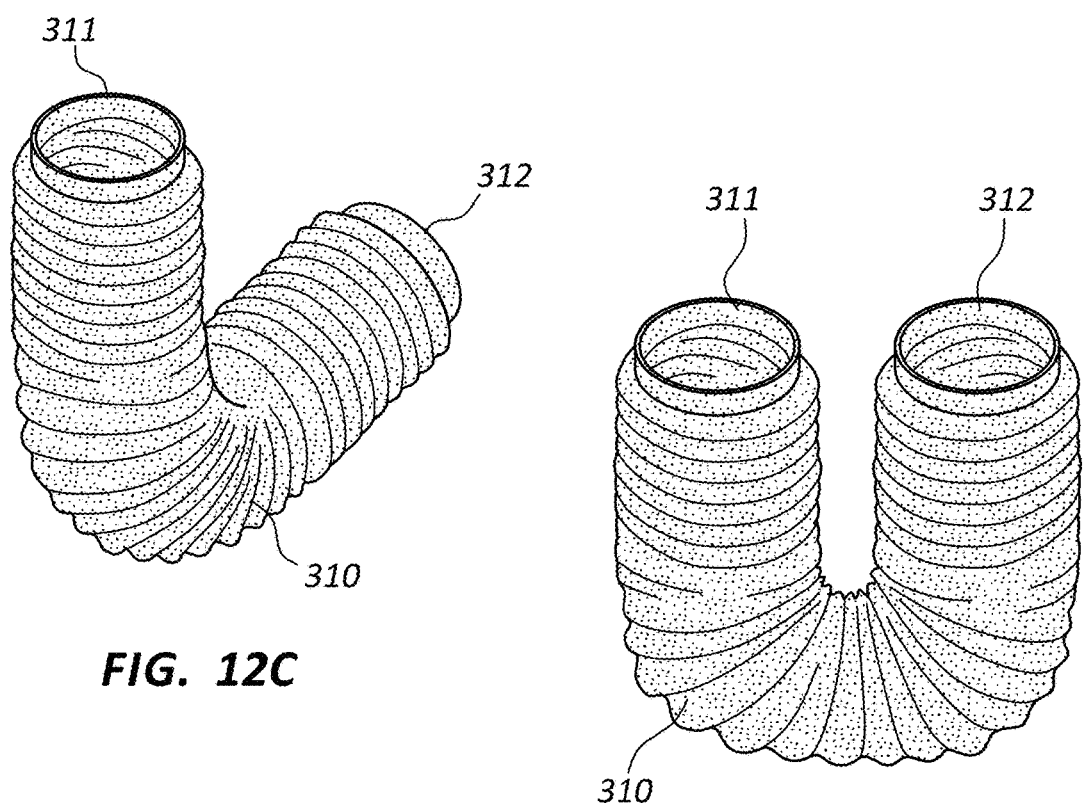
FIG. 12C
FIG. 12D

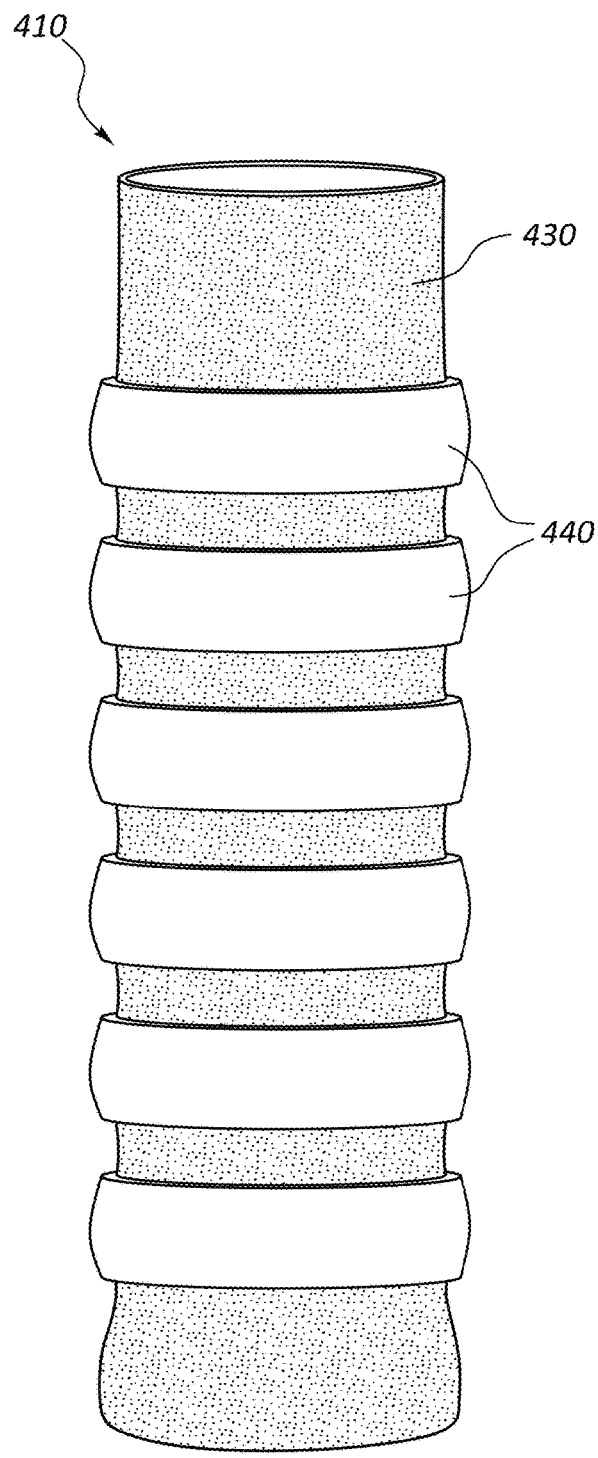 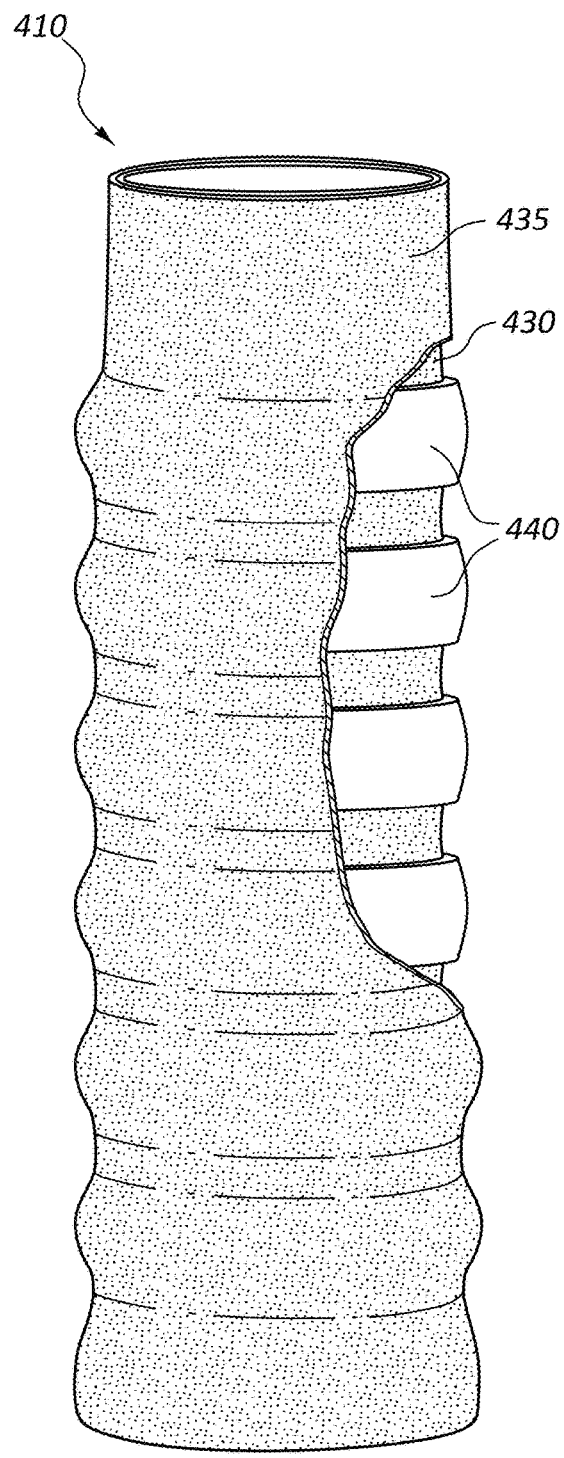
FIG. 14A  FIG. 14B

SERIALLY DEPOSITED FIBER MATERIALS AND ASSOCIATED DEVICES AND METHODS

RELATED APPLICATIONS

This application claims priority to both U.S. Provisional Application No. 61/780,646 filed on Mar. 13, 2013 and titled "Serially Deposited Fiber Materials and Associated Methods" and U.S. Provisional Application No. 61/847,875 filed on Jul. 18, 2013 and titled "Serially Deposited Fiber Materials and Associated Devices and Methods." Both of these applications are hereby incorporated by reference in their entirety.

TECHNICAL FIELD

The present disclosure relates generally to medical appliances, material, and structures comprising serially deposited fibers. These fibers may comprise polymeric fibers that may be deposited by rotational spinning and/or electrospinning, for example. The disclosure further relates to methods and processes for configuring the properties of the fibers and/or manufacture of structures fully or partially comprised of such fibers. In some embodiments, the polymeric fibers are used in implantable devices.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying figures in which:

FIG. 12A is a perspective view of a corrugated tube in a first configuration.

FIG. 12B is a perspective view of the corrugated tube of FIG. 12A in a second configuration.

FIG. 12C is a perspective view of the corrugated tube of FIG. 12A in a third configuration.

FIG. 12D is a perspective view of the corrugated tube of FIG. 12A in a fourth configuration.

FIG. 14A is a front view of a tube with reinforcing rings.

FIG. 14B is a front view of the tube of FIG. 14A with a layer disposed over the rings.

DETAILED DESCRIPTION

Figure 1A:
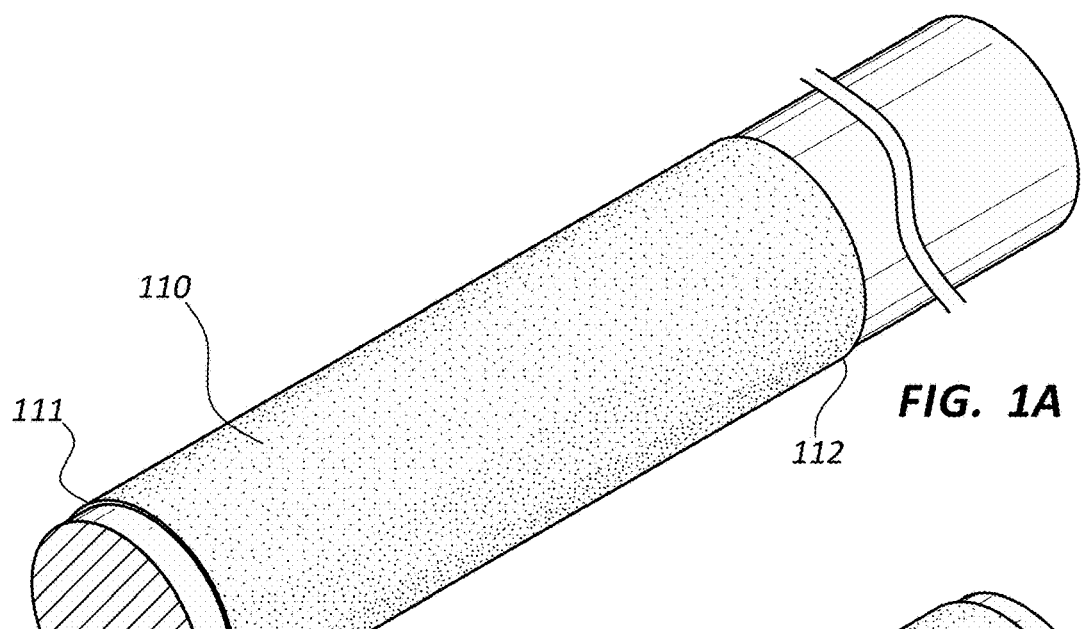
FIG. 1A is a perspective view of a membrane disposed on a mandrel.

Various structures, including medical appliances and related components, may comprise serially deposited fibers. Serially deposited fibers may comprise polymeric fibers, ceramic fibers, and/or other materials. In some embodiments, soft or fluidic materials are deposited in elongate strands or fibers on a collector or substrate. After these fibers are deposited, the shape or structure of the mat or lattice of fibers may be set by, for example, hardening of the material of the fibers. For example, polymeric materials may be deposited as fibers in the form of a polymeric dispersion and then sintered to remove the solvent component of the dispersion and to set the structure of the polymeric fibers. Similarly, polymeric materials may be serially deposited as fibers while the material is in a heated or molten state. Cooling of the collected fibers may tend to set the structure of the mat or lattice of fibers. The fibers comprising these mats or lattices may generally be on a micro scale (fibers which are between one micron and one millimeter in diameter) and/or generally on a nano scale (fibers which are smaller than one micron in diameter).

Serially deposited fiber mats or lattices refer to structures composed at least partially of fibers successively deposited on a collector, on a substrate, on a base material, and/or on previously deposited fibers. In some instances the fibers may be randomly disposed, while in other embodiments the alignment or orientation of the fibers may be somewhat controlled or follow a general trend or pattern. Regardless of any pattern or degree of fiber alignment, because the fibers are deposited on the collector, substrate, base material, and/or previously deposited fibers, the fibers are not woven, but rather serially deposited. Because such fibers are configured to create a variety of structures, as used herein, the terms "mat" and "lattice" are intended to be broadly construed as referring to any such structure, including tubes, spheres, sheets, and so on. Furthermore, the term "membrane" as used herein refers to any structure comprising serially deposited fibers having a thickness which is smaller than at least one other dimension of the membrane. Examples of membranes include, but are not limited to, serially deposited fiber mats or lattices forming sheets, strips, tubes, spheres, covers, layers, and so forth.

Rotational spinning is one example of how a material may be serially deposited as fibers. One embodiment of a rotational spinning process comprises loading a polymer solution or dispersion into a cup or spinneret configured with orifices on the outside circumference of the spinneret. The spinneret is then rotated, causing (through a combination of centrifugal and hydrostatic forces, for example) the flowable material within the spinneret to be expelled from the orifices. The material may then form a "jet" or "stream" extending from the orifice, with drag forces tending to cause the stream of material to elongate into a small diameter fiber. The fibers may then be deposited on a collection apparatus, a substrate, or other fibers. Once collected, the fibers may be dried, cooled, sintered, or otherwise processed to set the structure or otherwise harden the fiber mat. For example, polymeric fibers rotational spun from a dispersion may be sintered to remove solvents, fiberizing agents, or other materials as well as to set the structure of the mat. In one embodiment, for instance, an aqueous polytetrafluoroethylene (PTFE) dispersion may be mixed with polyethylene oxide (PEO) (as a fiberizing agent) and water (as a solvent for the PEO), and the mixture rotational spun. Sintering by heating the collected fibers may set the PTFE structure, evaporate off the water, and sublimate the PEO. Exemplary methods and systems for rotational spinning can be found in U.S. patent application Ser. No. 13/742,025, filed on Jan. 15, 2013, and titled "Rotational Spun Material Covered Medical Appliances and Methods of Manufacture," which is herein incorporated by reference in its entirety.

Electrospinning is another embodiment of how a material may be serially deposited as fibers. One embodiment of an electrospinning process comprises loading a polymer solution or dispersion into a syringe coupled to a syringe pump. The material is forced out of the syringe by the pump in the presence of an electric field. The material forced from the syringe may elongate into fibers that are then deposited on a grounded collection apparatus, such as a collector or substrate. The system may be configured such that the material forced from the syringe is electrostatically charged, and thus attracted to the grounded collection apparatus. As with rotational spinning, once collected, the fibers may be dried, cooled, sintered, or otherwise processed to set the structure or otherwise harden the fiber mat. For example, polymeric fibers electrospun from a dispersion may be sintered to remove solvents, fiberizing agents, or other materials as well as to set the structure of the mat. As in rotational spinning, one embodiment of electrospinning comprises electrospinning an aqueous PTFE dispersion mixed with PEO and water (as a solvent for the PEO). Sintering by heating the collected fibers may set the PTFE structure, evaporate off the water, and sublimate the PEO. Exemplary methods and systems for electrospinning medical devices can be found in U.S. Provisional Patent Application No. 61/703,037, filed on Sep. 19, 2012, and titled "Electrospun Material Covered Medical Appliances and Methods of Manufacture," and U.S. patent application Ser. No. 13/360,444, filed on Jan. 27, 2012, and titled "Electrospun PTFE Coated Stent and Method of Use," both of which are hereby incorporated by reference in their entireties.

Rotational spinning and/or electrospinning may be utilized to create a variety of materials or structures comprising serially deposited fibers. The microstructure or nanostructure of such materials, as well as the porosity, permeability, material composition, rigidity, fiber alignment, and so forth, may be controlled or configured to promote biocompatibility or influence interactions between the material and cells or other biologic material. A variety of materials may be serially deposited through processes such as rotational spinning and electrospinning, for example, polymers, ceramics, metals, materials which may be melt-processed, or any other material having a soft or liquid form. A variety of materials may be serially deposited through rotational spinning or electrospinning while the material is in a solution, dispersion, molten or semi-molten form, and so forth. The present disclosure may be applicable to any material discussed herein being serially deposited as fibers onto any substrate or in any geometry discussed herein. Thus, examples of particular materials or structures given herein may be analogously applied to other materials and/or structures.

Rotational spinning, electrospinning, or other analogous processes may be used to create serially deposited fiber mats as disclosed herein. Throughout this disclosure, examples may be given of serially deposited fiber mats generally, or the examples may specify the process (such as rotational spinning or electrospinning) utilized to create the serially deposited fiber mat. It is within the scope of this disclosure to analogously apply any process for creating serially deposited fibers to any disclosure or example below, regardless of whether the disclosure specifically indicates a particular mat was formed according to a particular process.

Serially deposited fiber mats or lattices may be further processed after the fibers are deposited. For example, the fiber mat or lattice may subsequently be deformed, work-hardened, shape-set in a particular geometry, or otherwise processed. In one example, serially deposited structures may be stretched in one or more directions, in some instances while the mat is at an elevated temperature, such as when the material of the fibers is at its crystalline melt temperature. In some examples, stretching a fiber mat may tend to alter the degree to which fibers within the mat are aligned. A fiber mat may further be densified by heating and compressing portions of the mat. Various methods and systems for processing serially deposited fiber structures can be found in U.S. Provisional Patent Application No. 61/780,646, filed on Mar. 13, 2013, and titled "Serially Deposited Fiber Materials and Associated Methods," which is hereby incorporated by reference in its entirety.

Serially deposited fibers may be formed or configured with various characteristics. Various properties of a fiber mat or lattice, such as fiber size, pore size, permeability, fiber alignment, density, and so forth may be controlled during initial fabrication of the mat, post-processing, or both. It is within the scope of this disclosure to create serially deposited fiber mats as described below through any combination of fabrication steps and/or post-processing steps. For example, stretching a fiber mat after deposition (post-processing) and serially depositing a fiber mat onto a spinning mandrel or in the presence of electric fields or air currents to control deposition (fabrication steps) may both be used to control the degree to which fibers of a mat tend to be aligned. Any combination of any of these processes may be utilized to create a fiber mat with the characteristics described below. Similarly, any other fabrication or post-processing steps may be combined or utilized to control or affect other properties of a fiber mat.

Various medical appliances may comprise one or more layers of serially deposited fibers. For example, stent covers, stent grafts, grafts, patches, balloons, and other medical appliances may comprise one or more serially deposited fiber layers. In some embodiments, one or more serially deposited fiber layers may be present in a multilayered construct. Various layers may be configured with various properties. For example, a stent graft may be configured with one or more generally porous layers and one or more generally impermeable layers. In one embodiment, a porous layer may be configured to allow tissue growth on or into the layer, while an impermeable layer resists tissue growth and/or fluid passage across the layer.

Medical appliances of various constructs and configurations are within the scope of this disclosure. For example, a stent graft may be configured with an outer layer configured to permit tissue ingrowth into the outer layer. Such an outer layer may comprise serially deposited fibers having sufficient porosity or permeability to interact with biologic tissue to allow tissue growth on or in the outer layer. Without being bound by theory, an outer layer configured to permit tissue ingrowth may promote healing at the boundary between the outer layer and biologic tissue (i.e., a body lumen); may tend to anchor the stent graft upon implantation, reducing migration (through interaction of tissue and the outer layer); and may otherwise interact with biologic structures.

Similarly, a stent graft may be configured with an inner layer configured to allow tissue attachment or ingrowth along the inside diameter of a stent graft or other construct. Such a layer may be sufficiently porous to allow tissue (i.e., collagen, endothelial cells, and so forth) to attach to the inside diameter of a medical device. In some embodiments, the presence of endothelial cells on the inside diameter of a stent graft may facilitate laminar flow through the stent graft and otherwise promote healing.

Still further, constructs within the scope of this disclosure may further comprise one or more impermeable layers. Such layers may be configured to resist tissue growth into or through the layer and/or resist fluid passage across the layer (for example, blood flow across the layer). In some embodiments, a construct may be formed with more porous layers on one or both of the outside and inside diameters of a tubular medical appliance with an impermeable layer disposed between the inside and outside diameters. Impermeable layers may be configured to provide mechanical properties (e.g., strength, resistance to creep) to the construct while also creating a biologic impermeable zone.

In addition to constructs having impermeable layers disposed between more porous layers, constructs wherein an impermeable layer is disposed on an outside or inside surface are also within the scope of this disclosure. For example, a stent graft having a generally porous outside surface and an impermeable inside surface is within the scope of this disclosure. Such an appliance may be configured to promote tissue interaction and healing at an interface between the outside of the appliance and the body lumen, while resisting tissue growth on the inside surface of the stent graft. Such a design may allow for maximum tissue growth from the lumen into the outside layer of the stent graft (to provide maximum migration resistance) while still maintaining an impermeable layer to prevent blood leakage across the stent graft.

Impermeable layers may comprise layers of serially deposited fibers having low porosities and/or densified serially deposited fibers as well as layers or coatings other than serially deposited fibers (e.g., wrapped layers, spray coats, dipped coats, and so forth). Constructs comprising any combination of serially deposited layers and any combination of non-serially deposited layers are within the scope of this disclosure.

Serially deposited fiber mats may be configured with a variety of characteristics which may be related to the material properties of the mat. For example, as indicated above, a serially deposited fiber mat which exhibits fiber alignment may exhibit different properties (e.g., tensile strength) in the direction of fiber alignment. Characteristics such as fiber size and fiber density may affect the porosity of a fiber mat or the degree to which the mat is permeable to fluid passage. Further, such characteristics may influence the degree to which a mat is susceptible to ingrowth of tissue (into or through the mat) when the mat is implanted in a body. The disclosure below describes various characteristics of serially deposited fiber mats. The characteristics described below may be present in a serially deposited fiber mat produced by a serial depositing method and may apply to mats of any composition (polymeric, ceramic, etc.). Further, the characteristics and properties described below are not mutually exclusive. In other words, a fiber mat having a particular porosity or fiber diameter as disclosed below may also have a particular fiber alignment or any other characteristic as described below.

The components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluidic, and thermal interaction. Two components may be coupled to each other even though they are not in direct contact with each other. For example, two components may be coupled to each other through an intermediate component.

As used herein, references to heating a material "at" a particular temperature indicate that the material has been disposed within an environment which is at the target temperature. For example, placement of a material sample in an oven, the interior of the oven being set at a particular temperature, would constitute heating the material at that particular temperature. While disposed in a heated environment, the material may, but does not necessarily, reach the temperature of the environment.

Additionally, the term "about," as used herein in connection with temperature, is meant to indicate a range of ±5° C. around the given value. The term "about" used in connection with quantities or values indicates a range of ±5% around the value.

1. Heat and Stretch Processing of Serially Deposited Fiber Mats

Figure 1B:
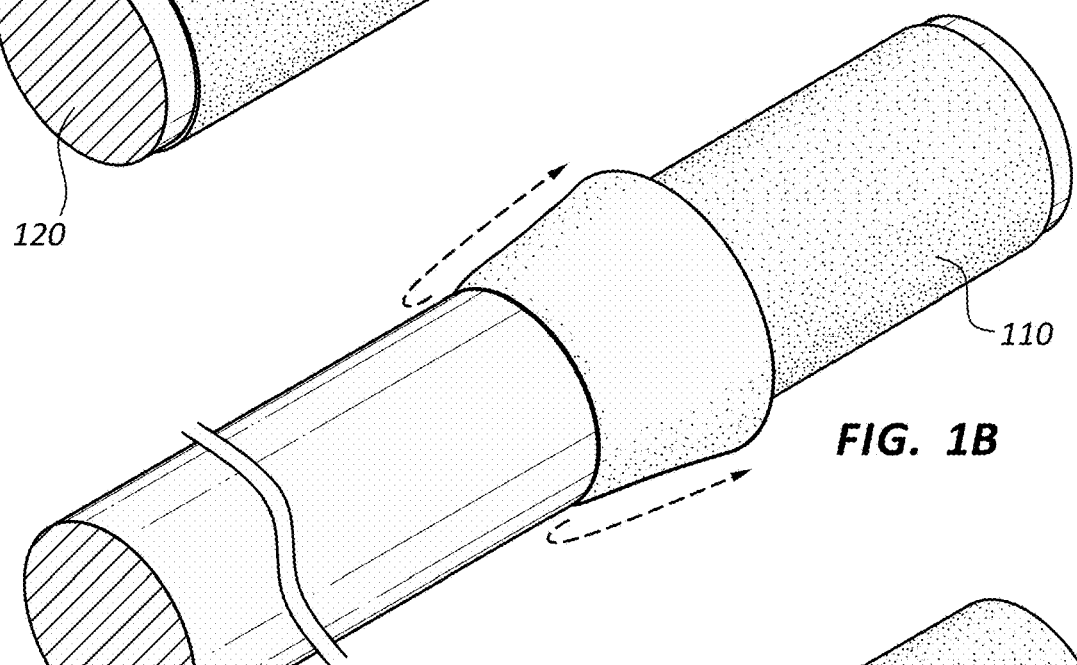
FIG. 1B is a perspective view of the membrane of FIG. 1A being removed from the mandrel.
Figure 1C:
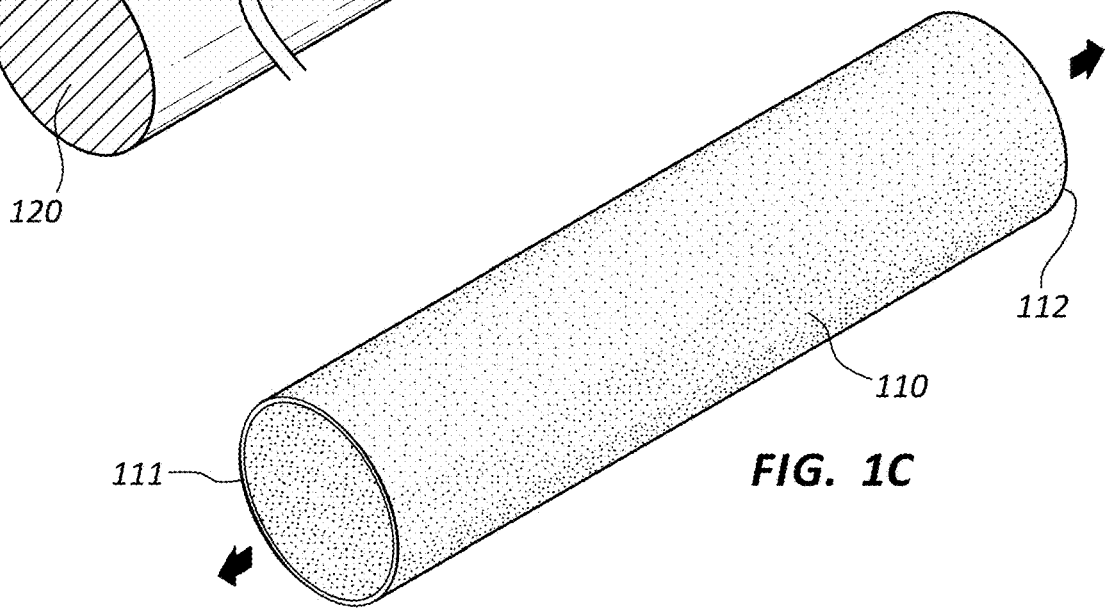
FIG. 1C is a perspective view of the membrane of FIG. 1A being stretched.

FIGS. 1A-1C schematically illustrate various steps of how a mat or lattice of serially deposited fibers may be processed by heating and/or stretching the mat or lattice. In the illustrated embodiments the mat of serially deposited fibers comprises a tubular membrane. In other embodiments the mat comprises a membrane in the form of a sheet, a sphere, a strip, or any other geometry. Additionally, any material which can be serially deposited as fibers may be processed as described in connection with these figures.

FIG. 1A is a perspective view of a membrane 110 disposed on a mandrel 120. In some embodiments the membrane 110 comprises a mat of sintered polymeric fibers. For example, a polymer dispersion such as a PTFE dispersion may be deposited on the mandrel 120 through rotational spinning or electrospinning. In the illustrated embodiment, the membrane 110 extends between a first end 111 and a second end 112.

FIG. 1B is a perspective view of the membrane 110 being removed from the mandrel 120. This may be done, for example, after the membrane 110 is serially deposited as fibers and sintered or otherwise structurally set. The membrane 110 may be removed by peeling the membrane 110 back off the mandrel 120, as shown in FIG. 1B, or by any other process, including slipping the membrane 110 off the mandrel 120 without folding it back.

The membrane 110 may then be heated at a particular temperature prior to further processing of the membrane 110. Temperatures at which materials may be heated prior to processing may vary depending on the material and depending on the desired characteristics of the material after processing. For example, a polymeric membrane may show more or less fiber alignment after processing depending on various factors, such as the temperature at which the materials are heated. In some instances the membrane 110 may be heated at a temperature at or above the crystalline melt point of the material comprising the membrane 110, though it is not necessary to heat the material as high as the crystalline melt temperature to stretch process the material.

In the case of polymeric materials which are sintered, the step of heating the membrane 110 may be performed as a separate and distinct step from sintering the membrane 110, or may be done as the same step. For example, it is within the scope of this disclosure to process a membrane 110 (as described in connection with FIG. 1C and other disclosure below) directly after sintering the membrane 110, while the membrane is at an elevated temperature due to the sintering process. It is likewise within the scope of this disclosure to obtain a previously sintered membrane 110 which may have been previously cooled to ambient temperature, then heat the membrane 110 as part of a heating and stretching process.

FIG. 1C is a perspective view of the membrane 110 being processed by stretching the membrane 110. Specifically, as shown by the arrows near the first 111 and second 112 ends of the membrane 110, in the illustrated embodiment, the membrane 110 is being stretched in the axial/longitudinal direction of the tube that forms the membrane 110. The membrane 110 may be so stretched by applying forces (for example in the direction of the arrows) to the membrane 110. Stretching the membrane 110 in the radial direction (or stretching it to increase the diameter of the tube) and stretching the membrane 110 in any other direction are also within the scope of this disclosure. Membranes or any other mat or lattice of serially deposited fibers may be stretched in any direction as part of a heating and stretching process. Further, it is within the scope of this disclosure to stretch a membrane in multiple directions, either simultaneously or as part of separate steps. For example, the membrane 110 of FIG. 1C may be stretched both axially and radially after the membrane 110 is initially heated, or the membrane may be stretched in these or other directions as part of distinct and separate steps. Additionally, the membrane 110 may be heated multiple times during such a process.

Various methods, modes, mechanisms, and processes may be utilized to apply forces to stretch materials. For example, force may be applied through mechanical, fluidic, electromagnetic, gravitational, and/or other mechanism or modes. In embodiments wherein force is applied through fluidic interaction, a pressurized gas or liquid could be used to generate the force while the material is at an elevated temperature. The fluid may be stagnant or recirculating. Further, the fluid may be used to heat and/or cool the material. For example, the liquid may be used to rapidly cool the material, locking the microstructure and geometry.

The membrane 110 may be held in a stretched position while the membrane 110 cools. For example, a membrane 110 may be heated at an elevated temperature prior to stretching, stretched while the membrane 110 is at an elevated temperature, then held in the stretched position while the membrane 110 cools to an ambient temperature. Depending on the process, when the membrane 110 is stretched, it may be at a temperature lower than the temperature at which it was heated, and it may or may not cool completely to the ambient temperature while the position is held.

Processing a mat or lattice of serially deposited fibers as described in connection with FIGS. 1A-1C may alter various material properties of the mat or lattice. For example, and as further outlined below, heating and stretching a fiber mat may increase the durability of the material, increase the smoothness of the material, increase handling characteristics, increase the tensile strength of the material, increase resistance to creep, or otherwise alter the material. Further, in some embodiments, heating and stretching the material tends to align a portion of the fibers which comprise the mat in the direction the material is stretched. This alignment of the microstructure and/or nanostructure of the material may impact microscale and/or nanoscale interactions between the mat and other structures, such as body cells. Fiber alignment may likewise alter the flow characteristics of a fluid flowing in contact with the mat. For example, a tubular membrane configured to accommodate blood flow may exhibit different flow conditions through the tube if the fibers are aligned by heating and stretching as compared to randomly disposed fibers.

As further outlined in the examples below, heating and stretching a mat may or may not tend to align the fibers in the direction the material is stretched. In some embodiments, the degree of fiber alignment may be related to the temperature at which the mat was heated prior to stretching. Still further, stretching a mat in multiple directions may tend to maintain random fiber disposition of a mat in embodiments wherein the original mat exhibited generally random fiber disposition.

Regardless of whether heating and stretching tend to align the fibers in the direction the mat was stretched, the mat may exhibit different properties in a stretched direction as compared to a non-stretched direction. For example, the mat may exhibit increased tensile strength and/or increased resistance to creep in the stretched direction while these properties may be generally unchanged or decreased in a non-stretched direction. Further, stretching may increase the porosity of a mat of serially deposited fibers. In some embodiments, stretching may increase the porosity of a mat by up to 10 times the original porosity, including up to eight times, up to six times, up to four times, and up to two times the original porosity. FIGS. 3 and 4, infra, visually illustrate how porosity may be affected by stretching. In some embodiments, a mat may be stretched while at room temperature to increase porosity.

Additionally, in some embodiments, a tubular membrane heated and stretched in the axial direction may exhibit greater tensile strength in the axial direction as compared to the properties of the membrane prior to heating and stretching. In this example, the tensile strength in the radial direction, however, may be similar to the tensile strength of the membrane in that direction prior to heating and stretching. Thus, the membrane may have similar properties in both these directions prior to heating and stretching, but may exhibit greater tensile strength in the axial direction after heating and stretching. In some embodiments, the tensile strength of the membrane is 150%-300% that of the membrane prior to heating and stretching in the direction of stretching. For example, the tensile strength of the membrane is at least 150%, at least 200%, at least 250% or at least 300% that of the membrane prior to heating and stretching in the direction of stretching. In some embodiments, a mat may exhibit decreased tensile strength or other changes in properties in a non-stretched direction disposed perpendicular to the direction of stretching, as compared to those properties prior to stretching.

In some embodiments, a material is stretched in multiple directions to increase strength or otherwise alter the properties in those directions. In other embodiments, heating and stretching change the properties in only one direction. For example, a tube may be configured to be bolstered against creep in the radial direction, without substantially affecting the material properties in the axial direction. Again, in some instances an increase in particular properties in a first direction is correlated with a decrease in one or more of the same properties in a second direction.

Additionally, materials having different properties in different directions may be combined to create a composite construct. As indicated above, serially deposited fiber mats may be heated and work-hardened by stretching to change the material properties of the mat and/or to tend to align the fibers of the mat. In one example, a composite construct comprising at least one layer of axially stretched material and at least one layer of radially stretched material may exhibit increased strength in both directions. Various layers having various properties may be combined to tailor the properties of the resultant construct. It is within the scope of this disclosure to bond any adjacent layers of any construct through various processes, including use of tie layers disposed between layers and bonded to each layer, heating adjacent layers to create fiber entanglement, use of adhesives, and so forth. Fluorinated ethylene propylene (FEP) may be used as a tie layer in some embodiments, including as a tie layer between serially deposited layers of PTFE. Further expanded PTFE may be used as a tie layer in some embodiments. One embodiment of a composite tube can be created by helically or cigar wrapping a tube of serially deposited fibers (unstretched) with a film of heat and stretch processed material, creating a porous luminal layer and a strong creep-resistant reinforcement layer. Additional layers (such as an impervious layer and/or a porous abluminal layer) may be added to the construct as well. Each layer may be configured to optimize a physiologic interaction, for example.

Multilayered constructs may further comprise reinforcing structures, such as metal scaffolds or frames. In some embodiments a reinforcing structure may comprise one of Nitinol, stainless steel, chromium cobalt (MP35N), or titanium. Any layer of a construct may be configured to be a blood contacting layer. Blood contacting layers may be configured to interact with the blood or other biological elements and may be configured with certain flow characteristics at the blood interface. Further, any layer of a multilayered construct may be configured to be impermeable to tissue or fluid migration. For example, an impermeable tie layer may be disposed between porous inner and outer layers of a construct. Multilayered constructs comprising any number of layers are within the scope of this disclosure. For example, constructs having at least one, two, three, four, five, six, seven, eight, nine, ten or more layers or more are within the scope of this disclosure. Any layer or material described herein may comprise a layer of a multilayered construct, including, for example, serially deposited fiber layers, reinforcing layers comprising reinforcing structures including frames or scaffolds, layers of heat or stretch processed material, layers set in particular geometries, tie layers, impervious or impermeable layers, porous layers, layers configured to be blood contacting, layers configured to resist creep, wrapped film layers, dip-coated layers, and so forth.

Single layer devices or multilayered constructs within the scope of this disclosure may comprise tubes, grafts, stents, stent grafts, vascular grafts, patches, prosthetics, or any other medical appliance. Medical appliances configured for oral surgery and/or plastic surgery are also within the scope of this disclosure. Further, multilayered constructs wherein no layer comprises expanded PTFE (ePTFE) are also within the scope of this disclosure.

Figure 2A:
FIG. 2A is a Scanning Electron Micrograph (SEM) (950× magnification) of a portion of an axially/longitudinally stretched rotational spun tube.
Figure 2B:
FIG. 2B is an SEM (950× magnification) of a portion of a radially stretched rotational spun tube.

FIGS. 2A and 2B are Scanning Electron Micrographs (SEMs), both at 950× magnification, of rotational spun tubular membranes; the membrane of FIG. 2A was stretched in the axial direction of the tubular membrane while the membrane of FIG. 2B was stretched in the radial direction. In both instances, the membranes were heated and stretched such that the membranes exhibited increased fiber alignment in the direction of stretching. Both membranes were manufactured with generally random fiber disposition while both FIGS. 2A and 2B reflect observable fiber alignment. Further, both membranes exhibited greater strength in the stretched direction as opposed to a non-stretched direction oriented perpendicular to the stretched direction. Further, the membranes exhibited greater elasticity or "spring" in the non-stretched direction oriented perpendicular to the stretched direction. It was observed that these samples exhibited increased strength in the direction of fiber alignment and decreased strength in the direction perpendicular to fiber alignment.

Heating and stretching a mat or lattice of serially deposited fibers may tend to decrease the thickness of the mat or lattice. For example, a tubular mat stretched in the range from 200% to 450% may exhibit a decrease in material thickness of between 10% and 90%, including from 20% to 80% and from 40% to 60%. Embodiments within these ranges did not exhibit holes or defects from the stretching process, and the overall surface quality of the material was maintained after stretching. Further, these ranges are intended to correlate the degree of stretching and the decrease in material thickness, not to constitute upper or lower bounds. Materials may be stretched further than the given range to further decrease the material thickness, for instance. Example 1.8, infra, includes specific examples of material thicknesses after heat and stretch processing.

As stated above, it is within the scope of this disclosure to heat and stretch various serially deposited fiber mats comprising various materials. Many of the examples discussed below refer particularly to PTFE fiber mats which have been processed in a variety of ways. These examples, or any other example referencing PTFE, may analogously apply to other materials as well. Specific temperatures for heating or otherwise processing a material may be analogously applied to other materials by considering the material properties (such as melting point) of such materials and analogizing to the examples below.

Unless otherwise noted, the PTFE fiber mats discussed in connection with the following examples comprise fiber mats created by rotational spinning a PTFE dispersion onto a collector. The mats were then sintered at 385° C. to remove solvents, water, and fiberizing agents, and/or to set the structure of the mat. Though the mats recited in particular examples may be rotational spun, it is within the scope of this disclosure to process electrospun mats as described below.

Generally, serially deposited PTFE fiber mats may be heated at temperatures between about 65° C. and about 400° C. while heating and stretching the mats. For example, serially deposited PTFE fiber mats may be heated at temperatures above about 65° C., above about 100° C., above about 150° C., above about 200° C., above about 250° C., above about 300° C., above about 350° C., above about 370° C., and above about 385° C. Additionally, serially deposited PTFE fiber mats may be stretched at room temperature (22° C.) without heating.

Serially deposited PTFE mats may be stretched from 150% to 500% of the initial length of the mat in the direction of stretching, including stretching mats to between 200% and 350%, between 250% and 300%, and between 300% and 500% of the original length of the mats in the direction of stretching. The amount of length change may be related to the temperature at which the mat is heated, the force applied when the mat is stretched, the original thickness of the mat, and the rate at which the mat is stretched. In the examples below, some test materials were stretched to 425% or more of their initial length; however, this did not appear to be an upper bound. Without being bound by theory, the examples suggest the material may be stretched further without failure.

Processing serially deposited fiber mats or lattices through heating and stretching may impact various properties of the mats. Tensile strength, resistance to creep, elasticity, and so forth may all be impacted. In some embodiments, processed mats are used as layers of multilayered constructs to provide particular properties in a particular direction.

As further detailed in Examples 1.1-1.7 below, the temperature at which the mats of serially disposed PTFE fibers were heated was observed to affect the tendency of the fibers of the mats to align after the mats were stretched. As detailed below, materials were heated at temperatures well below the crystalline melt temperature of PTFE (325° C.) and well above this point. Though all mats appeared to exhibit changed properties, higher temperatures generally correlated with increased fiber alignment. Without being bound by theory, mats which were heated at or above 370° C. exhibited more fiber alignment than mats heated at temperatures lower than 370° C. Additionally, as detailed in Example 1.9 below, it was observed that tensile strength increased after fiber mats were heated and stretched, whether or not the mat was heated at 370° C. or more. The amount of the increase in tensile strength was observed to be affected by the temperature at which the mat was heated and the amount the material was stretched.

Various heating and stretching processes were tested in Examples 1.1-1.9 below. For Examples 1.1-1.5, tubular membranes comprising rotational spun PTFE fibers were prepared by rotational spinning a PTFE dispersion at 8000 RPM onto a horizontal rotating mandrel, the mandrel rotating at 1500 RPM. The membranes were rotational spun for 6 minutes then sintered by heating the membranes at 385° C. for 15 minutes. The membranes manufactured under these parameters exhibit generally random fiber disposition. SEMs were prepared for certain examples, as noted. In the case of tubular samples, the SEMs were taken of the inside diameter of the membrane. The membranes prepared for Examples 1.6-1.7 were prepared by a similar process to that of Examples 1.1-1.5, with specific differences noted in these examples. The process for manufacturing the membranes of Examples 1.8-1.9 is described in these examples.

Example 1.1

A fully sintered tubular membrane was heated in an oven at 300° C. for 6 minutes. The membrane had an initial length of 40 mm. After heating, the membrane was manually stretched in the axial direction by gripping the ends of the membrane and stretching. The stretching was done immediately, while the membrane was still at an elevated temperature. Immediately after stretching, the ends of the membrane were held at a fixed length, while the membrane remained under tension, until the membrane cooled to near room temperature. Upon cooling, it was observed that the membrane exhibited greater tensile strength in the axial (stretched) direction than in the radial direction.

Example 1.2

A fully sintered tubular membrane was heated in an oven at 300° C. for 6 minutes. The membrane had an initial length of 128 mm, an initial wall thickness of 0.44 mm, and an initial weight of 1.464 g. After heating, the membrane was immediately stretched while still at an elevated temperature. The membrane was stretched at a moderate rate to an end length of 280 mm, or to a final length which was 219% of the original length. The post-processing weight was measured as 1.462 g.

Figure 3B:
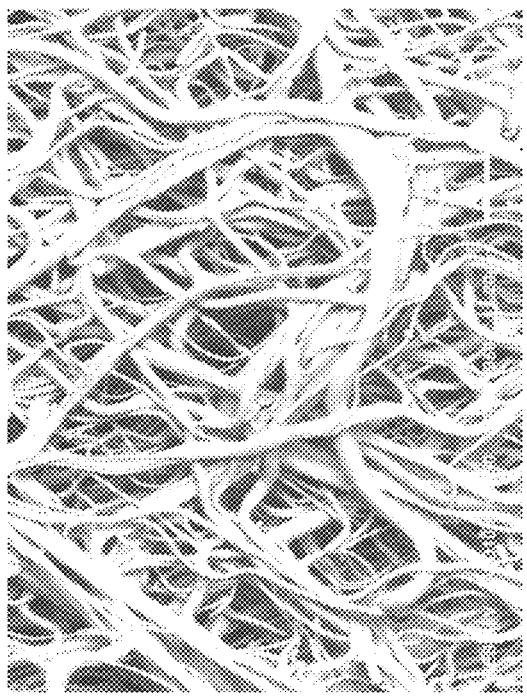
FIG. 3B is an SEM (950× magnification) of the portion of the rotational spun fiber mat of FIG. 3A.
Figure 3D:
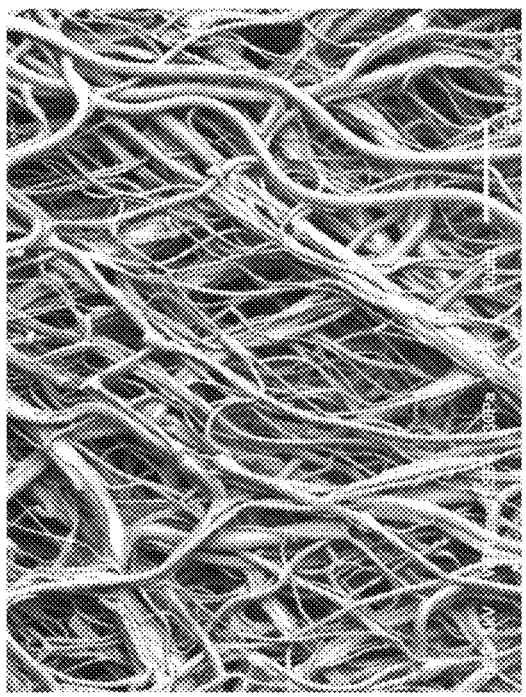
FIG. 3D is an SEM (950× magnification) of the portion of the rotational spun fiber mat of FIG. 3C.
Figure 3A:
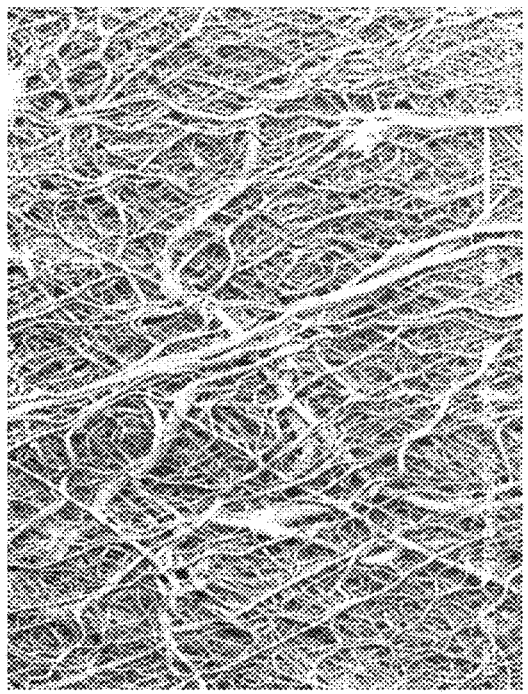
FIG. 3A is an SEM (170× magnification) of a first portion of a rotational spun fiber mat.
Figure 3C:
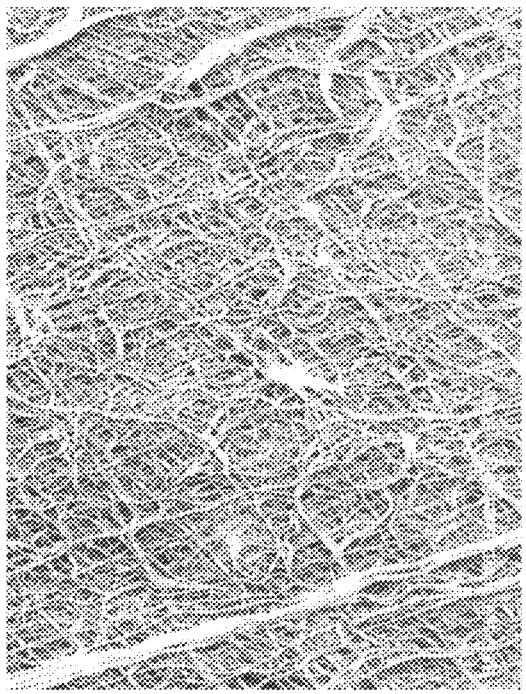
FIG. 3C is an SEM (170× magnification) of a second portion of the rotational spun fiber mat of FIG. 3A.

It was observed that the heated and stretched membrane exhibited greater strength in the axial (stretched) direction as compared to the radial direction. SEMs of the heated and stretched membrane were prepared. FIGS. 3A and 3C are SEMs of the processed membrane at 170× magnification, and FIGS. 3B and 3D are SEMs of the processed membrane at 950× magnification. FIGS. 3A and 3B are images of the same general region at different magnifications, while FIGS. 3C and 3D are of the same general region (which is different from the region imaged in FIGS. 3A and 3B) at different magnifications. It was observed from the SEMs that the processed membrane retained generally random fiber disposition, though the fibers appeared to be more aligned than expected when compared to a membrane that had not been stretch processed. Again, it was observed that the membrane exhibited greater strength in the stretched direction, as compared to the radial direction, even without significant fiber alignment in the stretched direction.

Example 1.3

A fully sintered tubular membrane was heated in an oven at 250° C. for 6 minutes. The membrane had an initial length of 120 mm, an initial wall thickness of 0.40 mm, and an initial weight of 1.294 g. After heating, the membrane was immediately stretched while still at an elevated temperature. The membrane was stretched at an increased rate (as compared to the membrane of Example 1.2) to an end length of 290 mm, or to a final length which was 242% of the original length. The post-processing weight was measured as 1.286 g.

Figure 4B:
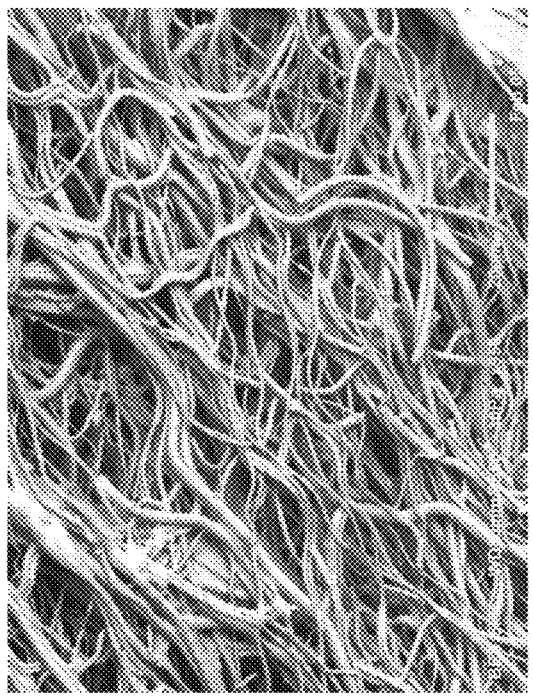
FIG. 4B is an SEM (950× magnification) of the portion of the rotational spun fiber mat of FIG. 4A.
Figure 4D:
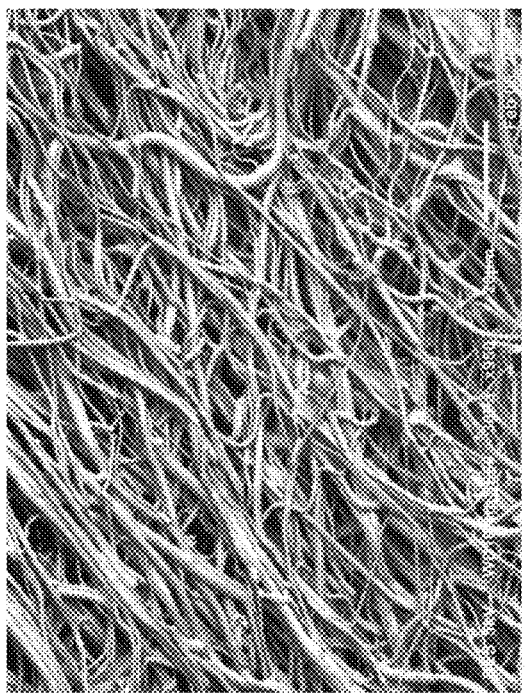
FIG. 4D is an SEM (950× magnification) of the portion of the rotational spun fiber mat of FIG. 4C.
Figure 4A:
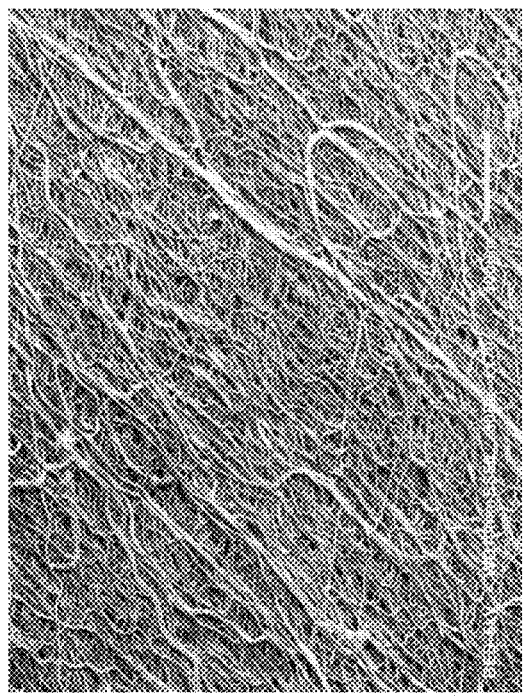
FIG. 4A is an SEM (170× magnification) of a first portion of a rotational spun fiber mat.
Figure 4C:
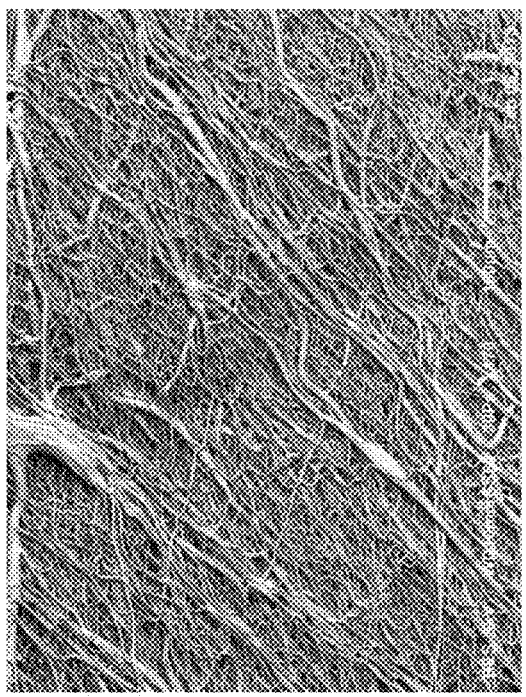
FIG. 4C is an SEM (170× magnification) of a second portion of the rotational spun fiber mat of FIG. 4A.

It was observed that the heated and stretched membrane exhibited greater strength in the axial (stretched) direction as compared to the radial direction. SEMs of the heated and stretched membrane were prepared. FIGS. 4A and 4C are SEMs of the processed membrane at 170× magnification, and FIGS. 4B and 4D are SEMs of the processed membrane at 950× magnification. FIGS. 4A and 4B are images of the same general region at different magnifications, while FIGS. 4C and 4D are of the same general region (which is different from the region imaged in FIGS. 4A and 4B) at different magnifications. It was observed from the SEMs that the processed membrane exhibited increased fiber alignment and increased porosity. It was observed that the rate of stretching increased the degree of fiber alignment.

Example 1.4

A fully sintered tubular membrane was heated in an oven at 250° C. for 6 minutes. The membrane had an initial length of 107 mm and an initial weight of 0.912 g. After heating, the membrane was immediately stretched while still at an elevated temperature. The membrane was stretched to an end length of 250 mm, or to a final length which was 234% of the original length. The post-processing weight was measured as 0.905 g.

It was observed that the heated and stretched membrane exhibited greater strength in the axial (stretched) direction as compared to the radial direction and that the material exhibited increased porosity. Further, it was observed in this and similar tests that the stretching process tended to naturally twist the tubular membrane. This twisting appears to be related to how the tubular membrane was placed in the oven and how it was gripped when pulled. In examples where the ends of a tubular membrane were fixed during heating, the membrane did not twist when pulled in tension.

Additionally, prior to heating, the membrane was marked along its length at 10 mm intervals. These intervals were measured again after the membrane was heated and stretched. It was observed that the increase in length was generally uniform along the length of the membrane, meaning the intervals generally each increased by the same amount.

Example 1.5

A fully sintered tubular membrane was heated in an oven at 385° C. for 6 minutes. The membrane had an initial length of 113 mm, an initial wall thickness of 0.33 mm, and an initial weight of 0.691 g. After heating, the membrane was immediately stretched while still at an elevated temperature. The membrane was stretched to an end length of 350 mm, or to a final length which was 310% of the original length. The processed membrane was measured to have a weight of 0.690 g.

Figure 5B:
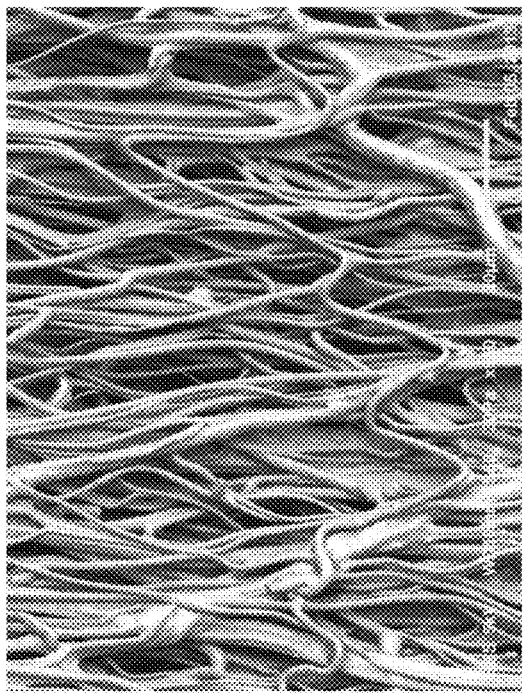
FIG. 5B is an SEM (950× magnification) of the portion of the rotational spun fiber mat of FIG. 5A.
Figure 5D:
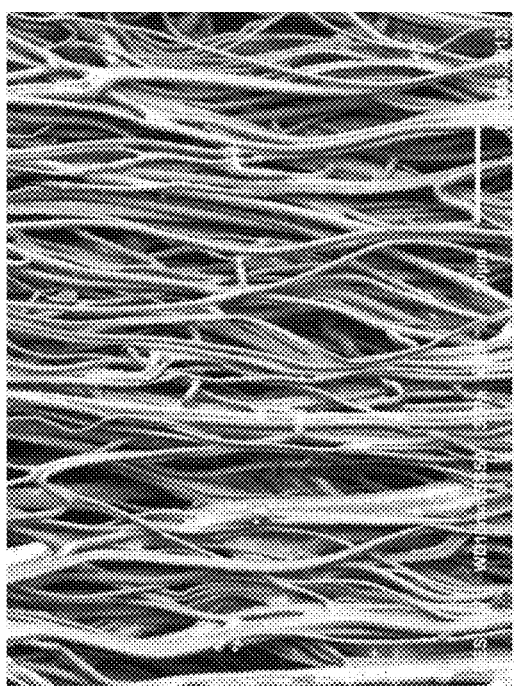
FIG. 5D is an SEM (950× magnification) of the portion of the rotational spun fiber mat of FIG. 5C.
Figure 5A:
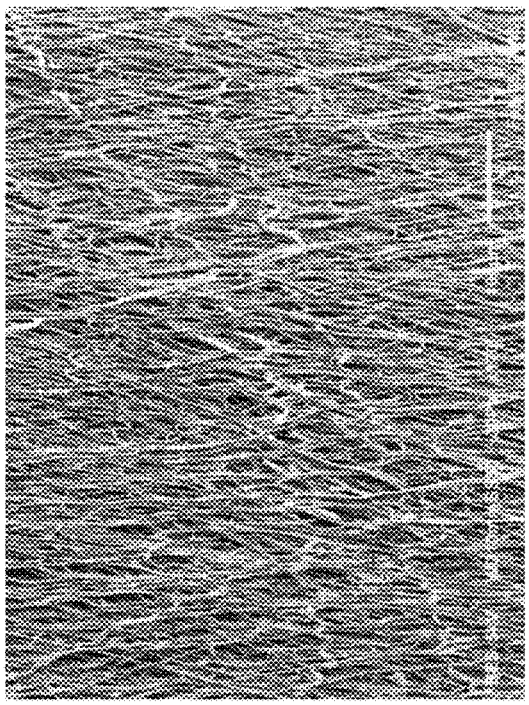
FIG. 5A is an SEM (170× magnification) of a first portion of a rotational spun fiber mat.
Figure 5C:
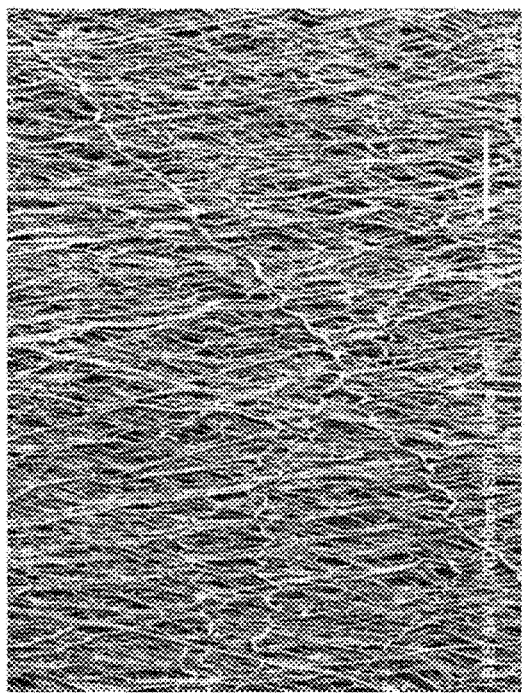
FIG. 5C is an SEM (170× magnification) of a second portion of the rotational spun fiber mat of FIG. 5A.

It was observed that the heated and stretched membrane exhibited greater strength in the axial (stretched) direction as compared to the radial direction. SEMs of the heated and stretched membrane were prepared. FIGS. 5A and 5C are SEMs of the processed membrane at 170× magnification, and FIGS. 5B and 5D are SEMs of the processed membrane at 950× magnification. FIGS. 5A and 5B are images of the same general region at different magnifications, while FIGS. 5C and 5D are of the same general region (which is different from the region imaged in FIGS. 5A and 5B) at different magnifications. It was observed from the SEMs that the processed membrane exhibited increased fiber alignment as compared to the previous examples and as compared to the expected disposition of the unprocessed membrane. Furthermore, some fibers disposed generally perpendicular to the direction of stretching appeared to exhibit a wavy or "zigzag" general disposition after stretching. It was thus observed that membranes heated at 385° C. exhibited greater fiber alignment than those heated at lower temperatures. It was further observed that this change in alignment was observed at temperatures above about 370° C. but not as pronounced at temperatures below this point.

Example 1.6

A membrane was rotational spun as generally described above; however, the membrane of this example was spun between two collector-ends, but not directly spun onto a mandrel or other collector. The resultant fibers thus "bridged" between the two collector-ends. The fibers were not initially sintered prior to heating as part of the heating and stretching process. Rather, the fibers were heated at 385° C. for 6 minutes to sinter the material, then immediately stretched while still at the elevated temperature. Thus, in this example, heating to sinter the material and heating to process the material were done as the same procedure.

Figure 6A:
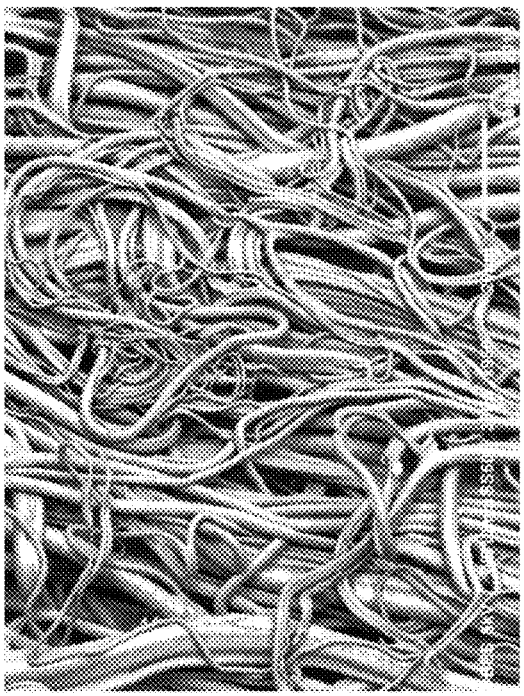
FIG. 6A is an SEM (170× magnification) of a first portion of a rotational spun fiber mat.
Figure 6B:
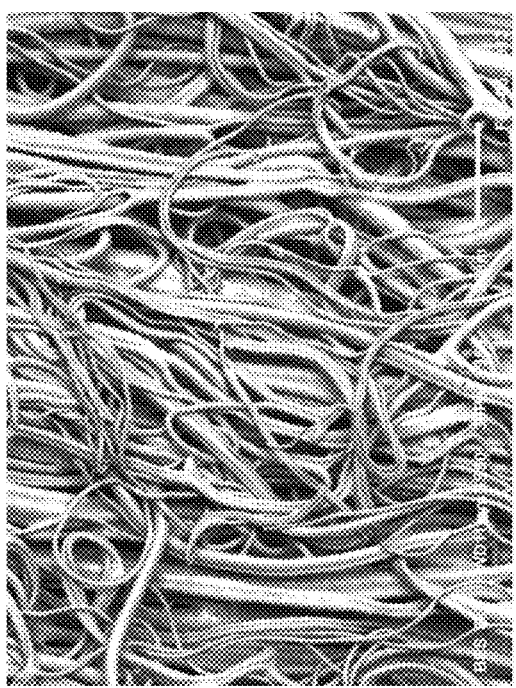
FIG. 6B is an SEM (950× magnification) of the portion of the rotational spun fiber mat of FIG. 6A.
Figure 6C:
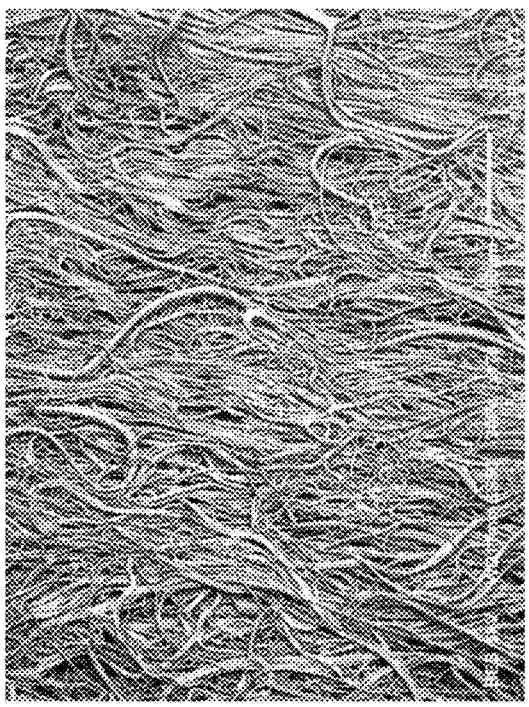
FIG. 6C is an SEM (170× magnification) of a second portion of the rotational spun fiber mat of FIG. 6A.
Figure 6D:
FIG. 6D is an SEM (950× magnification) of the portion of the rotational spun fiber mat of FIG. 6C.

The initially unsintered membrane was stretched without any notable difference in procedure or result as compared to the initially sintered membranes of Examples 1.1-1.5. The membrane exhibited similar properties, evaluated from a feel/tactile perspective, to the initially sintered then processed membranes. SEMs of the heated and stretched membrane were prepared. FIGS. 6A and 6C are SEMs of the processed membrane at 170× magnification, and FIGS. 6B and 6D are SEMs of the processed membrane at 950× magnification. FIGS. 6A and 6B are images of the same general region at different magnifications, while FIGS. 6C and 6D are of the same general region (which is different from the region imaged in FIGS. 6A and 6B) at different magnifications. It was further observed that the material was thinner after being stretched.

Example 1.7

A membrane was rotational spun onto a mandrel as generally described above; however, spun fibers were removed from the mandrel without sintering. The membrane was then manually twisted eight times around itself to entangle the fibers. The fibers were then heated at 385° C. for 6 minutes to sinter the material, then immediately stretched while still at the elevated temperature. Thus, in this example, heating to sinter the material and heating to process the material were done as the same procedure. After sintering of this twisted membrane, the PEO present in the dispersion turned black (whereas in other examples it evaporated from the membrane during sintering). Additionally, portions of the membrane constrained at the ends by clamps turned black and were observed to be brittle.

Figure 7B:
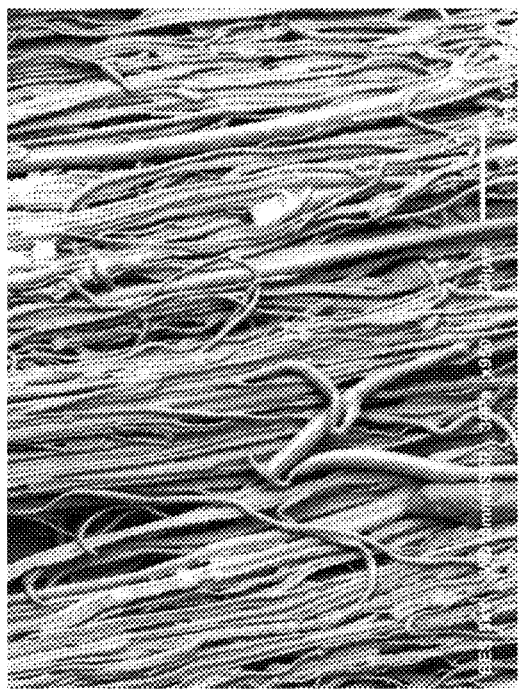
FIG. 7B is an SEM (950× magnification) of the portion of the rotational spun fiber mat of FIG. 7A.
Figure 7D:
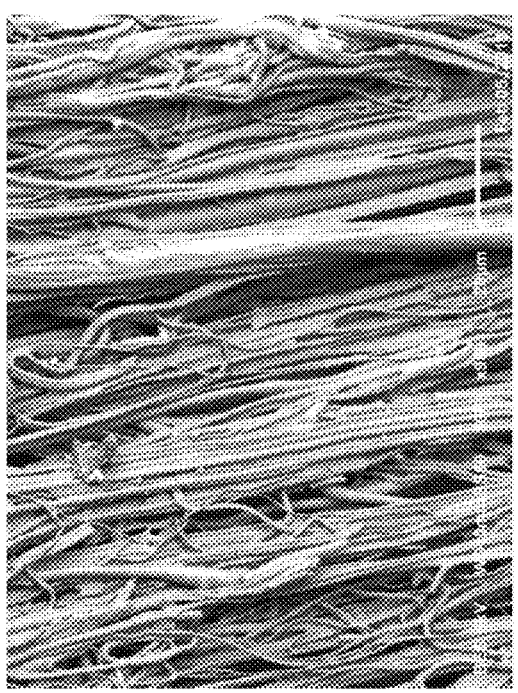
FIG. 7D is an SEM (950× magnification) of the portion of the rotational spun fiber mat of FIG. 7C.
Figure 7A:
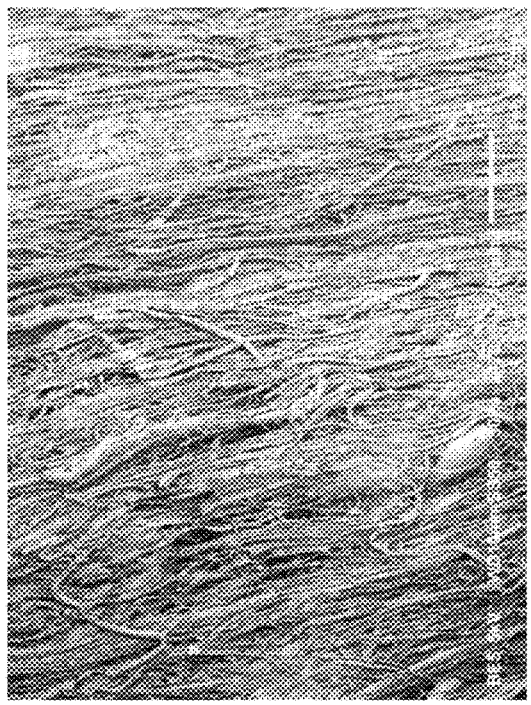
FIG. 7A is an SEM (170× magnification) of a first portion of a rotational spun fiber mat.
Figure 7C:
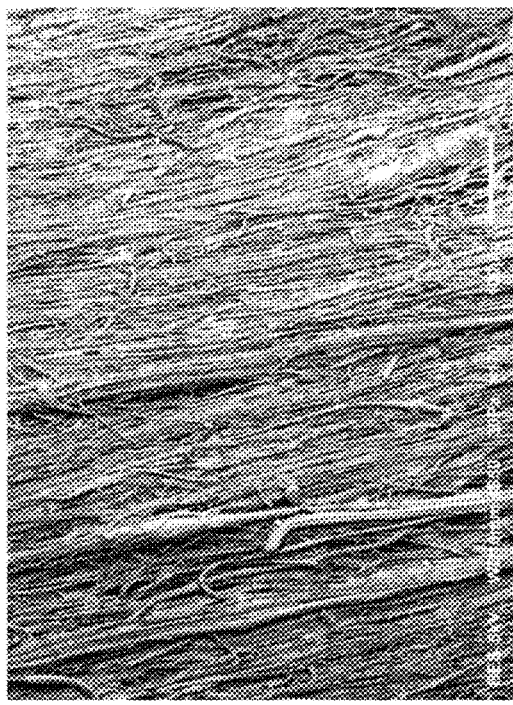
FIG. 7C is an SEM (170× magnification) of a second portion of the rotational spun fiber mat of FIG. 7A.

The membrane was stretched to 200% of its original length. SEMs of the heated and stretched membrane were prepared. FIGS. 7A and 7C are SEMs of the processed membrane at 170× magnification, and FIGS. 7B and 7D are SEMs of the processed membrane at 950× magnification. FIGS. 7A and 7B are images of the same general region at different magnifications, while FIGS. 7C and 7D are of the same general region (which is different from the region imaged in FIGS. 7A and 7B) at different magnifications. It was observed that the material was thinner after being stretched. It was also observed that the fibers exhibited a high degree of alignment, notwithstanding the initial twisting of the material.

Example 1.8

The change in material thickness for heated and stretched rotational spun PTFE membranes was analyzed as follows. Thirteen rotational spun tubular membranes were prepared. The initial lengths and wall thickness for each sample were recorded. The wall thickness was measured by flattening the tubular member and measuring the thickness (resulting in a measurement of two layers of the wall) and dividing by two. The membranes were heated at either 250° C., 370° C., or 385° C. and stretched. After stretching, the post-stretched lengths and thicknesses of the materials were measured and recorded.

Figure 8A:
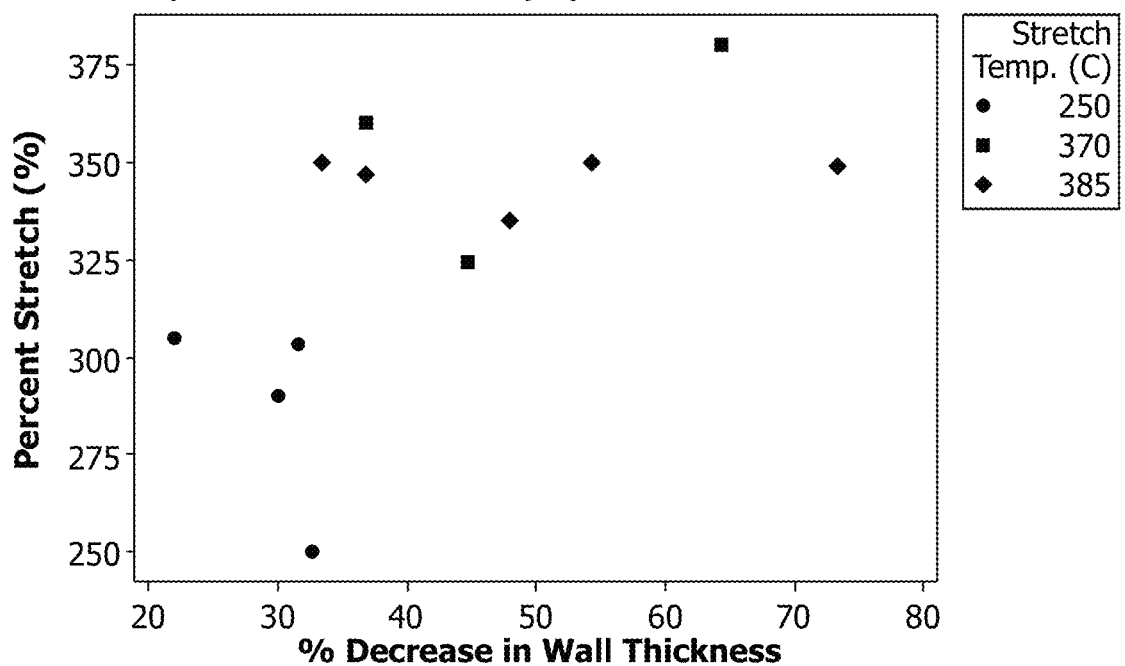
FIG. 8A is a graph plotting the percent stretch against the wall thickness decrease for materials stretched at various temperatures.
Figure 8B:
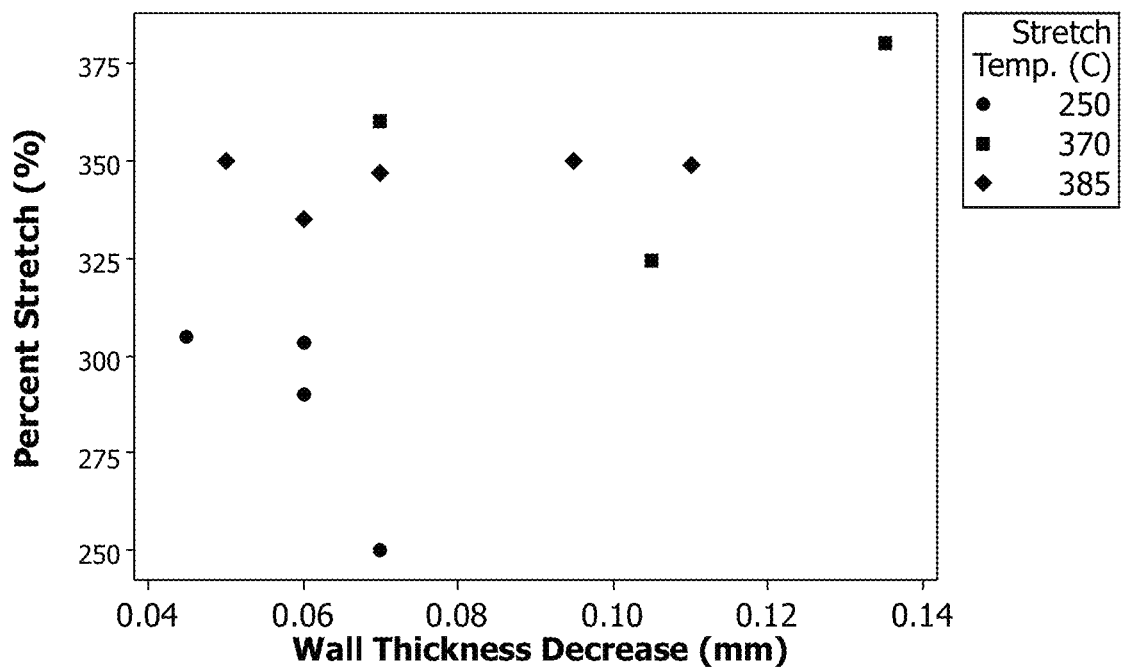
FIG. 8B is a graph plotting the percent stretch against the percent decrease in wall thickness for materials stretched at various temperatures.

FIGS. 8A and 8B summarize the results of this example. FIG. 8A is a graph plotting the percent stretch against the percent decrease in wall thickness for materials stretched at various temperatures. FIG. 8B is a graph plotting the percent stretch against the wall thickness decrease for materials stretched at various temperatures.

The membranes of this example exhibited percent decreases in wall thickness between 20% and 75%. The tested materials did not exhibit holes or defects from the stretching process, and the overall surface quality and feel of each material were maintained after stretching.

Example 1.9

The static mechanical behavior of heated and stretched rotational spun PTFE membranes was analyzed by tensile testing, as outlined in this example. Ten single-layer membrane samples were prepared by rotational spinning a PTFE/PEO dispersion at 7500 RPM onto 12-mm-diameter mandrels rotating at 1500 RPM. The mandrels were then placed in an oven, and the membranes were sintered at 385° C. for 20 minutes.

The membranes were post-processed by heating and stretching them at various temperatures. Specifically, the membranes were heated to 285° C., 370° C., or 385° C. and stretched while at temperature with tension maintained during cooling. The control membranes were not post-processed.

The membranes were tested by fixing 25-mm-long sections of the membrane tubes to the grips of an Instron 5944 machine, and the tensile force was measured using a 1 kN load cell. Elongation was measured using the internal LVDT sensor. The strain was calculated as the ratio of total elongation to area of the membrane. Membrane thickness was measured using a Mitutoyo digital thickness gauge. Membranes that failed at the Instron grips were excluded from the mechanical analysis.

Figure 9A:
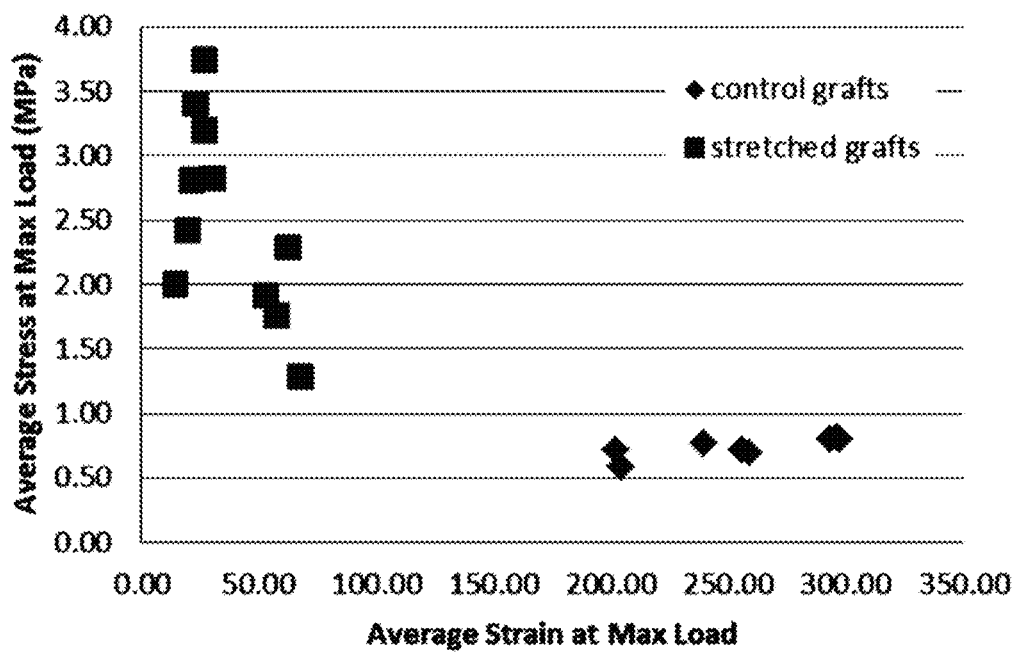
FIG. 9A is a graph showing the stress/strain ratios for various stretched and control grafts.
Figure 9B:
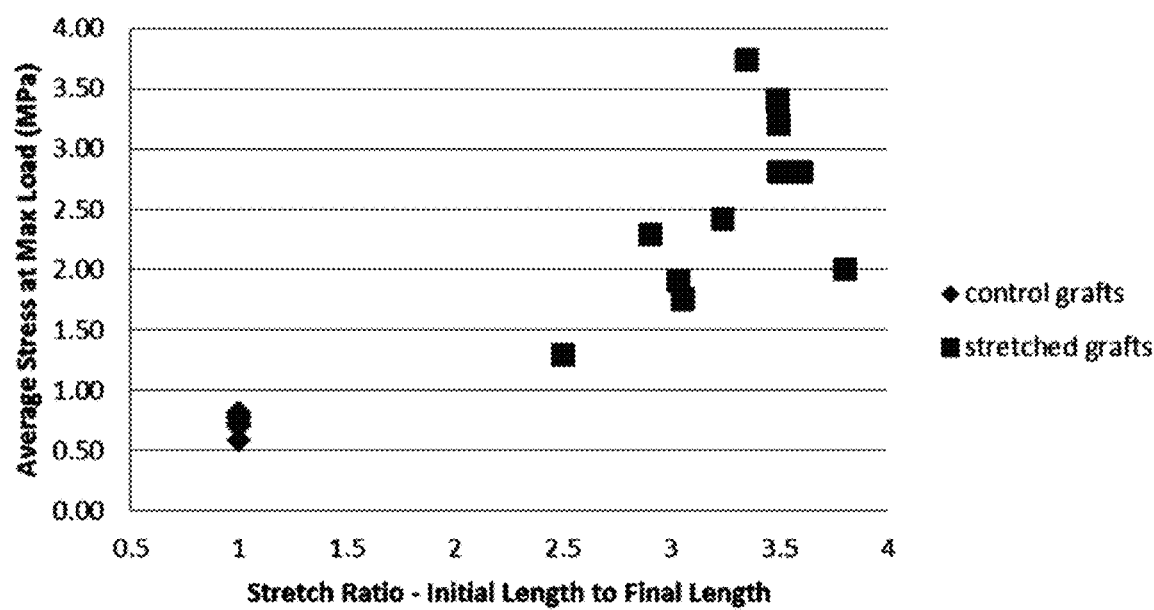
FIG. 9B is a graph showing the average stress at max load, plotted against the stretch ratio of each sample graft, for the grafts plotted in FIG. 9A.
Figure 10A:
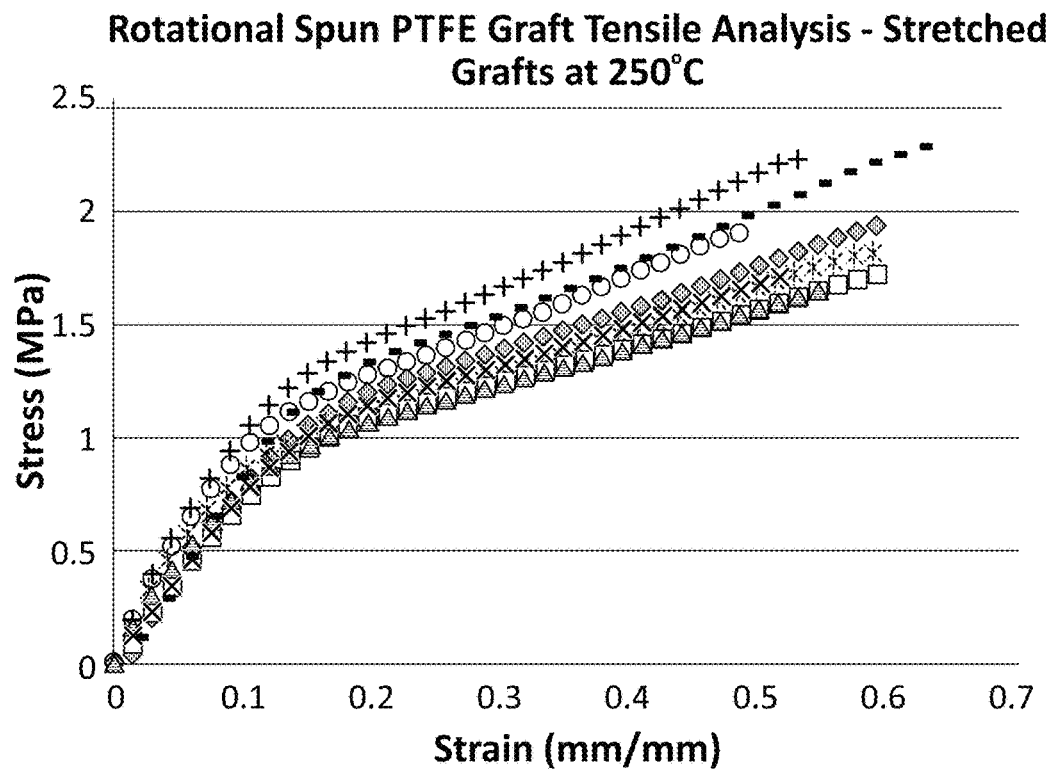
FIG. 10A is a graph showing the stress/strain curve for various rotational spun samples stretched at 250° C.
Figure 10B:
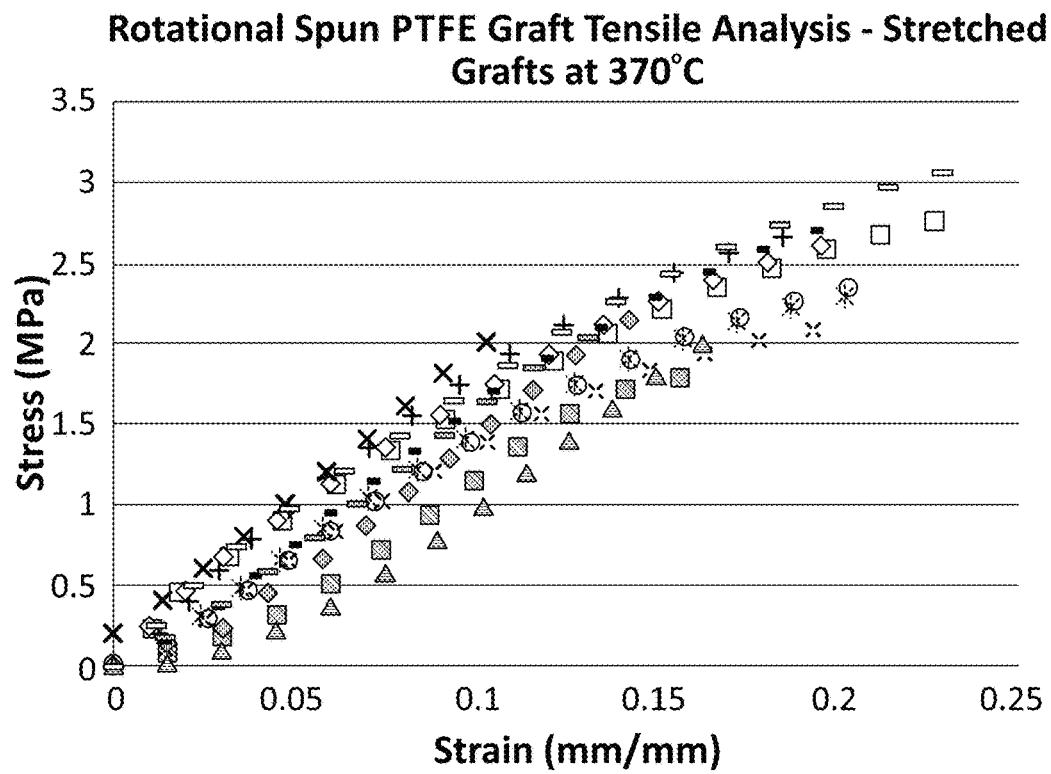
FIG. 10B is a graph showing the stress/strain curve for various rotational spun samples stretched at 370° C.
Figure 10C:
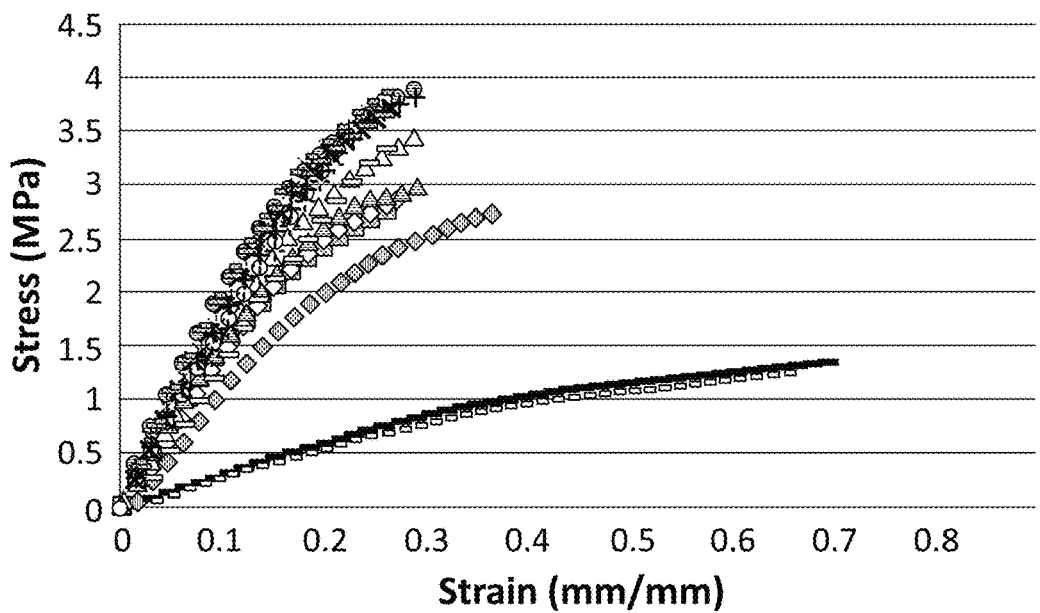
FIG. 10C is a graph showing the stress/strain curve for various rotational spun samples stretched at 385° C.
Figure 10D:
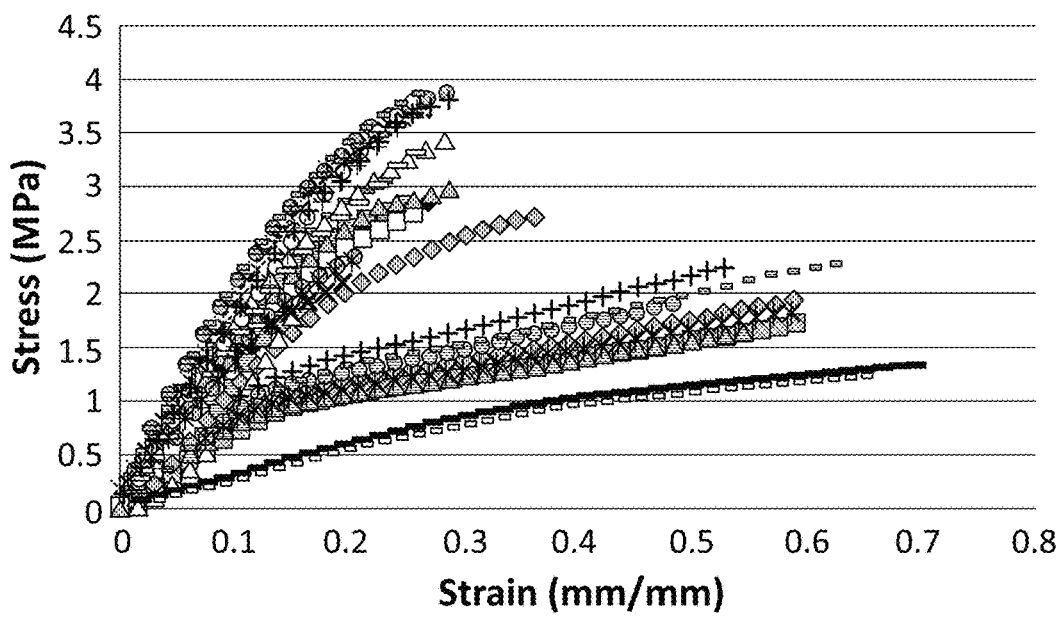
FIG. 10D is a graph showing the stress/strain curve for the materials of FIGS. 10A-10C, plotting on the same axes.

FIGS. 9A-10D summarize the results of this testing. As the membranes comprised a tubular geometry, the membranes are captioned as "grafts" on the graphs, but are not actual vascular grafts. FIG. 9A is a graph showing the stress/strain ratios for the stretched and control grafts. FIG. 9B is a graph showing the average stress at max load, plotted against the stretch ratio of each sample graft, for the grafts plotted in FIG. 9A. FIG. 10A is a graph showing the stress/strain curve for various rotational spun samples stretched at 250° C. FIG. 10B is a graph showing the stress/strain curve for various rotational spun samples stretched at 370° C. FIG. 10C is a graph showing the stress/strain curve for various rotational spun samples stretched at 385° C. FIG. 10D is a graph showing the stress/strain curve for the materials of FIGS. 10A-10C, plotted on the same axes for comparison.

These results show distinct tensile properties between standard rotational spun PTFE tubes and heated and stretched rotational spun PTFE tubes. Tensile analysis showed that the average tensile stress at the material breaking points can be increased by heating and stretching the membrane, and that the ultimate tensile strength is positively correlated to the stretch ratio with possible degradation of the membrane starting at stretch ratios beyond 350%.

Membranes stretched at 250° C. exhibited tensile behavior more like control grafts, while membranes stretched at 370° C. and 385° C. had much steeper stress-strain curves and showed increased ultimate tensile stress. Ultimate tensile strength was increased by an average of 169% for membranes stretched at 250° C. Ultimate tensile strength was increased by an average of 226% for membranes stretched at 370° C. and 291% for membranes stretched at 385° C.

Post-processing of the membranes affected the tensile behavior with higher stretch ratios and processing temperatures, effectively strain-hardening the membrane. Samples 9-2 and 9-3 did not show the same degree of strain-hardening as the other membranes processed at 385° C. Samples 9-2 and 9-3 were only stretched to 2.5 times the original length of the membrane, which was 28% less than the average stretch ratio of the other grafts processed at 385° C. The ultimate tensile strength of these samples was 60% lower than the average ultimate tensile strength of the other membranes processed at 385° C. Without being bound by theory, this result suggests that stretch ratio and processing temperature both affect the mechanical behavior of the membrane.

Additionally, tensile results of the heated and stretched rotational spun PTFE membranes tended to show that tensile properties of rotational spun PTFE membranes can be engineered with heat and mechanical post-processing. Ultimate tensile strength was increased by an average of 169% for membranes stretched at 250° C., 226% for membranes stretched at 370° C., and 291% for membranes stretched at 385° C.

Moreover, these results suggest increased resistance to creep in the direction of stretching. Creep behavior correlates directly to the mechanical properties of the membrane. Thus, in embodiments wherein the material exhibits greater strength in the stretched direction and decreased strength in the un-stretched direction, the material may also exhibit greater resistance to creep in the stretched direction and greater susceptibility to creep in the un-stretched direction. In one exemplary embodiment, a tube may be reinforced against creep in both the axial and radial directions by heat and stretch processing of the tube in the axial direction, then helically wrapping the tube with a strip of material that has been heat and stretch processed in the long direction of the strip. The increased strength along the length of the strip reinforces the hoop strength of the underlying tube. Additionally, creep behavior is also a function of temperature for materials that soften at elevated temperatures. Heating such a material and stretching that material while at an elevated temperature may result in creep resistance not found in un-stretched materials.

Example 1.10

Water Entry Pressure (WEP) testing was done to determine the water entry pressure of rotational spun tubes after post-processing by heating and stretching. Specifically, two tubes (samples A and B, below) of serially deposited PTFE fiber mats were prepared by rotational spinning an aqueous PTFE dispersion mixed with PEO and water. The tubes were sintered and cooled. After cooling, each tube was measured to have an initial length of 75 mm. The tubes were then heated at 385° C. for six minutes. Sample A was stretched to a final length of 260 mm while at temperature, and Sample B was stretched to a final length of 320 mm while at temperature. Each sample was then cut to form two test tubes from each sample, with lengths as shown below. A control tube of non-post-processed rotational spun PTFE was also evaluated. Each tube was tested by connecting a syringe, to provide water pressure, in fluid communication with a gauge and with the inside lumen of the tube, as further detailed below.

A 60 ml syringe was filled with deionized water and connected to a 0-30 psi pressure gauge. The tube was also connected to the pressure gauge at a first end of the tube. The second end of the tube was clamped with a hemostat. The system was pressurized using the syringe, and the pressure was recorded when two droplets of water were observed to have passed through the material. The results are summarized in Table 1 below. Two times the wall thickness, WEP pressure, sample length, and test observations are shown in Table 1.

TABLE 1

| 2X Wall Thickness (mm) | Sample No. | WEP Pressure (psi) | Sample Length (cm) | Observations |
| --- | --- | --- | --- | --- |
| 0.38 | A (left) | 2.5 | 11 | Tube aneurized to 14 mm diameter |
| 0.38 | A (right) | 2 | 11 | Tube aneurized to 15 mm diameter |
| 0.17 | B (left) | 1 | 10 | Tube aneurized to 30 mm diameter |
| 0.17 | B (right) | 1 | 12 | Tube aneurized to 30 mm diameter |
| 0.60 | Control | 5 | 10 | No aneurizing |

It was observed that tubes which have been heated and stretched in the axial direction are able to hold pressure but exhibit decreased radial strength and would aneurize, meaning the samples increased in diameter along the test length. This radial aneurization was uniform along the tested length. The aneurization was correlated with high fiber alignment in the axial direction. Without being bound by theory, fiber alignment in the axial direction may be correlated with increased axial strength but decreased radial strength.

2. Geometry Setting of Serially Deposited Fiber Mats

Serially deposited fibers may be set in various geometries by constraining the fibers in a particular geometry and heating the fibers. For example, in some embodiments, constraining a previously sintered (or otherwise structurally set) mat or lattice of serially deposited fibers in a particular configuration, softening the material of the mat or lattice (for example by heating), and allowing the material to reset may result in a "memory" effect wherein the material retains at least a portion of the constrained geometry. Materials may be shape-set as described in Section 2 of this disclosure whether or not the materials have been heated and stretched as described in Section 1 of this disclosure.

In embodiments comprising serially deposited polymeric fibers, heating the material at about the crystalline melt point of the material may facilitate setting of the geometry. The disclosure below may refer specifically to rotational spun PTFE fiber mats; however, it may be analogously applied to other processes (such as electrospinning) and/or other materials.

Figure 11A:
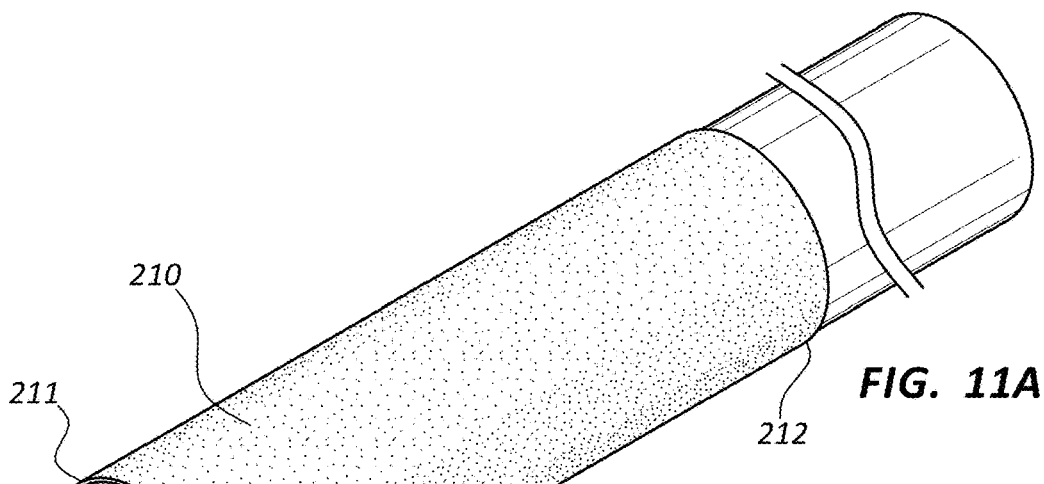
FIG. 11A is a perspective view of a membrane disposed on a mandrel.
Figure 11B:
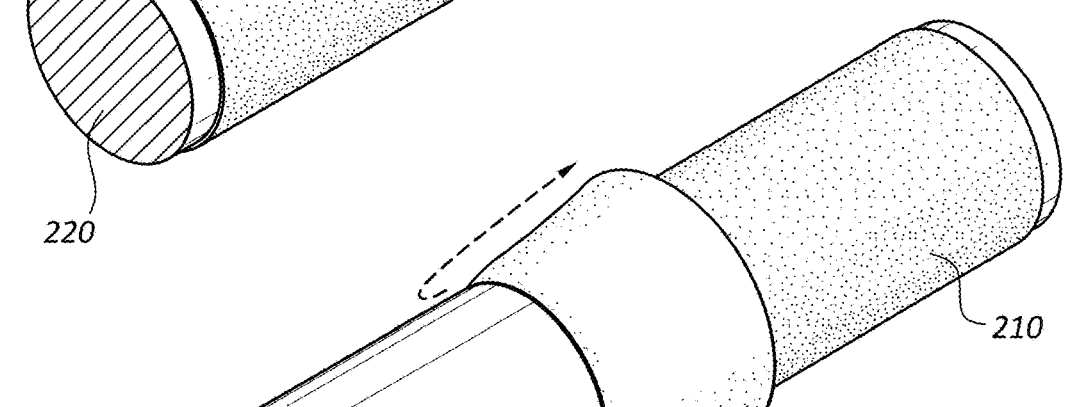
FIG. 11B is a perspective view of the membrane of FIG. 11A being removed from the mandrel.
Figure 11C:
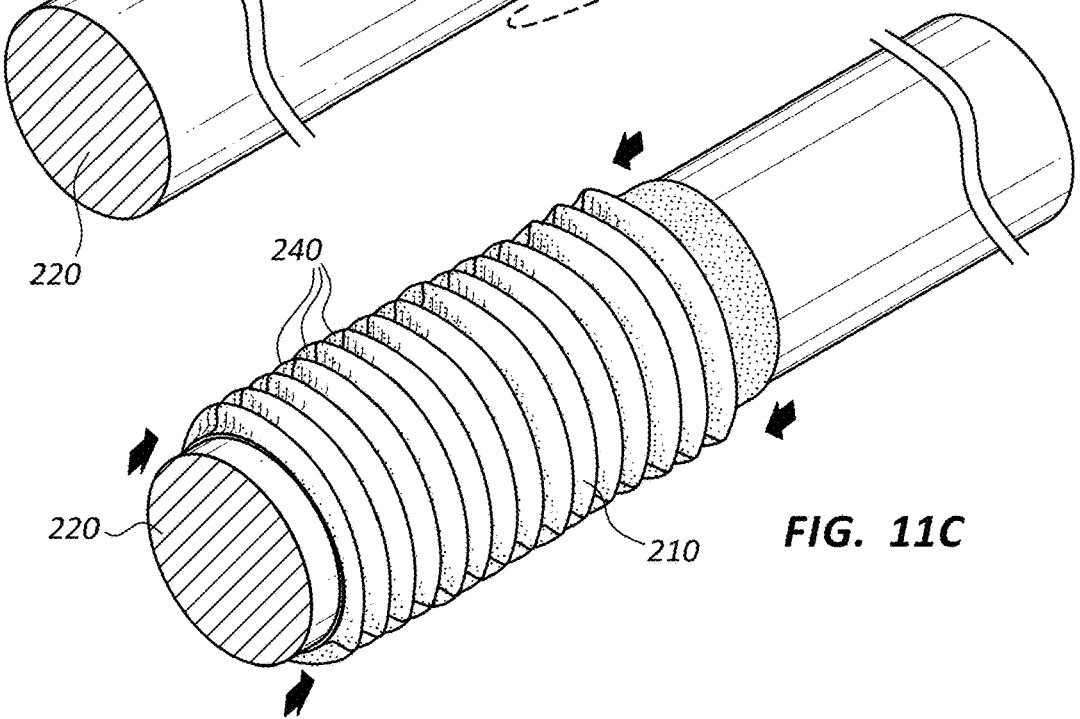
FIG. 11C is a perspective view of the membrane of FIG. 11A being compressed onto the mandrel.

FIGS. 11A-11C illustrate an exemplary process of setting the geometry of a serially deposited fiber mat. FIG. 11A is a perspective view of a serially deposited fiber membrane 210 disposed on a mandrel 220. The membrane 210 extends from a first end 211 to a second end 212. The membrane 210 may be serially deposited on the mandrel, 220 for example, through rotational spinning or electrospinning. The membrane 210 may also be sintered on the mandrel 220.

The sintered membrane 210 may be removed from the mandrel 220 by peeling the membrane 210 back, slipping it off, and so forth, as shown in FIG. 11B. Though the specific illustration includes a cylindrical mandrel, the present disclosure also applies to sheets, spheres, and other geometries of serially deposited fiber mats.

The membrane 210 of sintered serially disposed polymeric fibers may then be constrained in a variety of configurations. For example, FIG. 11C is a perspective view of the membrane 210 being compressed onto the mandrel 220. This configuration is exemplary; the membrane 210 could be constrained into various shapes. In the illustrated embodiment, the membrane 210 is compressed such that the tube is compressed along a shorter length, tending to create annular ridges or corrugations 240 along the length of the membrane 210.

Once the membrane 210 is constrained into the desired shape, the membrane 210 may be heated while constrained. After heating and cooling, the membrane 210 may tend to retain the constrained shape.

FIGS. 12A-12D illustrate an embodiment of a serially deposited fiber membrane which has been set into a corrugated configuration, analogous to the process described in connection with FIGS. 11A-11C, to form a corrugated tubular graft 310.

FIG. 12A is a perspective view of the corrugated tubular graft 310 in a first configuration. The graft 310 extends from a first end 311 to a second end 312 and has annular corrugations 340 along the length thereof. In the configuration of FIG. 12A, the graft 310 is disposed in a generally straight axial configuration.

FIG. 12B is a perspective view of the corrugated tubular graft 310 in a second configuration. The graft 310 follows a slightly more twisted or waved disposition as compared to the configuration of FIG. 12A. As generally indicated by the arrows, the graft 310 may exhibit elasticity between the first 311 and second 312 ends due to the corrugation. When pulled in the direction of the arrows (opposite the direction the graft 310 was compressed prior to heat-setting) then released, the graft 310 will tend to return to the heat-set corrugated configuration.

As further illustrated in FIGS. 12C and 12D, the corrugations may facilitate bending of the graft 310 between the first 311 and second 312 ends. Specifically, the annular corrugations may both reinforce the graft 310 and provide elasticity such that the graft 310 can bend in a variety of configurations without kinking. Thus, a corrugated graft 310 may be configured for use in bent or twisted configurations.

Multilayered constructs comprising corrugated or otherwise heat-set components are within the scope of this disclosure. For example, a tubular graft may comprise a corrugated tube coupled to a second tube having a relatively smooth wall (with respect to the corrugated tube). The tubes may overlap and be coaxial. In some embodiments a construct will be configured with a smooth wall tube defining an inside diameter (which may be a blood contacting surface) and a corrugated tube defining an outside diameter (to provide support to the construct). As used herein, a smooth wall component refers to a component without visually apparent surface defects or irregularities.

Example 2.1

A membrane of rotational spun PTFE fibers was spun for 5 minutes from a 0.07 g/ml PEO/PTFE dispersion at 7000 RPM onto an 8 mm mandrel rotating at 1500 RPM. The membrane was then sintered at 385° C. for 15 minutes. The membrane was cooled and removed from the mandrel. The cooled membrane was stretched to about 125% of its original length while cool, then axially compressed onto the mandrel to form a corrugated tube. The tube was constrained in the axially compressed state by wrapping the tube with PTFE tape. The compressed membrane tube was then heated at 325° C. for 15 minutes.

Once the membrane tube was cooled and the tape removed, the membrane tube retained the annular corrugations, similar to the corrugated graft illustrated in FIGS. 12A-12D. It was observed that the corrugated membrane tube was more compliant than non-corrugated tubes of the same material. Further, the lumen of the corrugated membrane tube remained open, illustrating kink resistance, when the membrane tube was bent up to 180°. It was further noted that the material was heated at 325° C., the crystalline melt point of the PTFE. Various materials may be set in various geometries through analogous processes.

Figure 13A:
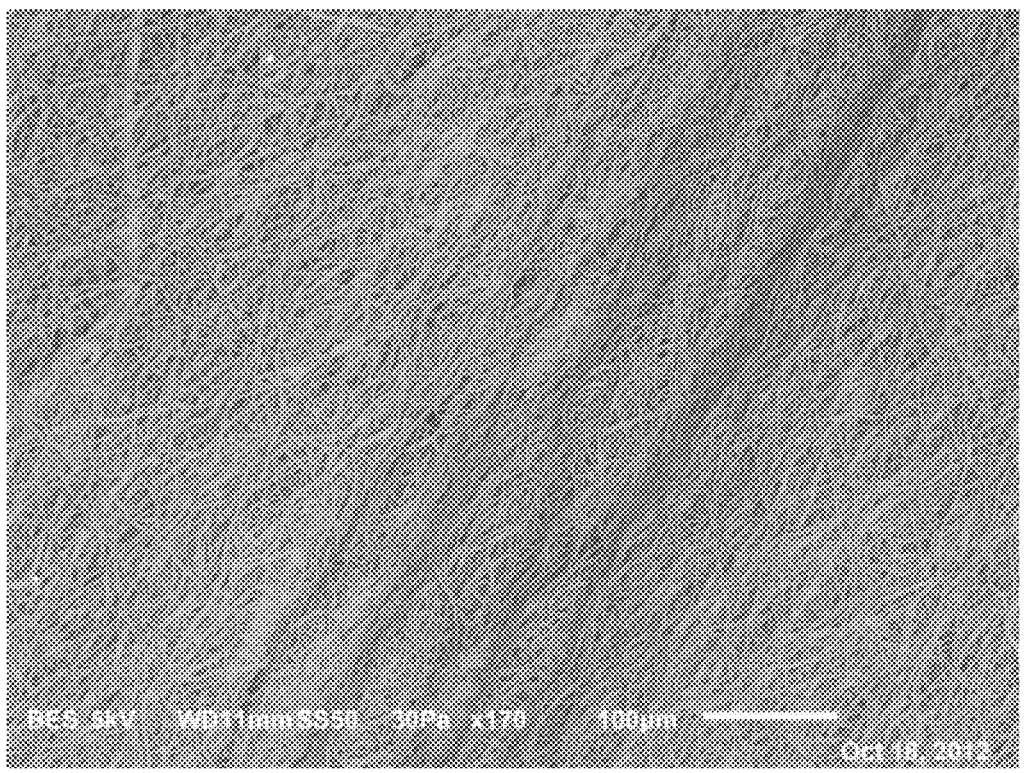
FIG. 13A is an SEM (170× magnification) of a rotational spun mat heat-set in a corrugated geometry.
Figure 13B:
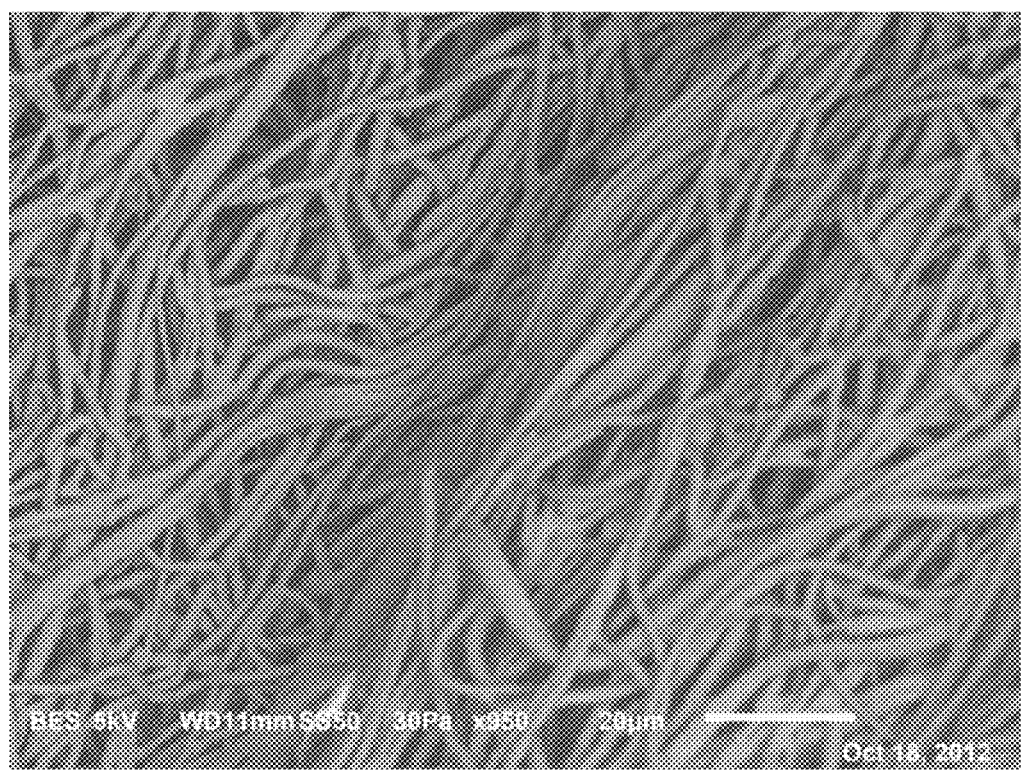
FIG. 13B is an SEM (950× magnification) of the rotational spun mat of FIG. 13A.

FIGS. 13A and 13B are SEMs of the corrugated membrane of this example. FIG. 13A is an SEM at 170× magnification, and FIG. 13B is an SEM at 950× magnification. A portion of the corrugations can be seen in these SEMs.

3. Reinforced Grafts

Tubular grafts may be reinforced through annular rings, helical reinforcements, and so forth. For example, annular corrugations heat-set in a tubular graft may comprise annular reinforcements. Additionally, separate components may be coupled to a graft to provide reinforcement. Reinforcing members may provide hoop strength, resist kinking, provide other structural support, and so on.

FIG. 14A is a front view of a tube 410 with reinforcing rings 440 disposed around a first layer 430. The first layer 430 and the rings 440 may comprise the same material or different materials. For example, the rings 440 may comprise generally stiffer materials than the first layer 430. Thus the first layer 430 may be configured to provide softness or elasticity to the construct, with the rings 440 configured to add strength. For example, the first layer 430 may comprise PTFE while the rings 440 comprise FEP. FIG. 14B is a front view of the tube 410 with a second layer 435 disposed over the first layer 430 and rings 440.

In some embodiments, the rings 440 are removable, to allow a practitioner to tailor the length of the reinforcing segment. In some embodiments removable rings 440 are used in connection with constructs having no second layer 435, while in other embodiments a portion of the second layer 435 is removable with the removable rings 440. Additionally or alternatively, constructs having one or more layers of serially deposited fibers may be reinforced with a metal frame or other structure, including structures comprised of Nitinol.

In some embodiments a construct is manufactured by serially depositing a tube of PTFE fibers (such as by rotational spinning or electrospinning), sintering the tube, and cooling. Discrete FEP rings and/or a helical spline of beading may be added for reinforcement. The tube may then be heated (for example, at about the crystalline melt point of the FEP) to bond the components. An additional layer of serially deposited PTFE fibers may be separately formed and placed over the rings before or after bonding, and may be serially deposited directly onto the rings. Furthermore, a helical spline or one or more grooved or raised portions may be comprised of serially deposited fibers. For example, fibers could be deposited on a helically threaded mandrel, the fibers creasing a tubular layer with integrally formed helical ridges or grooves (corresponding to the threads) on an inside diameter of the layer. After sintering, the grooved tube is removed from the mandrel by unthreading. The sintered tube may be utilized with the grooves on the inside diameter, or inverted so that the grooves are on the outside diameter and the inside diameter is smooth.

Referring again to FIGS. 14A and 14B, the first layer 430, the second layer 435, the rings 440, or any other portion of the construct may be formed of serially deposited fibers and may be heat- and stretch-processed or geometry-set as described in Sections 1 and 2 of this disclosure. For example, a heat-set corrugated graft may be used in connection with additional reinforcing rings formed of discrete components.

Figure 15A:
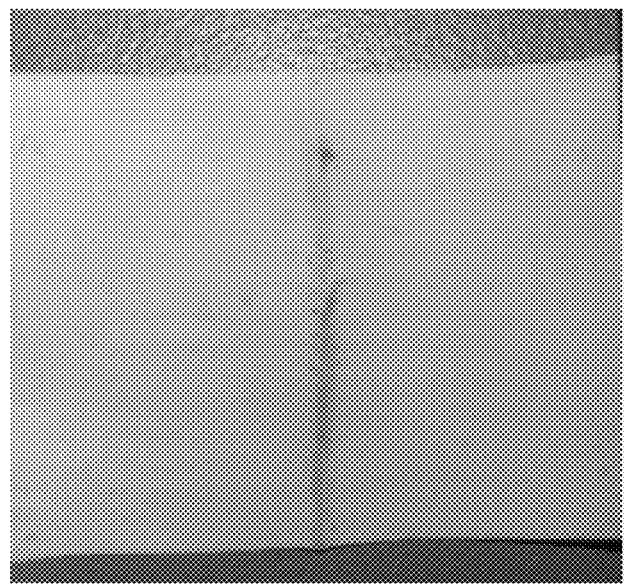
FIG. 15A is a photograph of a densified portion of a first rotational spun tube.
Figure 15B:
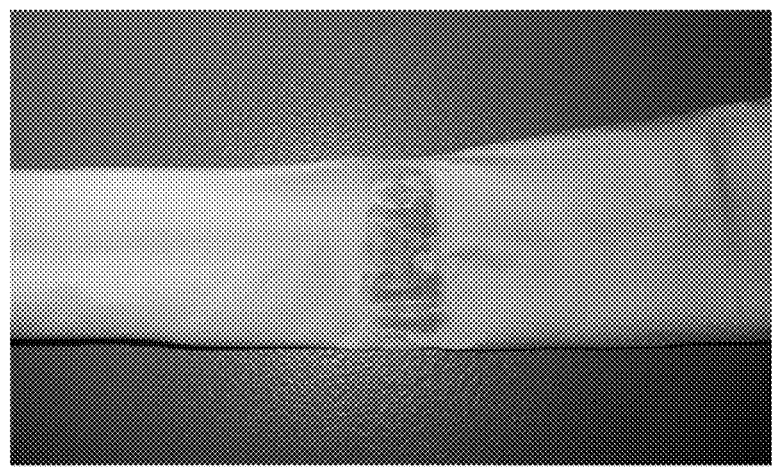
FIG. 15B is a photograph of a densified portion of a second rotational spun tube.
Figure 15C:
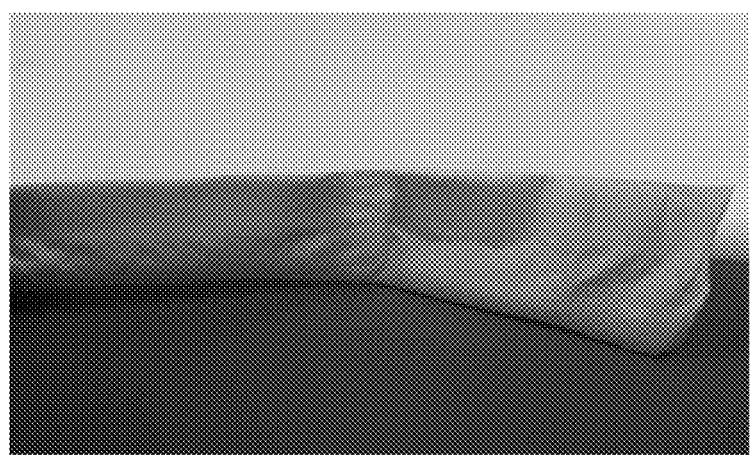
FIG. 15C is a backlit photograph of the densified portion of the rotational spun tube of FIG. 15B.

Reinforced and/or non-porous portions of a graft may also be created by densifying a portion of a serially deposited fiber mat or lattice. FIGS. 15A-15C are photographs of densified portions of rotational spun PTFE fiber mats. Specifically, FIG. 15A is a photograph of a densified portion of a first rotational spun tube, FIG. 15B is a photograph of a densified portion of a second rotational spun tube, and FIG. 15C is a backlit photograph of the densified portion of the rotational spun tube of FIG. 15B. The backlit photograph illustrates the increased translucence of the densified portion.

These densified portions may be created by applying heat and/or force to a local area of the mat, compressing the fibers in that area and increasing the density of the mat. This may also reduce the porosity of the mat at that point and may act as a reinforced portion of the mat. The densified portions of FIGS. 15A-15C appear as annular lines on the photographs. These portions were made by compressing the tubular membrane (while on a mandrel) with a hot roller.

The mat may be thinner and less porous at the densified portions, but exhibit increased strength and density. Densification may be used to create impermeable or relatively non-porous segments of a membrane.

Figure 16B:
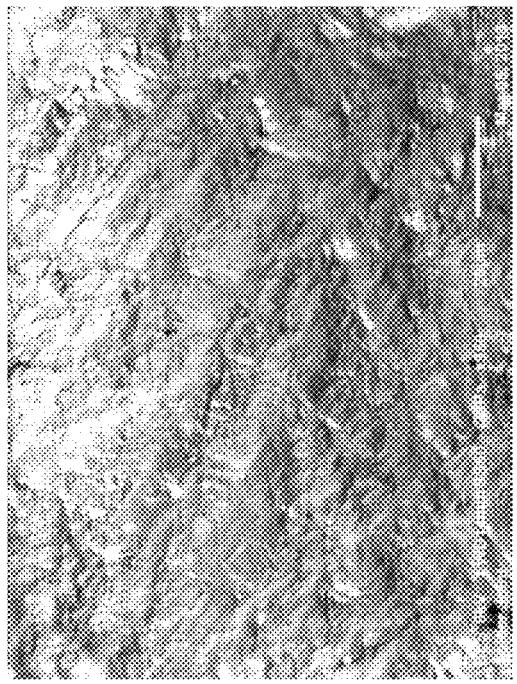
FIG. 16B is an SEM (950× magnification) of the densified portion of the rotational spun tube of FIG. 16A.
Figure 16D:
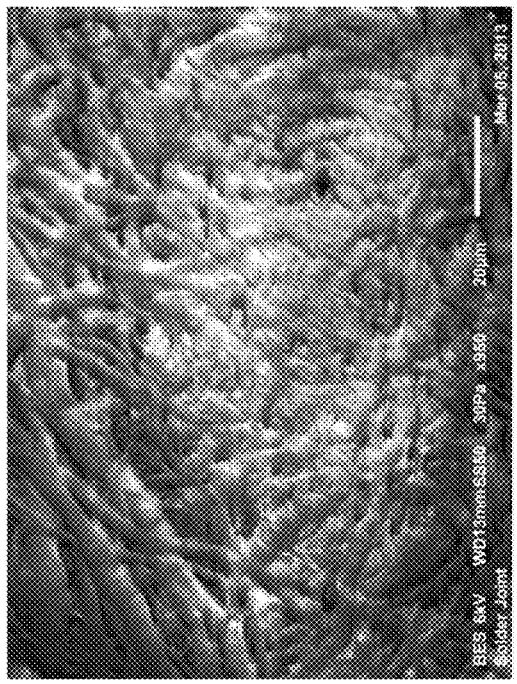
FIG. 16D is an SEM (950× magnification) of the rotational spun tube of FIGS. 15B and 15C, showing a partially densified portion.
Figure 16A:
FIG. 16A is an SEM (25× magnification) of the densified portion of the rotational spun tube of FIGS. 15B and 15C.

FIGS. 16A-16D are SEMs of the densified portion of the rotational spun tube of FIGS. 15B and 15C. FIG. 16A is an SEM at 25× magnification of the densified portion, and FIG. 16B is an SEM at 950× magnification of the same area. The SEMs show less porosity at the densified portion at both levels of magnification.

Figure 16C:
FIG. 16C is an SEM (110× magnification) of the rotational spun tube of FIGS. 15B and 15C, showing a densified portion and a non-densified portion.

FIG. 16C is an SEM (110× magnification) of the rotational spun tube showing both the densified portion and a non-densified portion. A transition to decreased porosity and less distinct fiber structures can be seen between the non-densified portion (to the left) and the densified portion (to the right). FIG. 16D is an SEM (950× magnification) of the rotational spun tube showing a partially densified portion. As compared with FIG. 16B, the SEM of a more densified portion at the same magnification, the partially densified sample shows more distinct fiber structures and more porosity, but less so than a non-densified portion.

4. Further Applications for Serially Deposited Fiber Mats and Lattices

Serially deposited fiber mats or lattices may exhibit reduced hole leakage when a cannula or another instrument pierces the fiber mat, as compared to other materials not comprising serially deposited fibers. The microstructure or nanostructure of the mat may facilitate contraction of the material around the void space after the cannula or other instrument is removed. The material may elastically recoil after piercing, generally sealing the opening. Serially deposited fiber mats may further exhibit less tearing or elongation caused by perforation. A suture passing through a serially deposited fiber mat is an example of this embodiment. The mat of serially deposited fibers may contract around the suture, reducing the area in which fluid can pass. FIGS. 17A-17D are SEMs showing two sutures in rotational spun PTFE mats as compared to commercially available expanded polytetrafluoroethylene (ePTFE) vascular graft materials. The rotational spun mats exhibit smaller openings around the sutures, suggesting less leakage.

Figure 17B:
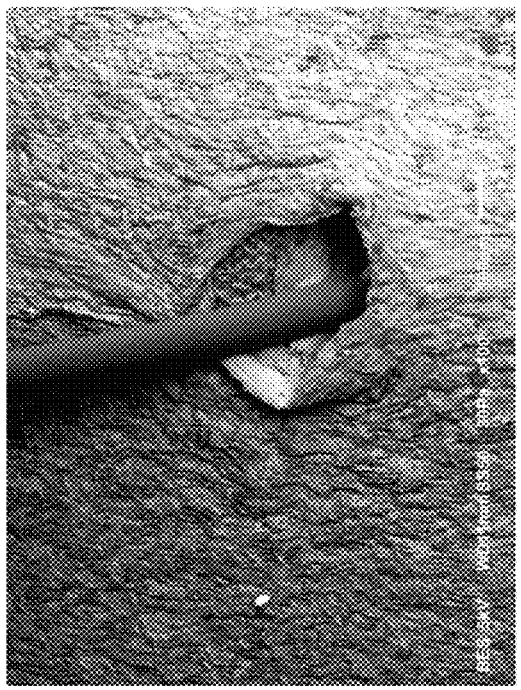
FIG. 17B is an SEM (100× magnification) of a commercially available expanded PTFE (ePTFE) vascular graft with a propylene suture disposed therein.
Figure 17D:
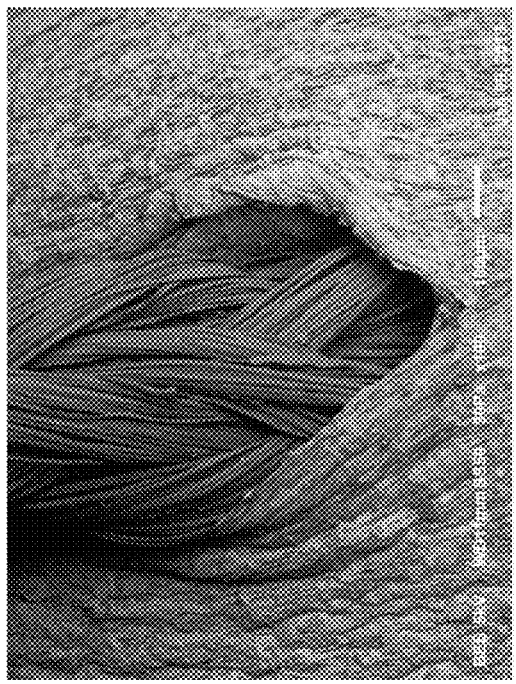
FIG. 17D is an SEM (100× magnification) of a commercially available ePTFE vascular graft with a silk suture disposed therein.
Figure 17A:
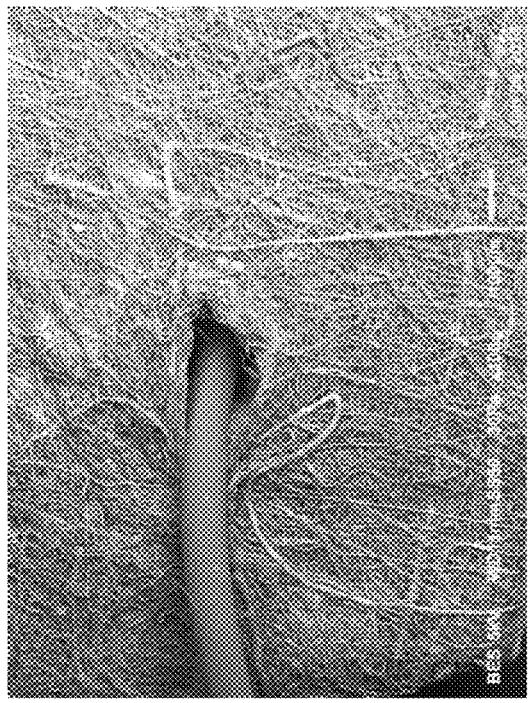
FIG. 17A is an SEM (100× magnification) of a rotational spun mat with a propylene suture disposed therein.
Figure 17C:
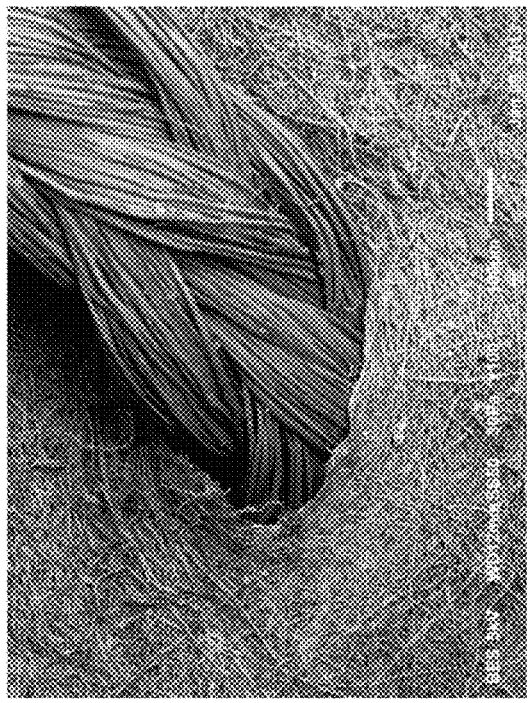
FIG. 17C is an SEM (100× magnification) of a rotational spun mat with a silk suture disposed therein.

FIG. 17A is an SEM (100× magnification) of a rotational spun mat with a propylene suture disposed therein. FIG. 17B is an SEM (100× magnification) of a commercially available ePTFE vascular graft with a propylene suture disposed therein. FIG. 17C is an SEM (100× magnification) of a rotational spun mat with a silk suture disposed therein. FIG. 17D is an SEM (100× magnification) of a commercially available ePTFE vascular graft with a silk suture disposed therein.

Additionally, serially deposited fibers may be used as layered coatings on a variety of medical appliances or other devices. These coatings may be used to improve surface interactions and/or change surface properties such as hydrophobicity and coefficient of friction. A coating of serially deposited fibers may be used to improve surface interactions of artificial joints, such as knee or hip implants, at the interaction points between components of the artificial joints and/or other artificial components or biologic structures. Also, coatings on devices such as catheters may change the hydrophobicity of the device.

Serially deposited mats or lattices may further be used as scaffolds for biologic tissue growth. Rotational spun ceramics, for example, may be used as a scaffold for bone growth and/or as prosthetic vertebrae.

5. Material Characteristics of Exemplary Serially Deposited Fiber Mats

Material characteristics of serially deposited fiber mats may be analyzed by imaging a portion of the fiber mat and evaluating the characteristics of the fibers shown in the image. The images may be evaluated manually and/or through the use of software or other analysis tools. Such images may be magnified to facilitate characterization of the fiber mat. For example, in some instances, Scanning Electron Micrographs (SEMs) may be used when characterizing a fiber mat.

The ranges and characteristics disclosed below were determined by mounting samples of serially deposited fiber mats on SEM imaging stubs. The mats were then imaged using a JEOL scanning electron microscope. The images evaluated with respect to the disclosure below were each taken at 950× magnification.

The SEMs were evaluated using software analysis to measure various characteristics of the fiber mats. As part of this exemplary process, the image is first converted to a "binary image," or an image showing only black and white portions, for example. The binary image is then analyzed, fibers identified, and characteristics determined by comparing the relative numbers and placements of each type of binary pixel. For example, an image is converted to a black and white image wherein black portions represent gaps or holes in the serially deposited fiber mat while white portions represent the fibers of the mat. The software thus identifies the presence and position of fibers and pores or open portions of the fiber mat. As further detailed below, characteristics such as fiber width and pore size may be determined by analyzing these binary images. Still further, characteristics of relative fibers, such as the number of fiber branches, intersections, bundles, fiber density, and so forth, may be determined as further detailed below. In some instances, a code or script may be configured to make various analyses and calculations.

In one embodiment, the analysis software calibrates the subject image prior to analysis to ensure accurate measurements. Such calibration is performed by using images of objects traceable to NIST standards and spaced at known intervals. The minimum pixel distance between such objects is determined and then applied as a standard to measure other materials in the image, materials which are defined as groups of pixels in the binary images. The resolution accuracy for the 950× SEMs described herein is ±0.0526 µm.

Various features of a fiber mat may be identified based on an SEM or other image and/or a binary image obtained from an SEM or other image. These features may be identified manually by a user, through the use of software, or both, including instances wherein a user manually confirms features identified by software. In addition to features defined by the presence or absence of fibers (e.g., number of fibers, fiber density, number of pores, average pore size, percent porosity), some features may be defined by the relative positions of more than one fiber.

As used below, fiber diameter refers to the shortest distance crossing the width of a fiber. The fiber thus extends along an axis orthogonal to a line across the width of the fiber. Relative angles of fibers may be determined by comparing these axes of extension. A pore within a fiber mat is defined as an area or volume encapsulated by intersecting or branched fibers. An intersection of fibers comprises one or more fibers crossing such that the axes of the fibers are not in the same plane at the point of intersection. Branched fibers comprise instances wherein fibers divide into two or more fibers. Furthermore, a bundle of fibers is defined as one or more fibers in contact in which the axes of the fibers are parallel or substantially parallel along a portion of the fibers.

Figure 18:
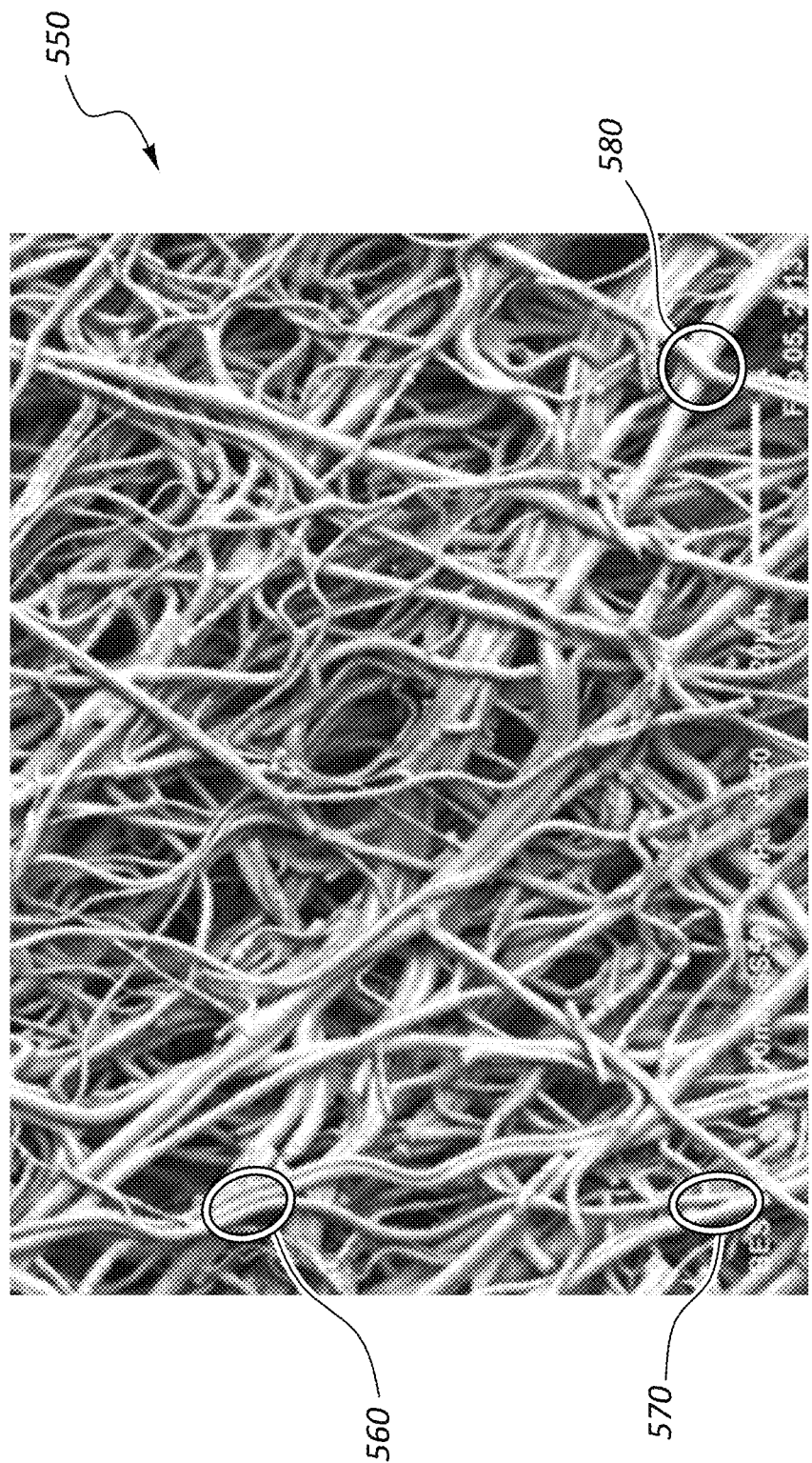
FIG. 18 is a Scanning Electron Micrograph (SEM) at 950× magnification of a first sample of a serially deposited fiber mat, exhibiting generally random fiber disposition.

FIG. 18 is an SEM at 950× magnification of a first sample of a serially deposited fiber mat 550. The fibers of the serially deposited mat 550 of FIG. 18 are generally randomly aligned, not exhibiting significant fiber alignment. An example of bundled fibers 560, or one or more fibers in contact in which the axes of the fibers are parallel or substantially parallel along a portion of the fibers, is indicated. Additionally, an example of branched fibers 570, or fibers dividing into two or more fibers, is also shown. Finally, an example of a fiber intersection 580, or an instance where one or more fibers cross such that the axes of the fibers are not in the same plane, is also indicated.

Figure 19:
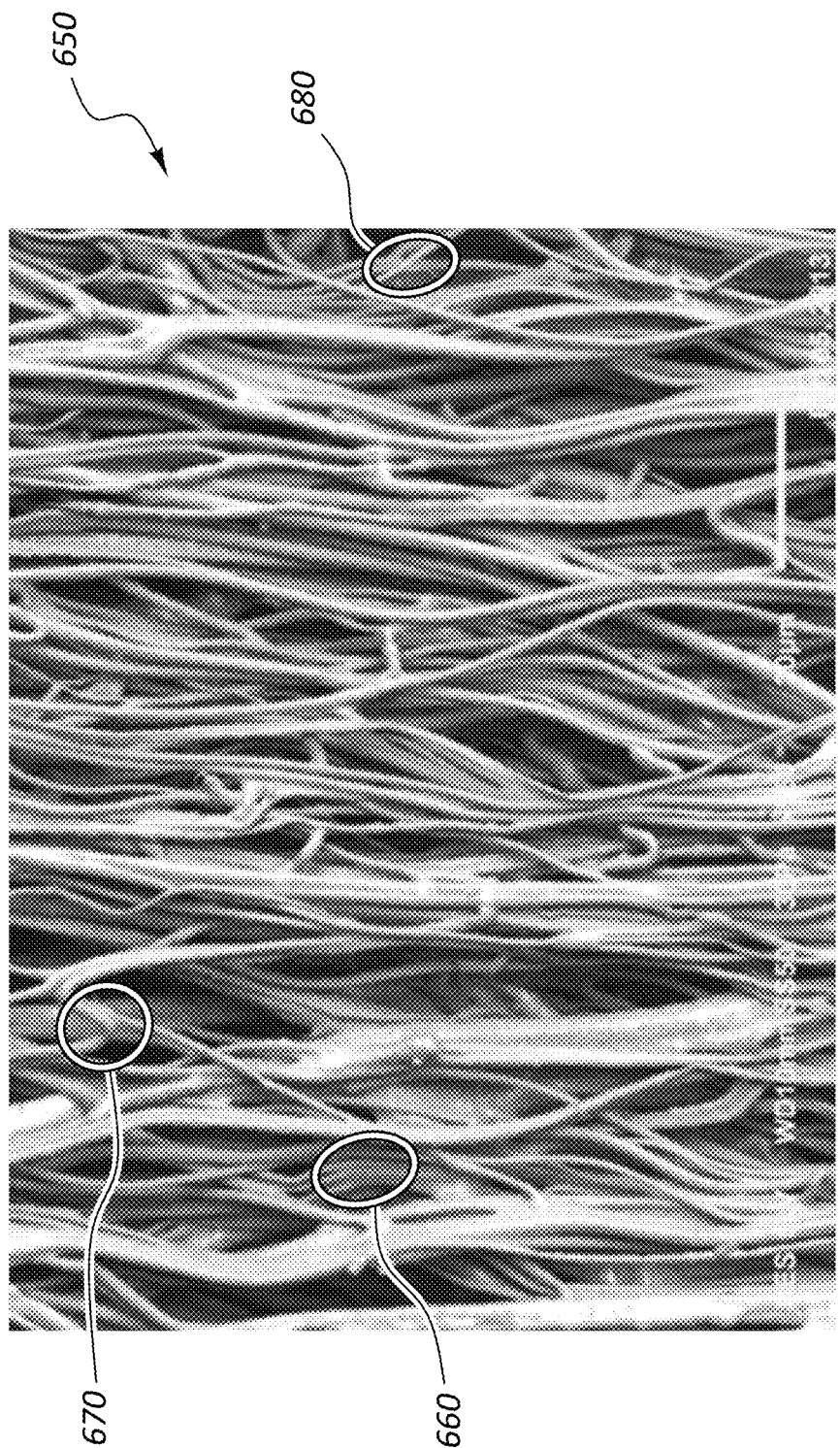
FIG. 19 is an SEM at 950× magnification of a second sample of a serially deposited fiber mat, exhibiting generally aligned fiber disposition.

FIG. 19 is an SEM at 950× magnification of a second sample of a serially deposited fiber mat 650. The fibers of the serially deposited fiber mat 650 of FIG. 19 exhibit increased fiber alignment as compared to the serially deposited fiber mat 550 of FIG. 18. As with the embodiment of FIG. 18, examples of bundled fibers 660, branched fibers 670, and intersecting fibers 680 are indicated.

Without being bound by theory, it has been observed that tubular medical devices comprising an inside surface of generally aligned fibers may exhibit favorable biologic responses. Again, without being bound by theory, fibers along the inside diameter of a tubular prosthesis configured to accommodate blood flow may facilitate endothelization of the inside diameter when the fibers are generally aligned along the direction of flow.

Figure 20:
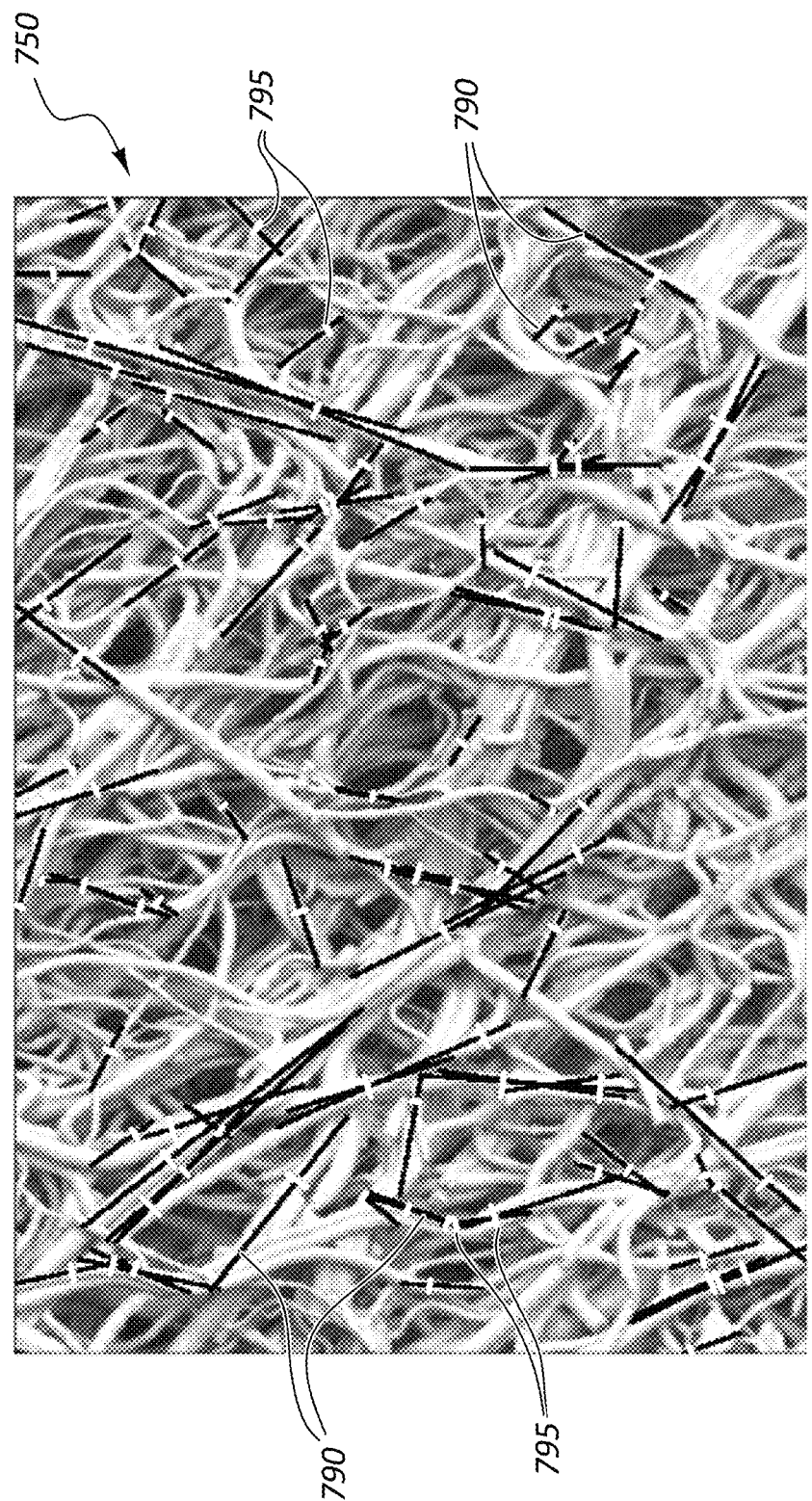
FIG. 20 is the SEM of the serially deposited fiber mat of FIG. 18, with lines indicating fiber axes and widths.

FIG. 20 is an SEM at 950× magnification of the serially deposited fiber mat 750 (from FIG. 18) with lines indicating fiber axes and widths. To determine average fiber width and average fiber angle, a number of points may be randomly selected within the portions of the image identified as fibers (the white image portions in FIG. 20). The shortest straight distance across the width of each fiber is then measured for each point. The fiber widths corresponding to a collection of points for the serially deposited fiber mat 750 of FIG. 20 are indicated by white lines designated by ref numeral 795.

Fiber axis may then be determined by extending an axis 790 orthogonal to, and through the midpoint of, each width line 795. These axes 790 may extend along the fiber until the fiber turns away from itself or until another fiber crosses the axis 790. In instances wherein the image is composed of black (open space in the exemplary embodiment) and white (fibers in the exemplary embodiment) pixels, the axes 790 may extend until intersecting a pixel indicating open space.

Fiber angle may then be determined by comparing the angle of these axes 790 with a coordinate system. For example, a reference line may be extended across the SEM, and the angle between each axis 790 and the reference line determined. In such a coordinate system, each axis 790 will form an angle between 0° and 180° with the reference line, when measuring each angle from the reference line in the same direction and from the same side of the reference line. Because the orientation of the SEM (or the placement of the reference line with respect to the SEM) will impact angles measured in this way, the measured angles may be considered relative, rather than absolute, values. In other words, fiber angle may be expressed as the relative position of the fibers from an arbitrary reference.

Patterns in fiber orientation may then be expressed by comparing the relative angles formed between each axis 790 and the reference line. Comparing the relative angles between the axes 790 and the reference line to each other nullifies the arbitrary nature of the placement of the reference line. In other words, expressing the angles in terms of their similarity or difference to other angles will tend to show a generally even distribution of angles for random fibers and a clustered distribution for aligned fibers, regardless of the initial position of the reference line. The angle formed between a first fiber and the reference line will be similar to the angles between other fibers which are generally aligned with the first fiber.

The shape and mode of the distribution of fiber angles with respect to an arbitrary reference may thus indicate the degree to which the fibers are aligned. Random fiber alignment will generate an even distribution, while aligned fibers will generate a clustered distribution. In some instances, a clustered distribution may create a distribution generally shaped as a bell curve, with a cluster of fiber angles around a particular angle sloping down to relatively few fiber angles at the "tails" of the curve. Because the reference line is arbitrary, the position of the angle value at the center of the curve (with respect to the reference line) is also arbitrary. The cluster, curve, and tails may be understood as ranges of angles (such as 60% of the angles fall within a 40° range). To nullify any effect due to the arbitrary placement of the reference, ranges of angles given herein equate 0° and 180° from the reference line as the same angle. In other words, a fiber lying directly on the reference line could be expressed as disposed at either 0° or 180° to the reference line. Continuous ranges of angles may thus cross the 0°/180° point on the arbitrary coordinate system. For example, a range of 20° centered around an angle of 175° (with respect to the reference line) would encompass angles from 165° to 180° and from 0° to 5° (with respect to the reference line).

In some embodiments, the fiber angles can also be categorized, and the distribution approximated, by sorting the fiber angles into various "bins" or groups of angles with respect to the reference line, such as X fibers from angles between 0° and 10° with respect to the reference line, Y fibers from angles between 10° and 20°, and so forth. Again, in such an expression, the orientation of the reference line (and likewise the orientation of the SEM) will only affect the expression of the angles to the extent it influences the relative positions of each bin. In other words, the position of a bin is still determined with respect to the reference line, so the position of the dividing angles between bins will depend on the position of the reference line. Of course, the smaller the bin size, the less impact the position of the reference line will have. For small enough bins, the placement of the reference line will have no measurable effect.

Use of smaller bins will thus tend to mitigate the effects of the relative position of a bin dividing line. For example, if the bins are large and a bin dividing line splits a cluster of fiber angles, the numerical count of angles may not clearly indicate the presence and/or size of the cluster. However, if the bins are small, the higher number of bins will tend to mitigate such effects, and the same cluster will be seen across multiple small adjacent bins. In a random fiber alignment, the angles should divide substantially equally into bins regardless of the relative position of the bins as long as each bin contains the same magnitude range of angles. Aligned fibers will show clustering within adjacent bins. In either case, smaller bin size will more precisely express the fiber angle distribution.

Fiber angles were determined for a number of randomly identified fibers for the fiber mats shown in FIGS. 18 and 19. FIG. 20 is a graphical representation of the points and fiber angles identified for the mat of FIG. 18. The fiber angles were then sorted into bins at 10° intervals. The results are shown in Table 2, below.

TABLE 2

| Angle Bins (in degrees) | FIG. 18 - Random Fibers | | FIG. 19 - Aligned Fibers | |
| --- | --- | --- | --- | --- |
| | Number of Angles in Bin | Percent of Angles in Bin | Number of Angles in Bin | Percent of Angles in Bin |
| 0-10 | 6 | 6.32% | 4 | 6.35% |
| 10-20 | 8 | 8.42% | 5 | 7.94% |
| 20-30 | 8 | 8.42% | 3 | 4.76% |
| 30-40 | 7 | 7.37% | 9 | 14.29% |
| 40-50 | 9 | 9.47% | 13 | 20.63% |
| 50-60 | 5 | 5.26% | 15 | 23.81% |
| 60-70 | 5 | 5.26% | 3 | 4.76% |
| 70-80 | 9 | 9.47% | 1 | 1.59% |
| 80-90 | 4 | 4.21% | 1 | 1.59% |
| 90-100 | 8 | 8.42% | 1 | 1.59% |
| 100-110 | 1 | 1.05% | 2 | 3.17% |
| 110-120 | 1 | 1.05% | 0 | 0.00% |
| 120-130 | 4 | 4.21% | 1 | 1.59% |
| 130-140 | 4 | 4.21% | 0 | 0.00% |
| 140-150 | 3 | 3.16% | 0 | 0.00% |
| 150-160 | 6 | 6.32% | 2 | 3.17% |
| 160-170 | 3 | 3.16% | 3 | 4.76% |
| 170-180 | 4 | 4.21% | 0 | 0.00% |

The fiber mat of FIG. 18 showed a high degree of randomization with no range of 10° containing more than 10% of the angles of the distribution and over 75% of the 10° range bins containing at least 4.21% of the total number of angles. The fiber mat of FIG. 19, showing a high degree of alignment, had 58.7% of the fiber angles within a 30° range and 44.4% of the fiber angles within a 20° range.

Fiber mats wherein less than 20%, including less than 15% and less than 10%, of the analyzed fiber angles fall within a 10° range exhibit randomization of fibers. Fiber mats wherein over 25%, including over 30%, or over 40%, of the angles fall in a 30° range, and fiber mats wherein over 35%, including over 50%, or over 55%, of the angles fall in a 40° range exhibit alignment of fibers. When analyzing serially deposited fiber mats as discussed above, the degree of magnification and/or the size of the image may affect the analysis at the extremes. In other words, too little magnification will not allow for identification of individual fibers and too much magnification may distort the effects of a few fibers (as an insufficient sampling of fibers may be present in the viewing area of the image). The fiber mats examined above were enlarged 950×. Any magnification wherein at least 30 individual fibers can be identified and the angles of those fibers determined may be utilized in the analysis above. Further, references herein to characteristics of fiber mats determined by extrapolating a magnified image (including pore size, fiber angle, fiber diameter, and so forth) are based on a magnification and view wherein at least 30 individual fibers can be identified.

Additionally, serially deposited fiber mats having larger numbers of intersections and/or branches per unit area exhibit less fiber alignment than mats with relatively fewer intersections and/or branches.

The original set of random points and/or the width lines may be identified using a software recognition program. Further, each point may be checked manually to ensure that each point was on a fiber and each width line properly oriented.

Figure 21:
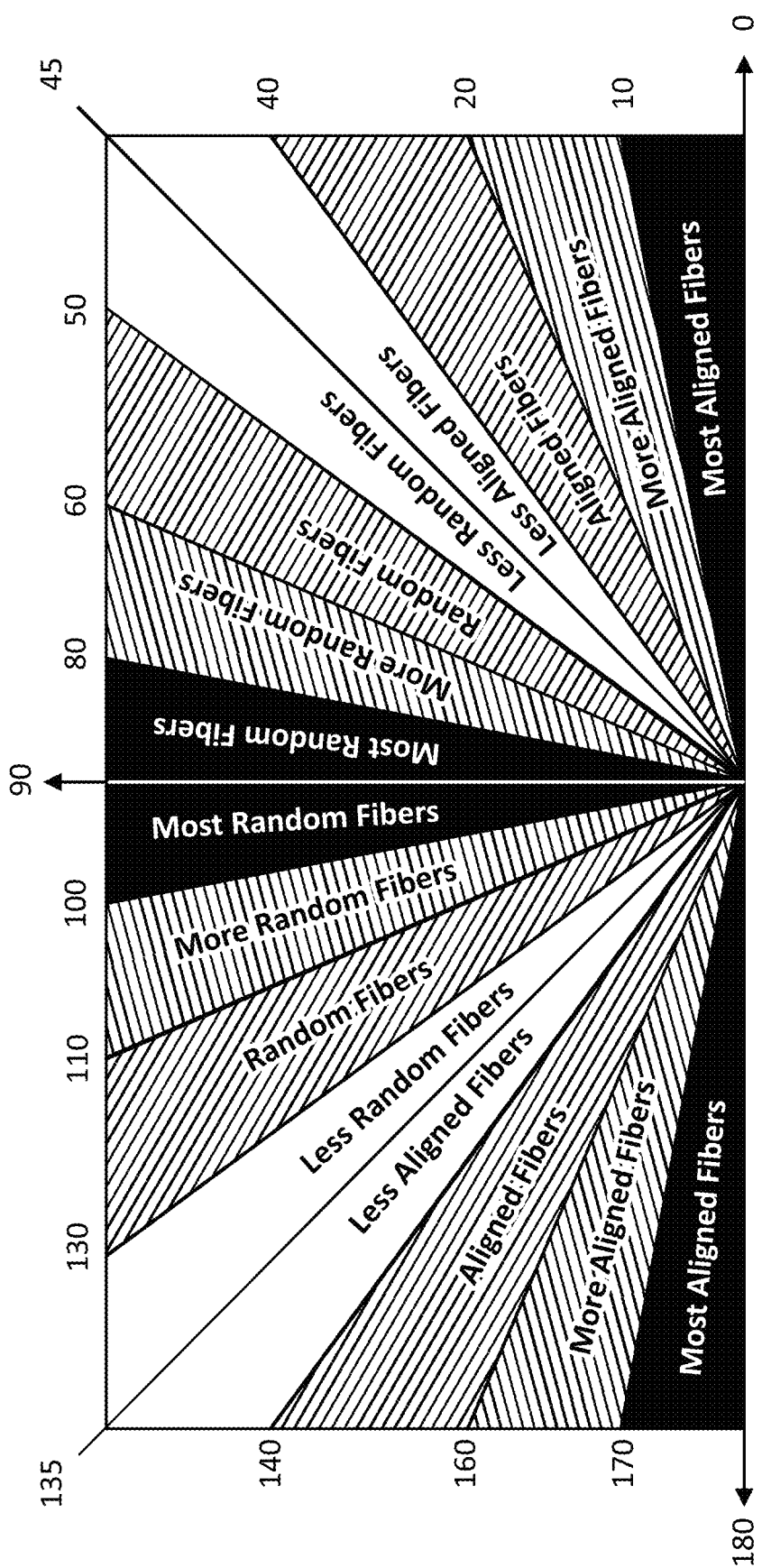
FIG. 21 is a chart summarizing the relationship of the angle, in degrees, of intersecting, branching, or bundled fibers and general fiber alignment of a serially deposited fiber mat.

FIG. 21 is a chart summarizing the relationship of the angle, in degrees, of intersecting, branching, or bundled fibers and general fiber alignment of a serially deposited fiber mat, with respect to a reference line drawn along the direction of stretching for an aligned mat. This chart illustrates the relationship along a continuum between fiber angle and the degree of randomization of the fibers when compared to the direction of stretching. As shown in FIG. 21, angles between 0° and 10° and between 170° and 180° indicate the highest degree of fiber alignment while angles between 80° and 100° indicate the highest degree of randomization of the fibers. In other words, the more the stretching process tends to align the fibers, the more fibers will fall in the aligned angle ranges. The relative degree to which other angles indicate randomization or alignment is indicated in FIG. 21.

Features of a portion of a fiber mat may also be extrapolated with respect to the entire mat. For example, average fiber angle of a portion, such as the portion of a fiber mat imaged in an SEM, may be extrapolated to an entire mat in some instances. Likewise, certain characteristics may be given with respect to units of area or volume (e.g., number of fibers per square millimeter ($mm^2$)), which also may be extrapolated with respect to an entire serially deposited fiber mat.

Serially deposited fibers may be directly deposited on various devices, products, and surfaces. For instance, serially deposited fibers may be deposited directly on an existing medical appliance such as a stent graft, stent, patch, or balloon. Such coatings may be configured to provide additional strength to the appliance, increase puncture resistance, provide a lubricious coating, and so forth.

Serially deposited fibers may have relatively small diameters and masses, which may allow the fibers to evenly coat the contours of a medical appliance or other device. For example, serially deposited fibers may be deposited on a balloon such that they evenly coat the entire surface of the balloon, including the contours of the portions of the balloon which transition between a large diameter and a small diameter. Thus, in some embodiments, serially deposited fiber coatings may be applied at a relatively uniform thickness and at a relatively uniform fiber density over the surface of a balloon or other medical appliance.

In some embodiments, an exemplary balloon may be coated with serially deposited fibers according to a procedure comprised as follows. First, an inflated balloon may be placed within a serially deposited fiber apparatus, or in proximity to a rotational spinning spinneret, for example. Material to be serially deposited may then be loaded into the apparatus. The apparatus may then be operated and the balloon coated with fibers, by rotational spinning or electrospinning, for example. The thickness of the coating may be controlled by the amount of time the apparatus is allowed to run. The balloon may then be removed. The serially deposited fiber material may be cured (for example, to remove solvent) if necessary. In some instances, curing may comprise heating the construct, including heating the construct such that the coating is sintered. Certain materials, such as nylon, for example, may not require sintering. Additionally, in some embodiments the balloon may first be dipped in or spray-coated with an additional layer of material configured to bond the fibers to the substrate.

Serially deposited fibers may be deposited on a rotating medical appliance (e.g., a balloon or stent graft) or deposited on a rotating collection surface (e.g., a mandrel). During serial deposition of fibers, controlling the direction and/or speed of rotation of the medical appliance or collector may affect the deposition of fibers. For example, in embodiments wherein a medical appliance or mandrel is configured to rotate about an axis parallel to the axis of rotation of a rotational spinning spinneret, the fibers may be deposited in an oriented arrangement, with the fibers tending to wrap around a circumference of the medical appliance or mandrel.

For any type of serially deposited fibers collected on a rotating device, varying the rotational speed of the collection device during the process may affect the properties of the resultant serially deposited fiber mat. In some embodiments a collection mandrel or medical device to be coated may be rotated at between about 100 RPM and about 10,000 RPM or more, including from about 200 RPM to about 5,000 RPM, from about 1,000 RPM to about 3,000 RPM, or from about 1,000 RPM to about 10,000 RPM. In some embodiments, higher rotational speeds may result in a relatively more aligned fiber pattern on the collection mandrel or device. Serially deposited fiber coatings are further described in U.S. patent application Ser. No. 13/829,493, titled "Multilayered Balloon," filed on Mar. 14, 2013, the entirety of which is hereby incorporated by reference.

Features such as the number of fibers, number of fiber intersections, number of fiber branches, and number of fiber bundles per unit area may be determined by randomly selecting a measurement area. The features may then be counted—manually, by software, or both—and the number of features divided by the size of the sampling area to yield a result in features per unit area. An analogous procedure could be used to determine features per unit volume.

Serially deposited fiber mats may be formed with various features and characteristics. Serially deposited fiber mats wherein 95% of the diameters of the serially deposited fibers (which may be determined by measuring the widths of fibers as indicated above) are between 50 nm and 6 µm, including from 700 nm to 3 µm and from 900 nm to 2 µm, are within the scope of this disclosure.

Further, serially deposited fiber mats of thicknesses from 50 nm to 800 µm, including from 50 µm to 200 µm, are within the scope of this disclosure. Serially deposited fiber mats with a variety of fiber densities are likewise within the scope of this disclosure: for example, mats comprising an average of from 5,000 to 150,000 fibers per $mm^2$, including mats averaging between 12,000 and 55,000 fibers per $mm^2$.

Average pore diameter and average pore area may be calculated programmatically using procedures analogous to those discussed in connection with other measurements herein. For example, an image may be evaluated to distinguish between areas comprising fibers and open areas, such as by creating a binary image as discussed above. Pores, or areas within a fiber mat encapsulated by intersecting or branched fibers, may then be identified. To determine the average pore diameter, a large sample of pores may be randomly selected from the target image. In some instances between 50 and 300 pores may comprise the sample. As used herein, the diameter of a particular pore is calculated by tracing thirty diameters of equal angular spacing around the pore through the centroid of the pore. The thirty diameters are then averaged to determine the calculated effective diameter of the pore. The area of each identified pore may also be computed based on the pixel area of each pore. Each pore identified for sampling may be manually checked to confirm proper identification of pores. The average pore diameter of a fiber mat may then be computed by averaging the calculated effective diameters of the identified pore. Mats having average pore diameters of from 1 µm to 10 µm, including from 2 µm to 3.5 µm, may be incorporated into implantable medical devices as disclosed herein. Material total porosity may also be determined by the percentage of dark pixels to light pixels in the image.

Serially deposited fiber mats may further be characterized by the number of intersections, branches, or bundles within an area of the mat. Serially deposited fiber mats having between 100 and 100,000 intersections per $mm^2$, including mats having between 4,000 and 65,000 intersections per $mm^2$, are within the scope of this disclosure and may be incorporated into implantable medical devices as disclosed herein. Additionally, serially deposited fiber mats having between 0 and 20,000 branches per $mm^2$, including between 400 and 7,500 branches, per $mm^2$ are within the scope of this disclosure and may be incorporated into implantable medical devices. Moreover, serially deposited fiber mats having between 0 and 30,000 bundles per $mm^2$, including between 400 and 10,000 bundles per $mm^2$, are within the scope of this disclosure and may be incorporated into implantable medical devices.

Figure 22:
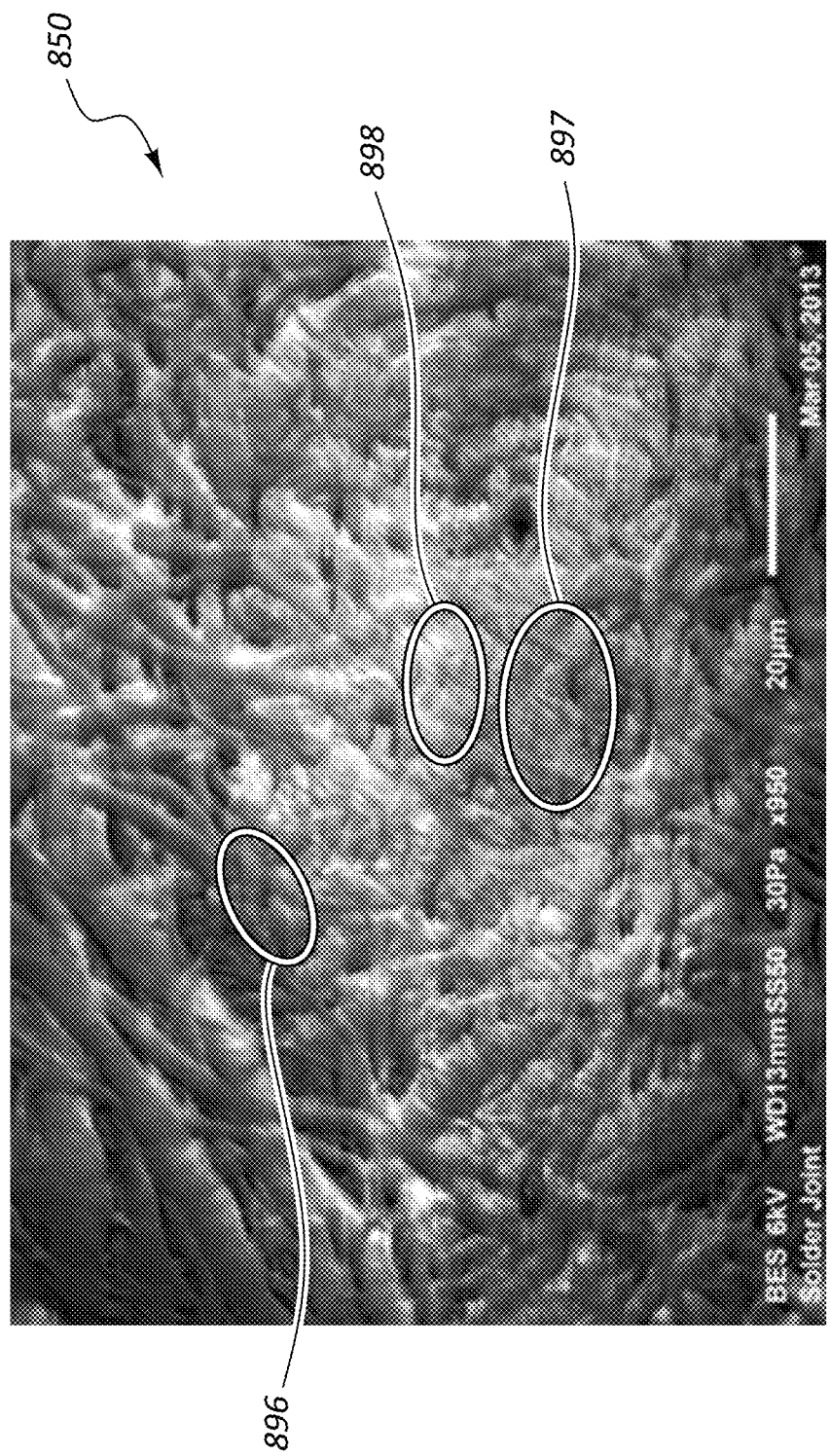
FIG. 22 is an SEM at 950× magnification of a serially deposited fiber mat which has been partially to fully densified.

FIG. 22 is an SEM at 950× magnification of a serially deposited fiber mat 850 which has been densified. A mat of serially deposited fibers may be densified by mechanically forcing fibers together, application of heat to the fiber mat, or both. For example, a hot roller may be used to densify a serially deposited fiber mat. Densifying may be configured to reduce the porosity of the mat and/or force the fibers together. Densifying may further reduce the average pore size of the mat. Serially deposited fiber mats having average pore sizes of 2 µm or greater may be considered low density mats (or portions of mats), mats (or portions thereof) having average pore sizes of 1.0 µm to 1.99 µm may be considered more dense, and mats (or portions thereof) having average pore sizes from 0 µm to 0.99 µm may be termed fully dense. By way of illustration, FIG. 22 depicts a low density portion of a mat 896, a more dense portion of a mat 897, and a fully dense portion of a mat 898.

In some instances, mechanical strength of a fiber mat may increase as pore size decreases; for example, a densified mat may have greater mechanical strength than a non-densified mat of otherwise similar characteristics. Additionally, mats with smaller pore sizes may be less permeable to biologic material, including less permeable to tissue ingrowth. A fully dense serially deposited fiber mat may be considered impermeable to tissue ingrowth and, for example, may be used as a tie layer configured to increase device strength and/or reduce the permeability of a device (e.g., a stent graft) to tissue and/or fluid.

In some exemplary embodiments, a serially deposited fiber mat may be densified by heating and compressing the fiber mat using point pressure. In some instances the heat and pressure may be applied until the fiber structure is no longer present. In some instances, pressure and heat applied by a soldering iron to a fiber mat may be used to densify the fiber mat. The soldering iron may be heated to 700° F. and the fiber mat may be compressed between the soldering iron and a mandrel. In some instances, the mandrel may be rotated during densification, to facilitate creation of densified rings on tubular mats. Serially deposited fiber mats may also be densified by disposing a mat between two flat plates which may be pressed together (e.g., by clamping) and/or heated. Serially deposited fiber mats may also or alternatively be processed through opposing rollers, such as calendaring rollers.

In some embodiments a stent graft or other tubular appliance may be configured with scalloped ends. In other words, an end of a tubular member may comprise cut-away portions around a circumference of the tubular member at the scalloped end. Scalloped ends may be configured to reduce infolding of the stent cover at the ends. For example, in some instances, a stent may have a larger diameter than a vessel in which it is deployed. Thus, the vessel may partially compress the stent radially. In some instances this radial compression may create folds or wrinkles in flat cut stent covers. These folds may then impede blood flow or lead to clotting within the vessel. Scalloped ends may reduce the occurrence of infolding at the end of a radially compressed stent. Additionally, scalloped ends may further provide a transition zone between a body lumen and a stent graft or other appliance. This transition zone may be less traumatic than a sharp transition. Use of scalloped ends may reduce the occurrence of edge stenosis in connection with implantable medical devices. Use of scalloped ends is further referenced in U.S. patent application Ser. No. 13/742,025, filed on Jan. 15, 2013, and titled "Rotational Spun Material Covered Medical Appliances and Methods of Manufacture," which is incorporated by reference in its entirety, as noted above.

As referenced above, various serially deposited fiber mats may be constructed in various ways. For example, in some exemplary embodiments, a serially deposited fiber mat may be fabricated as described below. This description is exemplary and not intended to indicate that all rotational spun fiber mats must be fabricated according to the exemplary parameters disclosed.

In some embodiments a rotational spun fiber mat may be fabricated by first mixing 50 wt % to 70 wt %, including 60 wt %, PTFE water dispersion with PEO and water to create a 0.05 g to 0.11 g—including 0.06 g to 0.08 g, and 0.07 g—PEO/ml total mixture. The mixture may then be mixed, for example, in a jar roller. In some embodiments the mixture may be mixed in the jar roller for from two to eight days, including for seven days. The mixture may then be filtered to remove any inconsistencies. In some examples, filtration by a 1-10 µm filter, including by a 5 µm filter, may remove such inconsistencies. The filtered mixture may then be fed, including embodiments wherein the mixture is continuously fed, into the rotating head of a rotational spinning apparatus. In some embodiments, the material may be fed at about 0.5 ml per minute to about 2 ml per minute, including about 1 ml per minute, into the rotating head. The rotational spinning head may then be operated between 4,500 RPM and 10,000 RPM, including between 5,000 RPM and 8,500 RPM, to rotational spin fibers from the mixture. In some instances the fibers may be collected on rotating mandrels, including mandrels rotating between 20 RPM and 300 RPM or mandrels rotating between 20 RPM and 10,000 RPM, including between 1,000 RPM and 10,000 RPM. Depending on desired mat thickness, the operation may be shortened or extended, though in some embodiments fibers may be spun for between 1 minute and 10 minutes, including between 2 minutes and 5 minutes. After spinning, the mandrels and deposited fibers may be heated to a temperature between 370° C. and 400° C., including a temperature of 385° C. (for example, by placing them in an oven at that temperature) for 5-25 minutes to sinter PTFE fibers and remove the PEO and water by evaporation.

As also referenced above, sintered serially deposited fibers may be post-processed, including processing by heating and stretching the fiber mat. In some instances, heating and stretching may tend to align the fibers of the fiber mat. Continuing the exemplary process detailed above, after sintering, a serially deposited PTFE fiber mat may then be reheated at temperatures between 285° C. and 385° C., then stretched while the mat remains at temperature. The mat may then be cooled while maintaining the stretched length. In some instances mats may be stretched to between 1.5 and 3.5 times or more the original length of the mat. As with the description of rotational spinning of fibers, this description is exemplary and not intended to indicate that all stretched fiber mats must be stretched according to the exemplary parameters disclosed.

The characteristics and modes of describing serially deposited fiber mats as disclosed herein are not mutually exclusive. For example, it is within the scope of this disclosure to describe a fiber mat in terms of both its average pore size and the number of intersections or branches per unit area of the serially deposited fiber mat. The following examples represent exemplary embodiments and are intended only as examples and not to limit this disclosure in any way. Additionally, the exemplary embodiments below represent various exemplary combinations of features of fiber mats and devices. These embodiments are exemplary, not exhaustive.

Serially deposited fiber coatings or layers may further be configured as drug-eluting layers. In other words, a serially deposited fiber mat may incorporate a drug or other therapeutic agent and/or may control the release of a drug or other therapeutic agent. For example, in some embodiments, a drug-eluting serially deposited fiber mat may comprise a therapeutic agent that has been incorporated into the serially deposited fiber mat. In certain embodiments, the therapeutic agent can be mixed with a solution of flowable material before it is serially deposited. In such embodiments, the therapeutic agent may be mixed with a solution of flowable material comprising, for example, one or more dispersions, carrier solutions, suspensions, liquids, molten or semi-molten materials, or other fluid or semi-fluid material. In one such embodiment, the therapeutic agent is mixed with a carrier solution and is then serially deposited onto a medical device, thereby providing a therapeutic agent associated with the serially deposited fibers.

In other embodiments, the drug-eluting serially deposited fiber mats comprise a therapeutic agent that has been applied to the serially deposited fiber mat after the mat has been applied to a medical device or collector. The therapeutic agent can be, for example, sprayed or painted onto the serially deposited fiber mat. In some embodiments, the serially deposited fiber mat can be dipped or rolled in the therapeutic agent. In certain embodiments, the therapeutic agent is associated with the drug-eluting serially deposited fiber mat during the deposition of the fibers. In other embodiments, the therapeutic agent is associated with the drug-eluting serially deposited fiber mat subsequent to the deposition of the fibers.

In certain embodiments, the therapeutic agent may be selected from at least one of paclitaxel, rapamycin, beta-lapachone, vitamin D, a bismuth-containing compound, heparin, iopromide or other contrast agent; analogs of any of the foregoing; and mixtures thereof. In some embodiments, the therapeutic agent is selected from at least one of rapamycin, paclitaxel, a bismuth-containing compound, heparin, and analogs of any of the foregoing. In other embodiments, the therapeutic agent may be present in combination with a second therapeutic agent. For example, the therapeutic agent is at least one of paclitaxel, rapamycin, heparin, and analogs thereof, and the second therapeutic agent is at least one of beta-lapachone, vitamin D, and their analogs. In further embodiments, the therapeutic agent may be selected from at least one of rapamycin (also known as sirolimus), fujimycin (also known as tacrolimus), umirolimus, an antibiotic, an antifungal agent, an autophagy activator, an enzyme, an enzyme inhibitor, a protein including an antibody, an immunoregulator, a kinase, and a phosphatase. In still further embodiments, the therapeutic agent may include one or more steroids, immunosuppressants, anti-proliferatives, proliferatives, anti-infectives, anti-thrombotics, thrombotics, nutritional additives, prophylactics, or preventative agents. In an embodiment, the therapeutic agent is dexamethasone. In further embodiments, the therapeutic agent may be a cell or mixture of cells, for example, for use in skin grafts, tissue engineering, bone regrowth, or similar prosthetic indications. The therapeutic agent may be present in a salt form or as a prodrug.

In some embodiments, a serially deposited fiber mat disposed on a medical device can increase the polymeric surface area of the medical device, which may improve the delivery of the associated therapeutic agent to a target tissue. Without being bound by theory, the additional surface area provided by the serially deposited fiber mat may increase the contact area between the drug-eluting serially deposited fiber mat on the medical device and a target tissue and/or biological fluid. For certain embodiments described herein, the release rate of the therapeutic agent may be generally proportional to the surface area of the drug-eluting serially deposited fiber mat on the medical device. In other embodiments, the increased surface area created by the serially deposited fiber mat may increase the rate of delivery of the therapeutic agent.

In certain embodiments, a drug-eluting serially deposited fiber mat may allow for a controlled release, such as an immediate release, of an effective dose of a therapeutic agent to a target tissue. In particular embodiments, a drug-eluting serially deposited fiber mat may allow for the relatively rapid release of an effective dose of a therapeutic agent to a target tissue in approximately 5 minutes or less. In some embodiments, the drug-eluting serially deposited fiber mat may allow for the controlled release of an effective dose of a therapeutic agent to a target tissue in approximately 5 minutes or less, 4 minutes or less, 3 minutes or less, 2.5 minutes or less, 2 minutes or less, 1.8 minutes or less, 1.6 minutes or less, 1.4 minutes or less, 1.2 minutes or less, 1 minute or less, 0.9 minutes or less, 0.8 minutes or less, 0.7 minutes or less, 0.6 minutes or less, 0.5 minutes or less, 0.4 minutes or less, 0.3 minutes or less, 0.2 minutes or less, or 0.1 minutes or less.

In other embodiments the increased surface area created by a serially deposited fiber mat may increase the bioavailability of a therapeutic agent. Without being bound by theory, the increased surface area may provide for a more efficient release of a therapeutic agent and an increased drug absorption by the target tissue. In such embodiments, increased surface area can allow for a reduction in the amount of therapeutic agent that is used to deliver an effective dose, in comparison to the amount used without a serially deposited fiber mat coating. In certain such embodiments, the increased surface area may allow an effective dose of therapeutic agent to be delivered to the target tissue while using approximately less than 10%, 20%, 30%, 40%, 50%, 60%, 70%, 80%, or 90% of the therapeutic agent used without the presence of a drug-eluting serially deposited fiber mat on the medical device.

In certain embodiments of the medical devices disclosed herein, the surface area of a serially deposited fiber mat may be adjusted by increasing or decreasing the density or fiber size of the serially deposited fiber mat. In other embodiments, a medical device may be coated with one or more layers of serially deposited fibers wherein the various layers may be in different orientations relative to each other. In some embodiments, the surface area of the serially deposited fiber mat may be adjusted in order to control the delivery rate of the associated therapeutic agent. In some embodiments, the serially deposited fiber layers can be coupled with non-serially deposited layers, including, for example, sheets, films, and tubes of other polymeric or biological materials. Drug elution in serially deposited fiber mats is further discussed in U.S. patent application Ser. No. 13/787,327, titled "Drug-Eluting Rotational Spun Coatings and Methods of Use," filed on Mar. 6, 2013 and herein incorporated by reference in its entirety.

Example 5.1

The generally random fiber mat of FIG. 18 was produced as follows. A 60 wt % PTFE water dispersion was mixed with PEO to obtain a 0.07 g/ml mixture of PEO to PTFE dispersion. The mixture was strained through a filter to remove any large particles. The combined solution was then allowed to sit and/or was mixed in a non-agitating jar roller until the solution achieved homogeneity. The combined solution was then rotational spun from a spinneret at about 3,500 RPM and collected. The orifices on the spinneret were about 27 gauge openings. The mat was then sintered at about 385° C.

Example 5.2

The generally aligned fiber mat of FIG. 19 was produced by creating a random fiber mat according to the same parameters recited in Example 5.1. The fiber mat was then heated at a temperature of 385° C. and stretched to 3.5 times its original length.

The more aligned disposition of the fibers of the mat of Example 5.2, as compared to the fiber mat of Example 5.1, is shown in FIGS. 18 and 19.

Example 5.3

The densified fiber mat of FIG. 22 was produced by creating a random fiber mat with similar parameters to those recited in Example 5.1. After sintering and initial cooling, the fibers were then heated and compressed by applying a soldering iron heated to 700° F. to the fiber mat. The fiber mat was disposed on a rotating mandrel as the heat and pressure were applied. The soldering iron was traversed axially back and forth along the tube until a portion (~10 cm) of the fiber mat was densified. The change in fiber distinction and structure between an undensified mat, such as described in Examples 5.1 and 5.2, and the densified mat of Example 5.3 is shown in FIGS. 18, 19, and 22.

EXEMPLARY EMBODIMENTS

I. Method of Manufacture

In one embodiment, a method of manufacturing a polymeric material comprises obtaining a membrane comprising a mat of sintered polymeric fibers and stretching the membrane in a first direction to at least partially elongate the membrane in the first direction.

The membrane may be heated and stretched while the membrane is at an elevated temperature.

Obtaining the membrane may comprise serially depositing the polymeric fibers on a collection apparatus to form a membrane and sintering the membrane to set the structure of the fibers.

The polymeric fibers may be serially deposited by rotational spinning the polymeric fibers onto the collection apparatus.

The polymeric fibers may be serially deposited by electrospinning the polymeric fibers onto the collection apparatus.

Heating the membrane may comprise the same step as sintering the membrane.

Heating the membrane may comprise a separate step from sintering the membrane.

The polymeric fibers may comprise polytetrafluoroethylene (PTFE).

The membrane may be sintered at about 150° C. or more.
The membrane may be sintered at about 200° C. or more.
The membrane may be sintered at about 250° C. or more.
The membrane may be sintered at about 300° C. or more.
The membrane may be sintered at about 350° C. or more.
The membrane may be sintered at about 370° C. or more.
The membrane may be sintered at about 385° C. or more.
The membrane may be heated to at least the crystalline melt temperature of the polymeric fibers.

The membrane may be stretched such that the polymeric fibers tend to align in the first direction.

The membrane may be stretched to at least 150% of its original length in the first direction.
The membrane may be stretched to at least 200% of its original length in the first direction.
The membrane may be stretched to at least 250% of its original length in the first direction.
The membrane may be stretched to at least 300% of its original length in the first direction.
The membrane may be stretched to at least 350% of its original length in the first direction.

The membrane may be twisted to entangle the fibers before the membrane is sintered.

Stretching the membrane may increase the resistance of the membrane to creep in the first direction.

The membrane may be stretched in a second direction while the membrane is at an elevated temperature to at least partially elongate the membrane in the second direction.

The membrane may be simultaneously stretched in the first and second directions while the membrane is at an elevated temperature.

Stretching the membrane in a first direction and a second direction may increase the resistance of the membrane to creep in the first direction and in the second direction.

Stretching the membrane may reduce the thickness of the membrane.

Stretching the membrane may reduce the thickness of the membrane between 10% and 90%.

The stretched membrane may be coupled to a second polymeric layer.

The stretched membrane may be coupled to a second polymeric layer and a third polymeric layer.

The second polymeric layer may be disposed between the membrane and the third polymeric layer and bond to both the membrane and the third polymeric layer.

The second polymeric layer may comprise fluorinated ethylene propylene (FEP).

The third polymeric layer may comprise a serially deposited PTFE fiber mat and the polymeric fibers of the membrane may comprise PTFE.

The third polymeric layer may be sintered then heated and stretched.

The second polymeric layer may comprise expanded PTFE.

II. Polymeric Material

In one embodiment, a polymeric material comprises a membrane that is comprised of serially deposited polymeric fibers that have been stretched in a first direction after the fibers have been serially deposited.

The polymeric fibers may be rotational spun polymeric fibers.

The polymeric fibers may be electrospun polymeric fibers.

The fibers may comprise sintered fibers prior to being stretched.

The fibers may be set in a stretched configuration from exposure to an elevated temperature.

The fibers may be stretched at a temperature at or above the crystalline melting point of the polymeric material.

The fiber membrane may be at least 150% of its original length in the first direction upon stretching.

The fiber membrane may be at least 300% of its original length in the first direction upon stretching.

The fibers may be generally aligned in the first direction.

The polymeric material may comprise polytetrafluoroethylene (PTFE).

The membrane may be more resistant to creep in the first direction after the membrane is stretched.

The membrane may be more resistant to creep in the first direction than in a second direction oriented perpendicular to the first direction.

The serially deposited polymeric fibers may have been stretched in a second direction.

The membrane may be more resistant to creep in the first and second directions after the membrane is stretched.

The polymeric material may further comprise a second polymeric layer.

The polymeric material may further comprise a third polymeric layer.

The second polymeric layer may be disposed between the membrane and the third polymeric layer and the second polymeric layer may bond to both the membrane and the third polymeric layer.

The second polymeric layer may comprise fluorinated ethylene propylene (FEP).

The third material layer may comprise a serially deposited PTFE fiber mat and the polymeric fibers of the membrane may comprise PTFE.

The third material layer may have been sintered then heated and stretched.

The second polymeric layer may comprise expanded PTFE.

The polymeric material may further comprise a reinforcing member selected from at least one of: Nitinol, stainless steel, chromium cobalt (MP35N), or titanium.

One or more of the second polymeric layer and the membrane may be configured to be blood contacting.

III. Method of Resisting Creep in a Medical Appliance

An embodiment of a method of resisting creep in a medical appliance may comprise obtaining a medical appliance comprised of serially deposited and sintered polymeric fibers, heating the medical appliance at an elevated temperature, and stretching the medical appliance in a first direction such that the medical appliance is more resistant to creep in the first direction after stretching.

The serially deposited and sintered polymeric fibers may be rotational spun.

The serially deposited and sintered polymeric fibers may be electrospun.

The serially deposited and sintered polymeric fibers may comprise polytetrafluoroethylene (PTFE).

The medical appliance may further comprise a tubular member and the first direction may be in an axial direction of the tubular member.

The medical appliance may further comprise a tubular member and the first direction may be in a radial direction of the tubular member.

Stretching the medical appliance may comprise stretching the medical appliance to between 150% and 350% of its original length in the first direction.

The medical appliance may comprise a vascular graft.

The medical appliance may comprise a stent graft.

IV. Method of Setting a Geometry of a Polymeric Material

In one embodiment, a method of setting a geometry of a polymeric material comprises obtaining a polymeric membrane comprising a mat or serially deposited polymeric fibers, constraining the polymeric membrane into a desired geometry, and heating the polymeric membrane while constrained.

Obtaining the polymeric membrane may comprise obtaining a sintered polymeric membrane.

Heating the polymeric membrane may comprise heating the polymeric membrane to a temperature lower than a temperature at which the polymeric membrane was sintered.

Heating the polymeric membrane may comprise heating the polymeric membrane at a temperature at or above the crystalline melt temperature of the polymeric material.

The polymeric membrane may comprise a tubular membrane of serially deposited polytetrafluoroethylene (PTFE) fibers.

The PTFE fibers may be rotational spun fibers.

The PTFE fibers may be electrospun fibers.

The tubular membrane may be stretched in an axial direction prior to constraining the tubular membrane.

The polymeric membrane may be constrained by axially compressing the tubular membrane onto a mandrel to form a corrugated tube.

Heating the polymeric membrane may comprise heating the polymeric membrane at about 325° C. or more.

The sintered polymeric membrane may be heated at an elevated temperature and stretched to at least 150% of the original length of the sintered polymeric membrane before the membrane is constrained.

V. Tubular Graft

In one embodiment, a tubular graft may comprise a tube of serially deposited polytetrafluoroethylene (PTFE) fibers and the tube may be heat-set in an axially compressed state such that the tube has a generally corrugated shape.

The serially deposited PTFE fibers may be rotational spun fibers.

The serially deposited PTFE fibers may be electrospun fibers.

The tube may be heat-set after the tube is initially sintered.

A smooth walled tube may be coupled to the corrugated tube of the tubular graft such that the smooth walled tube is coaxial with and overlaps the corrugated tube.

The smooth walled tube may define an inside diameter of the tubular graft, and the corrugated tube may define an outside diameter of the corrugated graft.

The smooth walled tube may be configured to be blood contacting.

The tube may have been heated at an elevated temperature and stretched to at least 150% of the original length of the tube after the tube has been sintered and before the tube is heat-set.

VI. Reinforced Tubular Graft

In one embodiment, a reinforced tubular graft comprises a first layer that comprises a first mat of serially deposited polytetrafluoroethylene (PTFE) fibers, and one or more reinforcing rings disposed around the first layer.

The reinforcing rings may comprise rings of fluorinated ethylene propylene (FEP) disposed around the first layer.

A second layer that comprises a second mat of serially deposited PTFE fibers may be disposed over the reinforcing rings.

The one or more reinforcing rings may be removable by a practitioner.

The one or more reinforcing rings may be configured to resist kinking.

One or more of the first and second layers may comprise rotational spun fibers.

One or more of the first and second layers may comprise electrospun fibers.

The reinforcing rings may comprise densified regions of the first layer.

The densified regions may comprise segments of the first layer densified by heating and compression.

The reinforcing rings may comprise corrugations formed in the first layer.

The first layer may be heat-set in a corrugated configuration.

The first layer may be configured to be blood contacting.

VII. Method of Suturing a Medical Appliance

In one embodiment, a method of suturing a medical appliance comprises pulling a suture through a mat of serially deposited polymeric fibers.

The serially deposited polymeric fibers may be rotational spun fibers.

The serially deposited polymeric fibers may be electrospun fibers.

VIII. Mat of Polymeric Fibers that Elastically Recoil

In one embodiment, a mat comprises serially deposited polymeric fibers that are configured to elastically recoil after an instrument pierces the mat to resist fluid leakage through the mat.

The fibers may be configured to elastically recoil around a suture disposed in the mat.

The serially deposited polymeric fibers may be rotational spun fibers.

The serially deposited polymeric fibers may be electrospun fibers.

IX. Artificial Joint(s)

In one embodiment, an artificial joint comprises a base component and a layer of serially deposited polymeric fibers disposed on a surface of the base component.

The layer of serially deposited fibers may comprise rotational spun fibers.

The layer of serially deposited fibers may comprise electrospun fibers.

The joint may comprise a hip implant.

The joint may comprise a knee implant.

The layer of serially deposited polymeric fibers may be disposed such that it interacts with an artificial component that is separate from the base component and configured to move with respect to the base component.

The layer of serially deposited polymeric fibers may be disposed such that it interacts with a biologic structure which moves with respect to the base component.

The layer may have a different coefficient of friction than the surface of the base component.

X. Coated Catheter

In one embodiment, a catheter comprises a base structure and a coating that comprises a mat of serially deposited polymeric fibers and is disposed on a portion of the base structure.

The mat of serially deposited polymeric fibers may comprise rotational spun fibers.

The mat of serially deposited polymeric fibers may comprise electrospun fibers.

The coating may have a different hydrophobicity than the surface of the base structure.

The coating may have a different coefficient of friction than the surface of the base structure.

XI. Implantable Medical Appliance

In one embodiment, an implantable medical appliance comprises a structure that comprises serially deposited ceramic fibers.

The serially deposited ceramic fibers may comprise rotational spun fibers.

The serially deposited ceramic fibers may comprise electrospun fibers.

The structure may be porous and configured for use as a scaffold for bone growth.

The structure may comprise a prosthetic vertebrae.

XII. Method of Promoting Bone Growth on a Lattice Structure

In one embodiment, a method of promoting bone growth on a lattice structure comprises obtaining a lattice structure comprising serially deposited fibers and implanting the lattice structure into a body such that the lattice structure is disposed adjacent a structure of a skeletal system of the body.

The lattice structure may comprise serially deposited ceramic fibers.

The serially deposited fibers may be rotational spun.

The serially deposited fibers may be electrospun.

XIII. Fiber Diameter

In one embodiment, a serially deposited fiber mat comprises serially deposited fibers in which 95% of the fiber diameters are from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 nm to 800 μm thick.

The serially deposited fiber mat may be from 50 μm to 200 μm thick.

The serially deposited fibers may have an average fiber density from 5,000 to 150,000 fibers per $mm^2$.

The serially deposited fibers may have an average fiber density from 12,000 to 55,000 fibers per $mm^2$.

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per $mm^2$.

The serially deposited fibers may define between 4,000 and 65,000 intersections per $mm^2$.

The serially deposited fibers may define between 0 and 20,000 branches per $mm^2$.

The serially deposited fibers may define between 400 and 7,500 branches per $mm^2$.

The serially deposited fibers may define between 0 and 30,000 bundles per $mm^2$.

The serially deposited fibers may define between 400 and 10,000 bundles per $mm^2$.

No more than 20% of the angles formed by fibers comprising branches or intersections may fall in a range of 10°.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XIV. Mat Thickness

In one embodiment, a serially deposited fiber mat comprises a mat from 50 nm to 800 μm thick.

Ninety-five percent of the serially deposited fibers may have diameters from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 μm to 200 μm thick.

The serially deposited fibers may have an average fiber density from 5,000 to 150,000 fibers per mm².

The serially deposited fibers may have an average fiber density from 12,000 to 55,000 fibers per mm².

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per mm².

The serially deposited fibers may define between 4,000 and 65,000 intersections per mm².

The serially deposited fibers may define between 0 and 20,000 branches per mm².

The serially deposited fibers may define between 400 and 7,500 branches per mm².

The serially deposited fibers may define between 0 and 30,000 bundles per mm².

The serially deposited fibers may define between 400 and 10,000 bundles per mm².

No more than 20% of the angles formed by fibers comprising branches or intersections may fall in a range of 10°.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XV. Fiber Density

In one embodiment, a serially deposited fiber mat comprises fibers having an average fiber density from 5,000 to 150,000 fibers per mm².

Ninety-five percent of the serially deposited fibers may have diameters from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 μm to 800 μm thick.

The serially deposited fiber mat may be from 50 μm to 200 μm thick.

The serially deposited fibers may have an average fiber density from 12,000 to 55,000 fibers per mm².

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per mm².

The serially deposited fibers may define between 4,000 and 65,000 intersections per mm².

The serially deposited fibers may define between 0 and 20,000 branches per mm².

The serially deposited fibers may define between 400 and 7,500 branches per mm².

The serially deposited fibers may define between 0 and 30,000 bundles per mm².

The serially deposited fibers may define between 400 and 10,000 bundles per mm².

No more than 20% of the angles formed by fibers comprising branches or intersections may fall in a range of 10°.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XVI. Pore Diameter

In one embodiment, a serially deposited fiber mat comprises a mat wherein the effective diameters of at least 50 randomly identified pores collectively average from 1 µm to 10 µm.

Ninety-five percent of the serially deposited fibers may have diameters from 50 nm to 6 µm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 µm.

Ninety-five percent of the serially deposited fibers may have diameters from 900 nm to 2 µm.

The serially deposited fiber mat may be from 50 µm to 800 µm thick.

The serially deposited fiber mat may be from 50 µm to 200 µm thick.

The serially deposited fibers may have an average fiber density from 5,000 to 150,000 fibers per mm².

The serially deposited fibers may have an average fiber density from 12,000 to 55,000 fibers per mm².

At least 50 randomly identified pores in the serially deposited fiber mat may have effective diameters that collectively average from 2 µm to 3.5 µm.

The serially deposited fibers may define between 100 and 100,000 intersections per mm².

The serially deposited fibers may define between 4,000 and 65,000 intersections per mm².

The serially deposited fibers may define between 0 and 20,000 branches per mm².

The serially deposited fibers may define between 400 and 7,500 branches per mm².

The serially deposited fibers may define between 0 and 30,000 bundles per mm².

The serially deposited fibers may define between 400 and 10,000 bundles per mm².

No more than 20% of the angles formed by fibers comprising branches or intersections may fall in a range of 10°.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XVII. Intersections

In one embodiment, a serially deposited fiber mat comprises a mat having between 100 and 100,000 intersections per mm².

Ninety-five percent of the serially deposited fibers may have diameters from 50 nm to 6 µm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 µm.

Ninety-five percent of the serially deposited fibers may have diameters from 900 nm to 2 µm.

The serially deposited fiber mat may be from 50 µm to 800 µm thick.

The serially deposited fiber mat may be from 50 µm to 200 µm thick.

The serially deposited fibers may have an average fiber density from 5,000 to 150,000 fibers per mm².

The serially deposited fibers may have an average fiber density from 12,000 to 55,000 fibers per mm².

At least 50 randomly identified pores in the serially deposited fiber mat may have effective diameters that collectively average from 1 µm to 10 µm.

At least 50 randomly identified pores in the serially deposited fiber mat may have effective diameters that collectively average from 2 µm to 3.5 µm.

The serially deposited fibers may define between 4,000 and 65,000 intersections per mm².

The serially deposited fibers may define between 0 and 20,000 branches per mm².

The serially deposited fibers may define between 400 and 7,500 branches per mm$^2$.

The serially deposited fibers may define between 0 and 30,000 bundles per mm$^2$.

The serially deposited fibers may define between 400 and 10,000 bundles per mm$^2$.

No more than 20% of the angles formed by fibers comprising branches or intersections may fall in a range of 10°.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XVIII. Branches

In one embodiment, a serially deposited fiber mat comprises a mat having between 0 and 20,000 branches per mm$^2$.

Ninety-five percent of the serially deposited fibers may have diameters from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 μm to 800 μm thick.

The serially deposited fiber mat may be from 50 μm to 200 μm thick.

The serially deposited fibers may have an average fiber density from 5,000 to 150,000 fibers per mm$^2$.

The serially deposited fibers may have an average fiber density from 12,000 to 55,000 fibers per mm$^2$.

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per mm$^2$.

The serially deposited fibers may define between 4,000 and 65,000 intersections per mm$^2$.

The serially deposited fibers may define between 400 and 7,500 branches per mm$^2$.

The serially deposited fibers may define between 0 and 30,000 bundles per mm$^2$.

The serially deposited fibers may define between 400 and 10,000 bundles per mm$^2$.

No more than 20% of the angles formed by fibers comprising branches or intersections may fall in a range of 10°.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XIX. Bundles

In one embodiment, a serially deposited fiber mat comprises a mat having between 0 and 30,000 bundles per mm$^2$.

Ninety-five percent of the serially deposited fibers may have diameters from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 μm to 800 μm thick.

The serially deposited fiber mat may be from 50 μm to 200 μm thick.

The serially deposited fibers may have an average fiber density from 5,000 to 150,000 fibers per mm$^2$.

The serially deposited fibers may have an average fiber density from 12,000 to 55,000 fibers per mm$^2$.

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per mm$^2$.

The serially deposited fibers may define between 4,000 and 65,000 intersections per mm$^2$.

The serially deposited fibers may define between 0 and 20,000 branches per mm$^2$.

The serially deposited fibers may define between 400 and 7,500 branches per mm$^2$.

The serially deposited fibers may define between 400 and 10,000 bundles per mm$^2$.

No more than 20% of the angles formed by fibers comprising branches or intersections may fall in a range of 10°.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XX. Random Angles

In one embodiment, a serially deposited fiber mat comprises a mat wherein no more than 20% of the angles formed by fibers comprising branches or intersections may fall in a range of 10°.

Ninety-five percent of the serially deposited fibers may have diameters from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 μm to 800 μm thick.

The serially deposited fiber mat may be from 50 μm to 200 μm thick.

The serially deposited fibers may have an average fiber density from 5,000 to 150,000 fibers per mm$^2$.

The serially deposited fibers may have an average fiber density from 12,000 to 55,000 fibers per mm$^2$.

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per mm$^2$.

The serially deposited fibers may define between 4,000 and 65,000 intersections per mm$^2$.

The serially deposited fibers may define between 0 and 20,000 branches per mm$^2$.

The serially deposited fibers may define between 400 and 7,500 branches per mm$^2$.

The serially deposited fibers may define between 0 and 30,000 bundles per mm$^2$.

The serially deposited fibers may define between 400 and 10,000 bundles per mm$^2$.

No more than 15% of the angles formed by fibers comprising branches or intersections may fall in a range of 10°.

No more than 10% of the angles formed by fibers comprising branches or intersections may fall in a range of 10°.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XXI. Aligned Angles 30° Range

In one embodiment, a serially deposited fiber mat comprises a mat wherein at least 25% of the angles formed by fibers comprising branches or intersections may fall in a range of 30°.

Ninety-five percent of the serially deposited fibers may have diameters from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 μm to 800 μm thick.

The serially deposited fiber mat may be from 50 μm to 200 μm thick.

The serially deposited fibers may have an average fiber density from 5,000 to 150,000 fibers per $mm^2$.

The serially deposited fibers may have an average fiber density from 12,000 to 55,000 fibers per $mm^2$.

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per $mm^2$.

The serially deposited fibers may define between 4,000 and 65,000 intersections per $mm^2$.

The serially deposited fibers may define between 0 and 20,000 branches per $mm^2$.

The serially deposited fibers may define between 400 and 7,500 branches per $mm^2$.

The serially deposited fibers may define between 0 and 30,000 bundles per $mm^2$.

The serially deposited fibers may define between 400 and 10,000 bundles per $mm^2$.

At least 30% of the angles formed by fibers comprising branches or intersections may fall in a range of 30°.

At least 40% of the angles formed by fibers comprising branches or intersections may fall in a range of 30°.

At least 35% of the angles formed by fibers comprising branches or intersections may fall in a range of 40°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

XXII. Aligned Angles 40° Range

In one embodiment, a serially deposited fiber mat comprises a mat wherein at least 35% of the angles formed by fibers comprising branches or intersections may fall in a range of 40°.

Ninety-five percent of the serially deposited fibers may have diameters from 50 nm to 6 μm.

The serially deposited fibers may comprise rotational spun fibers.

The serially deposited fibers may comprise electrospun fibers.

The serially deposited fibers may comprise polytetrafluoroethylene (PTFE).

Ninety-five percent of the serially deposited fibers may have diameters from 700 nm to 3 μm.

Ninety-five percent of the serially deposited fibers may have diameters from 900 nm to 2 μm.

The serially deposited fiber mat may be from 50 μm to 800 μm thick.

The serially deposited fiber mat may be from 50 μm to 200 μm thick.

The serially deposited fibers may have an average fiber density from 5,000 to 150,000 fibers per $mm^2$.

The serially deposited fibers may have an average fiber density from 12,000 to 55,000 fibers per $mm^2$.

At least 50 randomly identified pores in the serially deposited fiber mat may have effective diameters that collectively average from 1 μm to 10 μm.

At least 50 randomly identified pores in the serially deposited fiber mat may have effective diameters that collectively average from 2 μm to 3.5 μm.

The serially deposited fibers may define between 100 and 100,000 intersections per $mm^2$.

The serially deposited fibers may define between 4,000 and 65,000 intersections per $mm^2$.

The serially deposited fibers may define between 0 and 20,000 branches per $mm^2$.

The serially deposited fibers may define between 400 and 7,500 branches per $mm^2$.

The serially deposited fibers may define between 0 and 30,000 bundles per $mm^2$.

The serially deposited fibers may define between 400 and 10,000 bundles per $mm^2$.

At least 25% of the angles formed by fibers comprising branches or intersections may fall in a range of 30°.

At least 30% of the angles formed by fibers comprising branches or intersections may fall in a range of 30°.

At least 40% of the angles formed by fibers comprising branches or intersections may fall in a range of 30°.

At least 50% of the angles formed by fibers comprising branches or intersections may fall in a range of 40°.

At least 55% of the angles formed by fibers comprising branches or intersections may fall in a range of 40°.

The serially deposited fiber mat may comprise a layer of a multilayered construct.

The multilayered construct may comprise an impermeable layer.

The multilayered construct may be wholly comprised of PTFE.

The multilayered construct may comprise only serially deposited PTFE.

The multilayered construct may comprise no layers of ePTFE.

The serially deposited fiber mat may comprise a portion of a medical appliance.

The medical appliance may comprise a stent graft.

The medical appliance may comprise a graft.

The medical appliance may comprise a patch.

The medical appliance may comprise a vascular prosthesis.

The examples and embodiments disclosed herein are to be construed as merely illustrative and exemplary, and not as a limitation of the scope of the present disclosure in any way. It will be apparent to those having skill in the art with the aid of the present disclosure that changes may be made to the details of the above-described embodiments without departing from the underlying principles of the disclosure herein. It is intended that the scope of the invention be defined by the claims appended hereto and their equivalents.

The invention claimed is:

1. A method of manufacturing a polymeric material, the method comprising:
   obtaining a membrane of sintered polymeric fibers, wherein obtaining the membrane comprises:
   serially depositing polymeric fibers on a collection apparatus, wherein the polymeric fibers are randomly deposited;
   sintering the membrane to set the structure of the fibers; and
   stretching the membrane in a first direction to at least partially elongate the membrane in the first direction with the membrane heated to a temperature higher than a crystalline melt temperature of the fibers, such that the polymeric fibers tend to align in the first direction such that the membrane is more resistant to creep in the first direction after the membrane is stretched;
   wherein the membrane comprises a thickness that is smaller than a width dimension;
   wherein the stretching temperature is greater than or equal to 370° C.;
   the method further comprising, obtaining a tubular mat of serially deposited, sintered polymeric fibers; and
   helically wrapping the tubular mat with the membrane, such that the polymeric material is more resistant to radial creep.

2. The method of claim 1, wherein the membrane is sintered at about 370° C. or more.

3. The method of claim 1, wherein stretching the membrane comprises stretching the membrane to at least 150% of its original length in the first direction.

4. The method of claim 1, further comprising stretching the membrane in a second direction, while the membrane is at an elevated temperature, to at least partially elongate the membrane in the second direction.

5. The method of claim 1, further comprising heating the membrane and constraining the polymeric membrane into a desired geometry, wherein heating the membrane comprises heating the membrane while the polymeric membrane is constrained.

6. The method of claim 1, wherein obtaining a membrane comprising a mat of sintered polymeric fibers comprises:
   mixing a PTFE-water dispersion comprising from 50 wt % to 70 wt % PTFE with PEO to create a mixture having from 0.05 to 0.11 g PEO/ml of total mixture;
   rotational spinning the mixture between 4,500 RPM and 10,000 RPM;
   collecting rotational spun fibers on a mandrel rotating between 20 RPM and 10,000 RPM; and
   sintering the collected fibers at a temperature between 370° C. and 400° C.

7. The method of claim 6, wherein sintering the collected fibers comprises heating the fibers at a temperature between 370° C. and 400° C. for between 5 minutes and 25 minutes.

8. A method of manufacturing a polymeric material, the method comprising:
   obtaining a membrane of sintered polymeric fibers, wherein obtaining the membrane comprises:
   serially depositing polymeric fibers on a collection apparatus, wherein the polymeric fibers are randomly deposited;
   sintering the membrane to set the structure of the fibers; and
   stretching the membrane in a first direction to at least partially elongate the membrane in the first direction with the membrane heated to a temperature higher than a crystalline melt temperature of the fibers such that the membrane is more porous after stretching the membrane in the first direction;
   wherein the stretching temperature is lower than a sintering temperature;
   the method further comprising obtaining a tubular mat of serially deposited, sintered polymeric fibers; and
   helically wrapping the tubular mat with the membrane, such that the polymeric material is more resistant to radial creep.

9. The method of claim 8, wherein the membrane is 10 times more porous after stretching the membrane in the first direction.

10. A method of manufacturing a polymeric material, the method comprising:
    obtaining a membrane of sintered polymeric fibers, wherein obtaining the membrane comprises:
    serially depositing polymeric fibers on a collection apparatus, wherein the polymeric fibers are randomly deposited;
    sintering the membrane to set the structure of the fibers;
    work-hardening the membrane with the membrane heated to a temperature higher than a crystalline melt temperature of the fibers;
    obtaining a tubular mat of serially deposited, sintered polymeric fibers; and
    helically wrapping the tubular mat with the membrane, such that the polymeric material is more resistant to radial creep.

11. The method of claim 10, wherein work-hardening comprises stretching the membrane in a first direction to at least partially elongate the membrane in the first direction with the membrane heated to a temperature higher than a melt point of the fibers.

12. The method of claim 11, wherein the polymeric fibers tend to align in the first direction.

13. The method of claim 12, wherein heating the membrane to a temperature higher than 370 degrees Celsius tends to cause greater alignment of the polymeric fibers as compared to lower temperatures.

14. The method of claim 11, wherein work-hardening further comprises stretching the membrane in a second direction to at least partially elongate the membrane in a second direction with the membrane heated to a temperature higher than a melt point of the fibers.

15. The method of claim 10, wherein the membrane is more resistant to creep in the first direction after the membrane is work-hardened.

16. The method of claim 11, wherein the membrane is more porous after stretching the membrane in the first direction.

17. The method of claim 10, wherein the tensile strength of the membrane is increased after work-hardening.

18. The method of claim 1, wherein the stretching temperature is lower than a sintering temperature.

19. The method of claim 1, wherein an alignment of the fibers is greater than an alignment of fibers if the membrane were stretched at a temperature less than 370° C.

20. The method of claim 8, wherein the membrane comprises a thickness that is smaller than a width dimension,
   wherein the stretching temperature is greater than or equal to 370° C., and
   wherein an alignment of the fibers is greater than an alignment of fibers if the membrane were stretched at a temperature less than 370° C.

21. The method of claim 10, wherein the stretching temperature is lower than a sintering temperature.

\* \* \* \* \*